US008173130B2

(12) United States Patent
Salzman et al.

(10) Patent No.: US 8,173,130 B2
(45) Date of Patent: May 8, 2012

(54) ANTIBODIES AGAINST FLAGELLIN AND USES THEREOF

(75) Inventors: Andrew L. Salzman, Herzliya (IL); Kanneganti Murthy, Stoneham, MA (US)

(73) Assignee: Inotek Pharmaceuticals Corporation, Lexington, MA (US)

( * ) Notice: Subject to any disclaimer, the term of this patent is extended or adjusted under 35 U.S.C. 154(b) by 622 days.

(21) Appl. No.: 12/231,777

(22) Filed: Sep. 5, 2008

(65) Prior Publication Data

US 2009/0191208 A1 Jul. 30, 2009

Related U.S. Application Data

(60) Provisional application No. 60/967,718, filed on Sep. 5, 2007.

(51) Int. Cl.
*A61K 39/00* (2006.01)
*A61K 39/38* (2006.01)
*A61K 39/40* (2006.01)
*A61K 39/395* (2006.01)

(52) U.S. Cl. ............... 424/150.1; 424/130.1; 424/133.1; 424/134.1; 424/136.1; 424/139.1; 424/141.1; 424/164.1; 424/178.1; 424/184.1; 436/512

(58) Field of Classification Search ........................ None
See application file for complete search history.

(56) References Cited

U.S. PATENT DOCUMENTS

| | | | |
|---|---|---|---|
| 4,831,121 | A | 5/1989 | Montie et al. |
| 4,834,976 | A | 5/1989 | Rosok et al. |
| 4,946,677 | A | 8/1990 | Dorner et al. |
| 5,179,001 | A | 1/1993 | Young et al. |
| 5,237,053 | A | 8/1993 | Dorner et al. |
| 7,361,733 | B2 | 4/2008 | Hershberg et al. |
| 2004/0043931 | A1 | 3/2004 | Hersberg et al. |
| 2004/0213795 | A1 | 10/2004 | Collins et al. |
| 2005/0215770 | A1 | 9/2005 | Bell et al. |
| 2009/0208506 | A1 | 8/2009 | Rachamim et al. |

FOREIGN PATENT DOCUMENTS

| | | |
|---|---|---|
| WO | WO-95/10776 A1 | 4/1995 |
| WO | WO-01/40280 A2 | 6/2001 |
| WO | WO-03/076472 A2 | 9/2003 |
| WO | WO-2004/048600 A2 | 6/2004 |
| WO | WO-2004/110369 A2 | 12/2004 |
| WO | WO-2005/051998 A2 | 6/2005 |
| WO | WO-2006/063093 A2 | 6/2006 |
| WO | WO-2007/087576 A2 | 8/2007 |

OTHER PUBLICATIONS

Salzman et al., (WO 01/40280 A2 published Jun. 1, 2001).*
Campieri et al., (2001. Gut. vol. 48:132-135).*
Cahill et al., (Infection and Immuity. 1997. vol. 65(8):3126-3131).*
Spangenberg, Claudia et al., "Genetic diversity of flagellins of *Pseudomonas aeruginosa*," *FEBS Letters*, vol. 396:213-217 (1996).
Wei, Li-Na et al., "Covalent Structure of Three Phase-1 Flagellar Filament Proteins of *Salmonella*," *J. Mol. Biol.*, vol. 186:791-803 (1985).
International Search Report and Written Opinion for Application No. PCT/US08/75387, dated Jan. 2, 2009.
Bernell, Olle et al., "Risk Factors for Surgery and Postoperative Recurrence of Crohn's Disease," *Annals of Surgery*, vol. 231(1):38-45 (2000).
Didierlaurent, Arnaud et al., "Flagellin Promotes Myeloid Differentiation Factor 88-Dependent Development of Th2-Type Response," *The Journal of Immunology*, vol. 172:6922-6930 (2004).
Kühn, Ralf et al., "Interleukin-10-Deficient Mice Develop Chronic Enterocolitis," *Cell*, vol. 75:263-274 (1993).
Lindsay, J.O. et al., "Review article: The immunoregulatory cytokine interleukin-10—a therapy for Crohn's disease?" *Aliment Pharmacol. Ther.*, vol. 15:1709-1716 (2001).
McSorley, Stephen J. et al., "Bacterial Flagellin is an Effective Adjuvant for CD4+ T Cells In Vivo," *The Journal of Immunology*, vol. 169:3914-3919 (2002).
Means, Terry K. et al., "The Toll-Like Receptor 5 Stimulus Bacterial Flagellin Induces Maturation and Chemokine Production in Human Dendritic Cells," *The Journal of Immunology*, vol. 170:5165-5175 (2003).
Neville, Lewis F. et al., "Antibodies raised against N'-terminal *Pseudomonas aeruginosa* flagellin prevent mortality in lethal murine models of infection," *International Journal of Molecular Medicine*, vol. 16:165-171 (2005).
Schoepfer, Alain M. et al., "Phenotypic Associations of Crohn's Disease with Antibodies to Flagellins A4-Fla2 and Fla-X, ASCA, p-ANCA, PAB, and NOD2 Mutations in a Swiss Cohort," *Inflamm. Bowel Dis.*, retrieved online at http://www3.interscience.wiley.com/journal/122221849/abstract?CRETRY=1&SRETRY=0 (2009).
deVries, N. et al., "Production of Monoclonal Antibodies Specific for the *i* and *1,2* Flagellar Antigens of *Salmonella typhimurium* and Characterization of Their Respective Epitopes," *Applied and Environmental Microbiology*, vol. 64(12):5033-5038 (1998).
Matsumoto, Tetsuya et al., "Effect of Antiflagellar Human Monoclonal Antibody on Gut-Derived *Pseudomonas aeruginosa* Sepsis in Mice," *Clinical and Diagnostic Laboratory Immunology*, vol. 6(4):537-541 (1999).
UniProt, "Anti-MOG Z12 variable light chain," retrieved online at http://www.uniprot.org/uniprot/Q8VDD0, (2009).
International Search Report for Application No. PCT/US08/75383, dated Mar. 2, 2009.

(Continued)

*Primary Examiner* — Albert Navarro
*Assistant Examiner* — Ja'na Hines
(74) *Attorney, Agent, or Firm* — Nelson Mullins Riley Scarborough LLP; Jane E. Remillard, Esq.; Jill Gorny Sloper, Esq.

(57) ABSTRACT

The present invention provides a novel class of monoclonal antibodies which have a high affinity, broad spectrum neutralizing reactivity to flagellin from various Gram-negative bacteria including, but not limited to, *E. coli, Salmonella, Serratia, Proteus, Enterobacter, Citrobacter, Campylobacter* and *Pseudomonas*. The present invention further provides methods of treating inflammatory bowel disease (IBD) and methods of treating enterobacterial infections using anti-flagellin antibodies in humans, other animals and birds.

15 Claims, 46 Drawing Sheets

OTHER PUBLICATIONS

Eaves-Pyles, Tonyia et al., "Flagellin, a Novel Mediator of *Salmonella*-Induced Epithelial Activation and Systemic Inflammation: IκBα Degradation, Induction of Nitric Oxide Synthase, Induction of Proinflammatory Mediators, and Cardiovascular Dysfunction," *The Journal of Immunology*, vol. 166:1248-1260 (2001).

Evgenov, Oleg V. et al., "Neutralization of flagellin by active immunization or by monoclonal antibodies exerts protective effects in murine pneumonia models," Poster Presentation (2003).

Gewirtz, Andrew T. et al., "Dominant-negative TLR5 polymorphism reduces adaptive immune response to flagellin and negatively associates with Crohn's disease," *Am. J. Physiol. Gastrointest. Liver Physiol.*, vol. 290:G1157-G1163 (2006).

Gewirtz, Andrew T., "Flag in the crossroads: flagellin modulates innate and adaptive immunity," *Current Opinion in Gastroenterology*, vol. 22:8-12 (2006).

Gewirtz, Andrew T. et al., "*Salmonella* typhimurium translocates flagellin across intestinal epithelia, inducing a proinflammatory response," *The Journal of Clinical Investigation*, vol. 107(1):99-109 (2001).

Gewirtz, Andrew T., "TLRs in the Gut. III. Immune responses to flagellin in Crohn's disease: good, bad, or irrelevant?" *Am. J. Physiol. Gastrointest. Liver Physiol.*, vol. 292:G706-G710 (2007).

Hawn, Thomas R. et al., "A Common Dominant TLR5 Stop Codon Polymorphism Abolishes Flagellin Signaling and is Associated with Susceptibility to Legionnaires' Disease," *J. Exp. Med.*, vol. 198(10):1563-1572 (2003).

Hawn, Thomas R. et al., "A stop codon polymorphism of Toll-like receptor 5 is associated with resistance to systemic lupus erythematosus," *PNAS*, vol. 102(30):10593-10597 (2005).

Liaudet, Lucas et al., "Comparison of Inflammation, Organ Damage, and Oxidant Stress Induced by *Salmonella enterica* Serovar Muenchen Flagellin and Serovar Enteritidis Lipopolysaccharide," *Infection and Immunity*, vol. 70(1):192-198 (2002).

Liaudet, Lucas et al., "Flagellin from Gram-Negative Bacteria is a Potent Mediator of Acute Pulmonary Inflammation in Sepsis," *Shock*, vol. 19(2):131-137 (2003).

Liaudet, Lucas et al., "The Flagellin—TLR5 Axis: Therapeutic Opportunities," *Drug News Perspect*, vol. 15(7):1-13 (2002).

Lodes, Michael J. et al., "Bacterial flagellin is a dominant antigen in Crohn disease," *The Journal of Clinical Investigation*, vol. 113(9):1296-1306 (2004).

Marx, Jean, "Puzzling Out the Pains in the Gut," *Science*, vol. 315:33-35 (2007).

Murthy, Kanneganti G.K. et al., "Identification of Conserved Domains in *Salmonella muenchen* Flagellin That are Essential for its Ability to Activate TLR5 and to Induce an Inflammatory Response in Vitro," *The Journal of Biological Chemistry*, vol. 279(7):5667-5675 (2004).

Neish, Andrew S., "TLR5 in the Gut. II. Flagellin-induced inflammation and antiapoptosis," *Am. J. Physiol. Gastrointest. Liver Physiol.*, vol. 292:G462-G466 (2007).

Sitaraman, Shanthi V. et al., "Elevated flagellin-specific immunoglobulins in Crohn's disease," *Am. J. Physiol. Gastrointest. Liver Physiol.*, vol. 288:G403-G406 (2005).

Steiner, Theodore S., "How Flagellin and Toll-Like Receptor 5 Contribute to Enteric Infection," *Infection and Immunity*, vol. 75(2):545-552 (2007).

Szabó, Csaba, "Role of flagellin in the pathogenesis of shock and acute respiratory distress syndrome: Therapeutic opportunities," *Crit. Care. Med.*, vol. 31(1 Suppl.):S39-S45 (2003).

De Groeve, Kurt et al., "Nanobodies as Tools for In Vivo Imaging of Specific Immune Cell Types," J. Nucl. Med., vol. 51:782-789 (2010).

Holt, Lucy J. et al., "Domain antibodies: proteins for therapy," Trends in Biotechnology, vol. 21(11):484-490 (2003).

Mariuzza, R.A. et al., "The Structural Basis of Antigen-antibody Recognition," Ann. Rev. Biophys. Biophys. Chem., vol. 16:139-159 (1987).

Portolano, Stefano et al., "Lack of Promiscuity in Autoantigen-Specific H and L Chain Combinations as Revealed by Human H and L Chain 'Roulette'," The Journal of Immunology, vol. 150(3):880-887 (1993).

Silverman, Joshua et al., "Multivalent avimer proteins evolved by exon shuffling of a family of human receptor domains," Nature Biotechnology, vol. 23(12):1556-1561 (2005).

Wikman, M. et al., "Selection and characterization of HER2/neu-binding affibody ligands," Protein Engineering Design & Selection, vol. 17(5):455-462 (2004).

Winkler, Karsten et al., "Changing the Antigen Binding Specificity by Single Point Mutations of an Anti-p24 (HIV-1) Antibody," The Journal of Immunology, vol. 165:4505-4514 (2000).

\* cited by examiner

Fig. 1

741 Heavy Chain Sequences

```
         10         20         30         40         50         60         70         80         90        100
CAGGTTCAACTGCAGCAGTCTGGGGCTGAGCTGGTGGGGCCTGGGGCCTCAGTGACGCTGTCCTGCAAGGCTTCGGGCCACACATTTACTGACTATGAGA
 Q  V  Q  L  Q  Q  S  G  A  E  L  V  G  P  G  A  S  V  T  L  S  C  K  A  S  G  H  T  F  T  D  Y  E
                         10                            20                          CDR 1  30
```

```
        110        120        130        140        150        160        170        180        190        200
TGCACTGGGTGAAGCAGAGACACCTGTGCATGCCTGGAATGCTGGAGTATTGATCCTGAAACTGGTGGTACTGCTACAATCAGAAGCTCAAGGGGCGA
 M  H  W  V  K  Q  T  P  V  H  G  L  E  W  I  G  G  I  D  P  E  T  G  G  T  A  Y  N  Q  K  L  K  G  E
                40                              50  52 A                           60
                                           ─────────────CDR 2─────────────
```

```
        210        220        230        240        250        260        270        280        290        300
GGCCACACTGACTGCAGACAAATCCTCCAACAGCTACATGGAGCTCCGCAGCCTGACACTGAGGACTCTGAGGACTCTGAGGACTCTGACTGTATTACTGTACGATTACTT
 A  T  L  T  A  D  K  S  S  N  T  A  Y  M  E  L  R  S  L  T  S  E  D  S  A  V  Y  Y  C  T  I  Y  L
              70                       80  82 A B C                        90              96
                                                                                        ───CDR 3───
```

```
        310        320        330        340
GACTACTGGGGCCGAGGCACCACTCTCACAGTCTCCTCA
 D  Y  W  G  R  G  T  T  L  T  V  S  S
                       110
 102
───CDR 3───
```

CDR definitions and protein sequence numbering according to Kabat. CDR nucleotide and protein sequences are highlighted in bold typeface.

741 Light Chain Sequences

```
         10         20         30         40         50         60         70         80         90        100
                                                                            ├─────────── CDR 1 ──────────┤
CAAATTGTCTCCACCAGTCTCCAGCAATCATGTCTGCATCTCCAGGGAGAAGGTCACCATGACCTGCAGTGCCAACTCAAGTATAAATTACATGCACT
 Q  I  V  L  T  Q  S  P  A  I  M  S  A  S  P  G  E  K  V  T  M  T  C  S  A  N  S  S  I  N  Y  M  H
                               10                      20                      30

110        120        130        140        150        160        170        180        190        200
                                              ├──────── CDR 2 ────────┤
GGTACCAGCAGAAGCCAGGCACCTCCCCCAAAAGATGGATTTATGACACAACCATACTGGCTTCTGGAGTCCCTGCTCGCTTCAGTGGCAGTGGGTCTGG
 W  Y  Q  Q  K  P  G  T  S  P  K  R  W  I  Y  D  T  T  I  L  A  S  G  V  P  A  R  F  S  G  S  G  S  G
              40                      50                      60

210        220        230        240        250        260        270        280        290        300
                                                                   ├────────── CDR 3 ──────────┤
GACCTCTTATTCTCACAATCAGCAGCATGGAGGCTGAAGATGCTGCCACTTATTACTGCCATCAGCGGAGTAGTTACCCATTCACGTTCGGCTCGGGG
 T  S  Y  S  L  T  I  S  S  M  E  A  E  D  A  A  T  Y  Y  C  H  Q  R  S  S  Y  P  F  T  F  G  S  G
           70                      80                      90                        100

310
ACAAAGTTGGAAATAAAA
 T  K  L  E  I  K
    106A
```

CDR definitions and protein sequence numbering according to Kabat. CDR nucleotide and protein sequences are highlighted in bold typeface.

763 Heavy Chain Sequences

```
         10         20         30         40         50         60         70         80         90        100
GAGGTGCAGCTGTTGGAGTCTGGGGGAGGCTTGGTACAGCCTGGGGGGTCCCTGAGACTCTCCTGTGCAGCCTCTGGATTCACCTTTAGCAGCTATGCCA
 E  V  Q  L  L  E  S  G  G  A  L  V  Q  P  G  G  S  L  R  L  S  C  A  A  S  G  F  T  F  S  S  Y  A
                                                                                            └─ CDR 1 ──
                      10                                      20                                30

110        120        130        140        150        160        170        180        190        200
TGAGCTGGGTCCGCCAGGCTCCAGGTAAGGGGCTGGAGTGGCTCTCAGGTATTAGTGGTAGTGCTGATAACACATACTACGCAGAGTCGTGAAGGGCCG
 M  S  W  A  R  Q  A  P  G  K  G  L  E  W  L  S  G  I  S  G  S  A  D  N  T  Y  Y  A  E  S  V  K  G  R
─ CDR 1 ┘                 40             └──────────── CDR 2 ────────────────────
                                             50  52 A                           60

210        220        230        240        250        260        270        280        290        300
GTTCACCACCTCCAGAGACAATTCCATGAACATGTTGTATCTGCAAATGAACAGCCTGAGAGACGAGGACACGGCCTTTATTATTGTGCCAAAGGGGAC
 F  T  T  S  R  D  N  S  M  N  M  L  Y  L  Q  M  N  S  L  R  D  E  D  T  A  F  Y  Y  C  A  K  G  D
                       70                       80  82 A B C                       90       └─ CDR 3 ──

310        320        330        340        350
CAGGATCGGGGGACCCCTTGAATTCTGGGGCCAGGGAACCCTGGTCACCGTCTCCTCA
 Q  D  R  G  P  L  E  F  W  G  Q  G  T  L  V  T  V  S  S
─── CDR 3 ┘
          100A B                                110
```

CDR definitions and protein sequence numbering according to Kabat. CDR nucleotide and protein sequences are highlighted bold typeface

Fig. 4

763 Light Chain Sequences

```
         10         20         30         40         50         60         70         80         90        100
TCCTATGAGCTGACTCAGCCACCCTCGGTGTCAGTGTCCCCAGGACAGACGGCCAGAATCACCTGCTCTGGAGATGCATTGCCAAAGCAGTATGCTTATT
 S  Y  E  L  T  Q  P  P  S  V  S  V  S  P  G  Q  T  A  R  I  T  C  S  G  D  A  L  P  K  Q  Y  A  Y
                                                   11                       20                       30
                                                                                  └─────── CDR 1 ──────
```

```
        110        120        130        140        150        160        170        180        190        200
GGTACCAGCAGAAGCCAGGCCAGGCCCCTGTGTTGTTGATATATCAAGACACTAAGAGGCCCTCAGGGATCCCTGAGCGATTTCTGGCTCCAGCTCAGG
 W  Y  Q  Q  K  P  G  Q  A  P  V  L  L  I  Y  Q  D  T  K  R  P  S  G  I  P  E  R  F  S  G  S  S  S  G
────┘       40                              └── CDR 2 ──┘  50                              60
```

```
        210        220        230        240        250        260        270        280        290        300
GACAACAGTCGCTTGACCATCAGTGGAGTCCAGGCAGAGGACGAGGCTGACTATTACTGTCAATCAGCAGACAGCAATGATAGTTATTATGTCTTCGGA
 T  T  V  A  L  T  I  S  G  V  Q  A  E  D  E  A  D  Y  Y  C  Q  S  A  D  S  N  D  S  Y  Y  V  F  G
 70                              80                              90        └────── CDR 3 ──────
                                                                              95 A B
```

```
        310
ACTGGGACCAAGGTCACCGTCCTG
 T  G  T  K  V  T  V  L
100                 106A
```

CDR definitions and protein sequence numbering according to Kabat. CDR nucleotide and protein sequences are highlighted in bold typeface a: sham + vehicle
b: DNBS + vehicle
c-c2: DNBS + INO-763 (20 mg/kg)
d,d1: DNBS + Infliximab (5 mg/kg)
e-e1: DNBS + CBH2 (20 mg/kg)

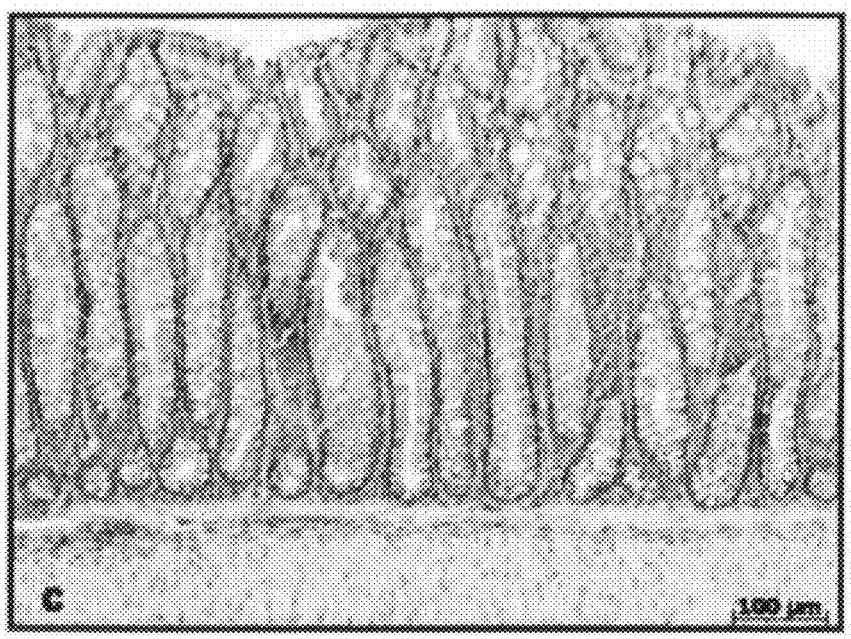
*Fig. 7*

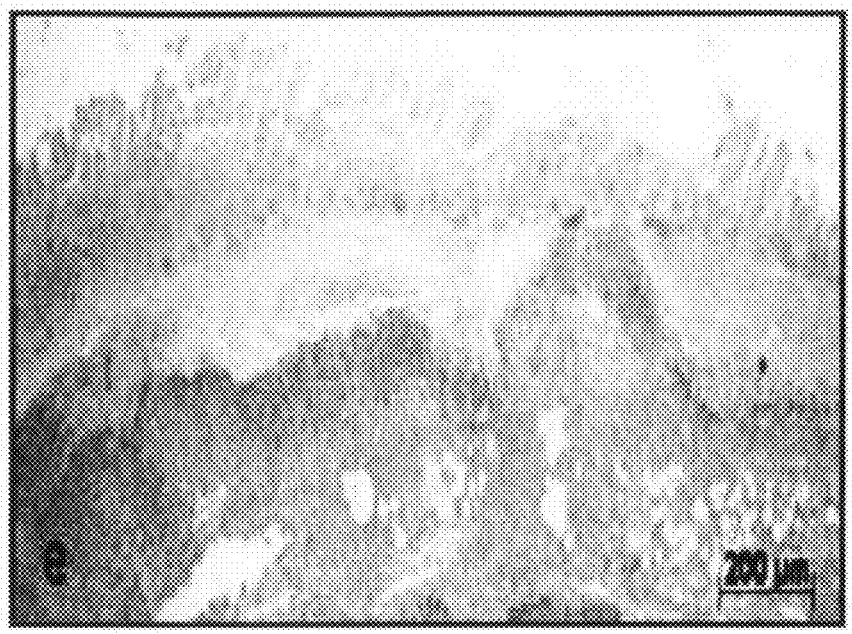
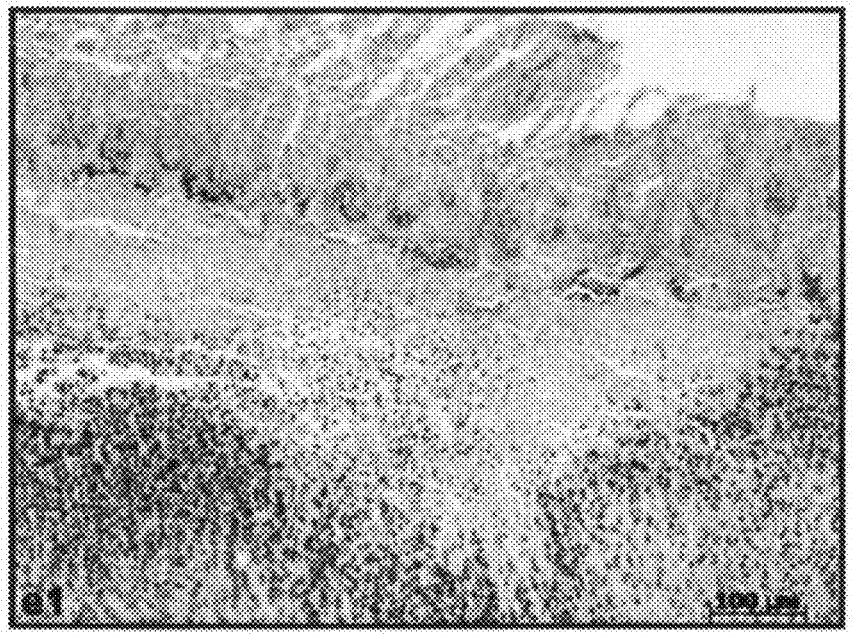
*Fig. 7*

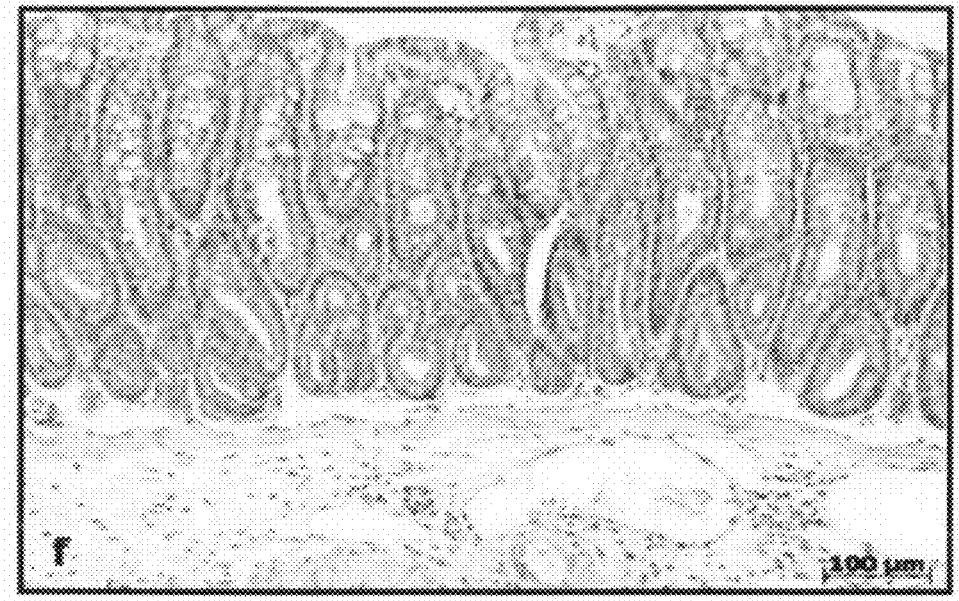
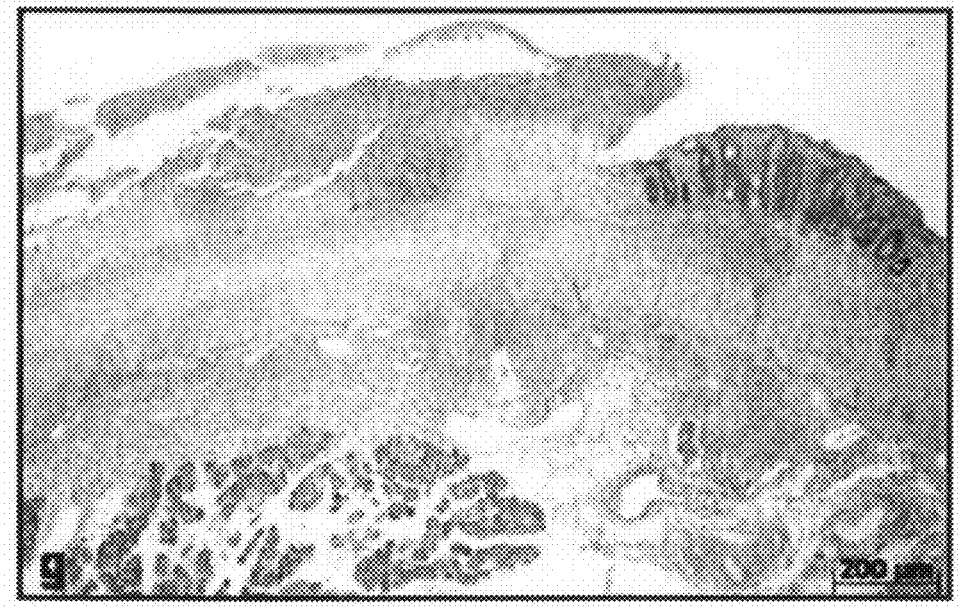
Fig. 11

Comparison of INO 763 vs. Infliximab on
DNBS-induced mediator production from colon extracts

| Monoclonal Antibody | DNBS | MDA (mM/mg wet tissue) | IL-1b (pg/100 mg) | TNFa (pg/100 mg) | MIP-1 (pg/mg) | MIP-2 (pg/mg) | IL-8 (pg/100 mg) |
|---|---|---|---|---|---|---|---|
| saline | no | 26.00 ± 1.58 | 34.40 ± 4.56 | 26.20 ± 2.88 | 19.40 ± 1.80 | 16.00 ± 1.22 | 46.60 ± 2.24 |
| saline | yes | 153.00 ± 6.74 | 195.80 ± 23.94 | 131.80 ± 15.60 | 104.60 ± 7.06 | 146.00 ± 17.20 | 143.40 ± 3.17 |
| mAb 763 (10 mg/kg) | yes | 89.80 ± 8.07 | 116.60 ± 7.41 | 62.80 ± 14.36 | 61.80 ± 4.29 | 57.60 ± 5.52 | 87.20 ± 3.67 |
| mAb 763 (20 mg/kg) | yes | 41.40 ± 3.17 | 73.20 ± 4.58 | 46.20 ± 8.51 | 38.00 ± 3.64 | 25.40 ± 8.42 | 69.60 ± 3.61 |
| CBH2 (10 mg/kg) | yes | 153.00 ± 2.98 | 205.00 ± 11.82 | 125.20 ± 8.35 | 106.40 ± 4.46 | 137.80 ± 4.30 | 138.40 ± 1.36 |
| CBH2 (20 mg/kg) | yes | 152.20 ± 4.28 | 202.8 ± 17.04 | 119.80 ± 11.82 | 105.00 ± 4.88 | 145.20 ± 5.09 | 138.20 ± 1.42 |
| Infliximab (5 mg/kg) | yes | 59.00 ± 7.64 | 80.80 ± 10.62 | 20.80 ± 4.21 | 47 ± 2.34 | 16.60 ± 2.48 | 63.80 ± 1.82 |

Fig. 19

```
                        SEQUENCE LISTING

<160> NUMBER OF SEQ ID NOS: 41

<210> SEQ ID NO 1
<211> LENGTH: 113
<212> TYPE: PRT
<213> ORGANISM: Mus sp.

<400> SEQUENCE: 1

Gln Val Gln Leu Gln Gln Ser Gly Ala Glu Leu Val Gly Pro Gly Ala
1               5                   10                  15

Ser Val Thr Leu Ser Cys Lys Ala Ser Gly His Thr Phe Thr Asp Tyr
                20                  25                  30

Glu Met His Trp Val Lys Gln Thr Pro Val His Gly Leu Glu Trp Ile
            35                  40                  45

Gly Gly Ile Asp Pro Glu Thr Gly Gly Thr Ala Tyr Asn Gln Lys Leu
        50                  55                  60

Lys Gly Glu Ala Thr Leu Thr Ala Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Thr Ile Tyr Leu Asp Tyr Trp Gly Arg Gly Thr Thr Leu Thr Val Ser
                100                 105                 110

Ser

<210> SEQ ID NO 2
<211> LENGTH: 119
<212> TYPE: PRT
<213> ORGANISM: Homo sapiens
```

<400> SEQUENCE: 2

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ala Arg Gln Ala Pro Gly Lys Gly Leu Glu Trp Leu
        35                  40                  45

Ser Gly Ile Ser Gly Ser Ala Asp Asn Thr Tyr Tyr Ala Glu Ser Val
    50                  55                  60

Lys Gly Arg Phe Thr Thr Ser Arg Asp Asn Ser Met Asn Met Leu Tyr
65                  70                  75                  80

Leu Gln Met Asn Ser Leu Arg Asp Glu Asp Thr Ala Phe Tyr Tyr Cys
                85                  90                  95

Ala Lys Gly Asp Gln Asp Arg Gly Pro Leu Glu Phe Trp Gly Gln Gly
            100                 105                 110

Thr Leu Val Thr Val Ser Ser
        115

<210> SEQ ID NO 3
<211> LENGTH: 106
<212> TYPE: PRT
<213> ORGANISM: Mus sp.

<400> SEQUENCE: 3

Gln Ile Val Leu Thr Gln Ser Pro Ala Ile Met Ser Ala Ser Pro Gly
1               5                   10                  15

Glu Lys Val Thr Met Thr Cys Ser Ala Asn Ser Ser Ile Asn Tyr Met
            20                  25                  30

His Trp Tyr Gln Gln Lys Pro Gly Thr Ser Pro Lys Arg Trp Ile Tyr
        35                  40                  45

Asp Thr Thr Ile Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Pro Phe Thr
                85                  90                  95

Phe Gly Ser Gly Thr Lys Leu Glu Ile Lys
            100                 105

<210> SEQ ID NO 4
<211> LENGTH: 108
<212> TYPE: PRT
<213> ORGANISM: Homo sapiens

<400> SEQUENCE: 4

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Leu Ile Tyr
        35                  40                  45

Gln Asp Thr Lys Arg Pro Ser Gly Ile Pro Glu Arg Phe Ser Gly Ser
    50                  55                  60

Ser Ser Gly Thr Thr Val Ala Leu Thr Ile Ser Gly Val Gln Ala Glu
65                  70                  75                  80

```
Asp Glu Ala Asp Tyr Tyr Cys Gln Ser Ala Asp Ser Asn Asp Ser Tyr
                85                  90                  95
Tyr Val Phe Gly Thr Gly Thr Lys Val Thr Val Leu
            100                 105

<210> SEQ ID NO 5
<211> LENGTH: 5
<212> TYPE: PRT
<213> ORGANISM: Mus sp.

<400> SEQUENCE: 5

Asp Tyr Glu Met His
1               5

<210> SEQ ID NO 6
<211> LENGTH: 5
<212> TYPE: PRT
<213> ORGANISM: Homo sapiens

<400> SEQUENCE: 6

Ser Tyr Ala Met Ser
1               5

<210> SEQ ID NO 7
<211> LENGTH: 17
<212> TYPE: PRT
<213> ORGANISM: Mus sp.

<400> SEQUENCE: 7

Gly Ile Asp Pro Glu Thr Gly Gly Thr Ala Tyr Asn Gln Lys Leu Lys
1               5                   10                  15
Gly

<210> SEQ ID NO 8
<211> LENGTH: 17
<212> TYPE: PRT
<213> ORGANISM: Homo sapiens

<400> SEQUENCE: 8

Gly Ile Ser Gly Ser Ala Asp Asn Thr Tyr Tyr Ala Glu Ser Val Lys
1               5                   10                  15
Gly

<210> SEQ ID NO 9
<211> LENGTH: 4
<212> TYPE: PRT
<213> ORGANISM: Mus sp.

<400> SEQUENCE: 9

Tyr Leu Asp Tyr
1

<210> SEQ ID NO 10
<211> LENGTH: 10
<212> TYPE: PRT
<213> ORGANISM: Homo sapiens

<400> SEQUENCE: 10

Gly Asp Gln Asp Arg Gly Pro Leu Glu Phe
1               5                   10
```

```
<210> SEQ ID NO 11
<211> LENGTH: 10
<212> TYPE: PRT
<213> ORGANISM: Mus sp.

<400> SEQUENCE: 11

Ser Ala Asn Ser Ser Ile Asn Tyr Met His
1               5                   10

<210> SEQ ID NO 12
<211> LENGTH: 11
<212> TYPE: PRT
<213> ORGANISM: Homo sapiens

<400> SEQUENCE: 12

Ser Gly Asp Ala Leu Pro Lys Gln Tyr Ala Tyr
1               5                   10

<210> SEQ ID NO 13
<211> LENGTH: 7
<212> TYPE: PRT
<213> ORGANISM: Mus sp.

<400> SEQUENCE: 13

Asp Thr Thr Ile Leu Ala Ser
1               5

<210> SEQ ID NO 14
<211> LENGTH: 7
<212> TYPE: PRT
<213> ORGANISM: Homo sapiens

<400> SEQUENCE: 14

Gln Asp Thr Lys Arg Pro Ser
1               5

<210> SEQ ID NO 15
<211> LENGTH: 9
<212> TYPE: PRT
<213> ORGANISM: Mus sp.

<400> SEQUENCE: 15

His Gln Arg Ser Ser Tyr Pro Phe Thr
1               5

<210> SEQ ID NO 16
<211> LENGTH: 11
<212> TYPE: PRT
<213> ORGANISM: Homo sapiens

<400> SEQUENCE: 16

Gln Ser Ala Asp Ser Asn Asp Ser Tyr Tyr Val
1               5                   10

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgcggatccc aatggcacaa gtcattaata caaaca                            36
```

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
tccgctcgag ttaaatagtt tcaccgtcgt tggcacc        37

<210> SEQ ID NO 19
<211> LENGTH: 339
<212> TYPE: DNA
<213> ORGANISM: Mus sp.
<220> FEATURE:
<221> NAME/KEY: CDS
<222> LOCATION: (1)..(339)

<400> SEQUENCE: 19

```
cag gtt caa ctg cag cag tct ggg gct gag ctg gtg ggg cct ggg gct      48
Gln Val Gln Leu Gln Gln Ser Gly Ala Glu Leu Val Gly Pro Gly Ala
1               5                   10                  15 tca gtg acg ctg tcc tgc aag gct tcg ggc cac aca ttt act gac tat      96
Ser Val Thr Leu Ser Cys Lys Ala Ser Gly His Thr Phe Thr Asp Tyr
            20                  25                  30 gag atg cac tgg gtg aag cag aca cct gtg cat ggc ctg gaa tgg att     144
Glu Met His Trp Val Lys Gln Thr Pro Val His Gly Leu Glu Trp Ile
        35                  40                  45 gga ggt att gat cct gaa act ggt ggt act gcc tac aat cag aag ctc     192
Gly Gly Ile Asp Pro Glu Thr Gly Gly Thr Ala Tyr Asn Gln Lys Leu
    50                  55                  60 aag ggc gag gcc aca ctg act gca gac aaa tcc tcc aac aca gcc tac     240
Lys Gly Glu Ala Thr Leu Thr Ala Asp Lys Ser Ser Asn Thr Ala Tyr
65                  70                  75                  80 atg gag ctc cgc agc ctg aca tct gag gac tct gcc gtc tat tac tgt     288
Met Glu Leu Arg Ser Leu Thr Ser Glu Asp Ser Ala Val Tyr Tyr Cys
                85                  90                  95 acg att tac ctt gac tac tgg ggc cga ggc acc act ctc aca gtc tcc     336
Thr Ile Tyr Leu Asp Tyr Trp Gly Arg Gly Thr Thr Leu Thr Val Ser
            100                 105                 110 tca                                                                  339
Ser
```

<210> SEQ ID NO 20
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 20

```
gag gtg cag ctg ttg gag tct ggg gga gcc ttg gta cag cct ggg ggg      48
Glu Val Gln Leu Leu Glu Ser Gly Gly Ala Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30 gcc atg agc tgg gcc cgc cag gct cca ggt aag ggg ctg gag tgg ctc     144
Ala Met Ser Trp Ala Arg Gln Ala Pro Gly Lys Gly Leu Glu Trp Leu
        35                  40                  45 tca ggt att agt ggt agt gct gat aac aca tac tac gca gag tcc gtg     192
Ser Gly Ile Ser Gly Ser Ala Asp Asn Thr Tyr Tyr Ala Glu Ser Val
    50                  55                  60
```

```
aag ggc cgg ttc acc acc tcc aga gac aat tcc atg aac atg ttg tat      240
Lys Gly Arg Phe Thr Thr Ser Arg Asp Asn Ser Met Asn Met Leu Tyr
 65                  70                  75                  80 ctg caa atg aac agc ctg aga gac gag gac acg gcc ttt tat tat tgt      288
Leu Gln Met Asn Ser Leu Arg Asp Glu Asp Thr Ala Phe Tyr Tyr Cys
                 85                  90                  95 gcc aaa ggc gac cag gat cgg gga ccc ctt gaa ttc tgg ggc cag gga      336
Ala Lys Gly Asp Gln Asp Arg Gly Pro Leu Glu Phe Trp Gly Gln Gly
            100                 105                 110 acc ctg gtc acc gtc tcc tca                                          357
Thr Leu Val Thr Val Ser Ser
            115

<210> SEQ ID NO 21
<211> LENGTH: 318
<212> TYPE: DNA
<213> ORGANISM: Mus sp.
<220> FEATURE:
<221> NAME/KEY: CDS
<222> LOCATION: (1)..(318)

<400> SEQUENCE: 21 caa att gtt ctc acc cag tct cca gca atc atg tct gca tct cca ggg       48
Gln Ile Val Leu Thr Gln Ser Pro Ala Ile Met Ser Ala Ser Pro Gly
  1               5                  10                  15 gag aag gtc acc atg acc tgc agt gcc aac tca agt ata aat tac atg       96
Glu Lys Val Thr Met Thr Cys Ser Ala Asn Ser Ser Ile Asn Tyr Met
             20                  25                  30 cac tgg tac cag cag aag cca ggc acc tcc ccc aaa aga tgg att tat      144
His Trp Tyr Gln Gln Lys Pro Gly Thr Ser Pro Lys Arg Trp Ile Tyr
         35                  40                  45 gac aca acc ata ctg gct tct gga gtc cct gct cgc ttc agt ggc agt      192
Asp Thr Thr Ile Leu Ala Ser Gly Val Pro Ala Arg Phe Ser Gly Ser
     50                  55                  60 ggg tct ggg acc tct tat tct ctc aca atc agc agc atg gag gct gaa      240
Gly Ser Gly Thr Ser Tyr Ser Leu Thr Ile Ser Ser Met Glu Ala Glu
 65                  70                  75                  80 gat gct gcc act tat tac tgc cat cag cgg agt agt tac cca ttc acg      288
Asp Ala Ala Thr Tyr Tyr Cys His Gln Arg Ser Ser Tyr Pro Phe Thr
                 85                  90                  95 ttc ggc tcg ggg aca aag ttg gaa ata aaa                              318
Phe Gly Ser Gly Thr Lys Leu Glu Ile Lys
            100                 105

<210> SEQ ID NO 22
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 22 tcc tat gag ctg aca cag cca ccc tcg gtg tca gtg tcc cca gga cag       48
Ser Tyr Glu Leu Thr Gln Pro Pro Ser Val Ser Val Ser Pro Gly Gln
  1               5                  10                  15 acg gcc aga atc acc tgc tct gga gat gca ttg cca aag cag tat gct       96
Thr Ala Arg Ile Thr Cys Ser Gly Asp Ala Leu Pro Lys Gln Tyr Ala
             20                  25                  30 tat tgg tac cag cag aag cca ggc cag gcc cct gtg ttg ttg ata tat      144
Tyr Trp Tyr Gln Gln Lys Pro Gly Gln Ala Pro Val Leu Leu Ile Tyr
         35                  40                  45
```

```
caa gac act aag agg ccc tca ggg atc cct gag cga ttt tct ggc tcc      192
Gln Asp Thr Lys Arg Pro Ser Gly Ile Pro Glu Arg Phe Ser Gly Ser
 50                  55                  60 agc tca ggg aca aca gtc gcg ttg acc atc agt gga gtc cag gca gag      240
Ser Ser Gly Thr Thr Val Ala Leu Thr Ile Ser Gly Val Gln Ala Glu
 65                  70                  75                  80 gac gag gct gac tat tac tgt caa tca gca gac agc aat gat agt tat      288
Asp Glu Ala Asp Tyr Tyr Cys Gln Ser Ala Asp Ser Asn Asp Ser Tyr
                 85                  90                  95 tat gtc ttc gga act ggg acc aag gtc acc gtc ctg                      324
Tyr Val Phe Gly Thr Gly Thr Lys Val Thr Val Leu
                100                 105

<210> SEQ ID NO 23
<211> LENGTH: 15
<212> TYPE: DNA
<213> ORGANISM: Mus sp.
<220> FEATURE:
<221> NAME/KEY: CDS
<222> LOCATION: (1)..(15)

<400> SEQUENCE: 23 gac tat gag atg cac                                                   15
Asp Tyr Glu Met His
 1               5

<210> SEQ ID NO 24
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 24 agc tat gcc atg agc                                                   15
Ser Tyr Ala Met Ser
 1               5

<210> SEQ ID NO 25
<211> LENGTH: 51
<212> TYPE: DNA
<213> ORGANISM: Mus sp.
<220> FEATURE:
<221> NAME/KEY: CDS
<222> LOCATION: (1)..(51)

<400> SEQUENCE: 25 ggt att gat cct gaa act ggt ggt act gcc tac aat cag aag ctc aag       48
Gly Ile Asp Pro Glu Thr Gly Gly Thr Ala Tyr Asn Gln Lys Leu Lys
 1               5                  10                  15 ggc                                                                   51
Gly

<210> SEQ ID NO 26
<211> LENGTH: 51
<212> TYPE: DNA
<213> ORGANISM: Homo sapiens
<220> FEATURE:
<221> NAME/KEY: CDS
<222> LOCATION: (1)..(51)
```

```
<400> SEQUENCE: 26 ggt att agt ggt agt gct gat aac aca tac tac gca gag tcc gtg aag        48
Gly Ile Ser Gly Ser Ala Asp Asn Thr Tyr Tyr Ala Glu Ser Val Lys
1               5                   10                  15 ggc                                                                    51
Gly

<210> SEQ ID NO 27
<211> LENGTH: 12
<212> TYPE: DNA
<213> ORGANISM: Mus sp.
<220> FEATURE:
<221> NAME/KEY: CDS
<222> LOCATION: (1)..(12)

<400> SEQUENCE: 27 tac ctt gac tac                                                        12
Tyr Leu Asp Tyr
1

<210> SEQ ID NO 28
<211> LENGTH: 30
<212> TYPE: DNA
<213> ORGANISM: Homo sapiens
<220> FEATURE:
<221> NAME/KEY: CDS
<222> LOCATION: (1)..(30)

<400> SEQUENCE: 28 ggc gac cag gat cgg gga ccc ctt gaa ttc                                30
Gly Asp Gln Asp Arg Gly Pro Leu Glu Phe
1               5                   10

<210> SEQ ID NO 29
<211> LENGTH: 30
<212> TYPE: DNA
<213> ORGANISM: Mus sp.
<220> FEATURE:
<221> NAME/KEY: CDS
<222> LOCATION: (1)..(30)

<400> SEQUENCE: 29 agt gcc aac tca agt ata aat tac atg cac                                30
Ser Ala Asn Ser Ser Ile Asn Tyr Met His
1               5                   10

<210> SEQ ID NO 30
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 30 tct gga gat gca ttg cca aag cag tat gct tat                            33
Ser Gly Asp Ala Leu Pro Lys Gln Tyr Ala Tyr
1               5                   10

<210> SEQ ID NO 31
<211> LENGTH: 21
<212> TYPE: DNA
<213> ORGANISM: Mus sp.
<220> FEATURE:
<221> NAME/KEY: CDS
<222> LOCATION: (1)..(21)
```

```
<400> SEQUENCE: 31 gac aca acc ata ctg gct tct                                        21
Asp Thr Thr Ile Leu Ala Ser
1               5

<210> SEQ ID NO 32
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 32 caa gac act aag agg ccc tca                                        21
Gln Asp Thr Lys Arg Pro Ser
1               5

<210> SEQ ID NO 33
<211> LENGTH: 27
<212> TYPE: DNA
<213> ORGANISM: Mus sp.
<220> FEATURE:
<221> NAME/KEY: CDS
<222> LOCATION: (1)..(27)

<400> SEQUENCE: 33 cat cag cgg agt agt tac cca ttc acg                                27
His Gln Arg Ser Ser Tyr Pro Phe Thr
1               5

<210> SEQ ID NO 34
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 34 caa tca gca gac agc aat gat agt tat tat gtc                        33
Gln Ser Ala Asp Ser Asn Asp Ser Tyr Tyr Val
1               5                   10

<210> SEQ ID NO 35
<211> LENGTH: 365
<212> TYPE: PRT
<213> ORGANISM: Proteus mirabilis

<400> SEQUENCE: 35

Met Ala Gln Val Ile Asn Thr Asn Tyr Leu Ser Leu Val Thr Gln Asn
1               5                   10                  15

Asn Leu Asn Lys Ser Gln Gly Thr Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Val Asn Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ala Lys Asn Gly Thr Asn Ser Asn Ser Asp Ile Thr Ser Ile
            100                 105                 110
```

```
Gln Asn Glu Val Lys Asn Val Leu Asp Glu Ile Asn Arg Ile Ser Glu
    115                 120                 125

Gln Thr Gln Phe Asn Gly Val Lys Val Leu Ser Gly Glu Lys Ser Glu
    130                 135                 140

Met Val Ile Gln Val Gly Thr Asn Asp Asn Glu Thr Ile Lys Phe Asn
145                 150                 155                 160

Leu Asp Lys Val Asp Asn Asp Thr Leu Gly Val Ala Ser Asp Lys Leu
                165                 170                 175

Phe Asp Thr Lys Thr Glu Lys Lys Gly Val Thr Ala Ala Gly Ala Gly
            180                 185                 190

Val Thr Asp Ala Lys Lys Ile Asn Ala Ala Thr Leu Asp Met Met
    195                 200                 205

Val Ser Leu Val Lys Glu Phe Asn Leu Asp Gly Lys Pro Val Thr Asp
210                 215                 220

Lys Phe Ile Val Thr Lys Gly Gly Lys Asp Tyr Val Ala Thr Lys Ser
225                 230                 235                 240

Asp Phe Glu Leu Asp Ala Thr Gly Thr Lys Leu Gly Leu Lys Ala Ser
                245                 250                 255

Ala Thr Thr Glu Phe Lys Val Asp Ala Gly Lys Asp Val Lys Thr Leu
            260                 265                 270

Asn Val Lys Asp Asp Ala Leu Ala Thr Leu Asp Lys Ala Ile Asn Thr
    275                 280                 285

Ile Asp Glu Ser Arg Ser Lys Leu Gly Ala Ile Gln Asn Arg Phe Glu
290                 295                 300

Ser Thr Ile Asn Asn Leu Asn Asn Thr Val Asn Asn Leu Ser Ala Ser
305                 310                 315                 320

Arg Ser Arg Ile Leu Asp Ala Asp Tyr Ala Thr Glu Val Ser Asn Met
                325                 330                 335

Ser Arg Gly Gln Ile Leu Gln Gln Ala Gly Thr Ser Val Leu Ala Gln
            340                 345                 350

Ala Asn Gln Val Pro Gln Thr Val Leu Ser Leu Leu Arg
    355                 360                 365

<210> SEQ ID NO 36
<211> LENGTH: 387
<212> TYPE: PRT
<213> ORGANISM: Pseudomonas aeruginosa

<400> SEQUENCE: 36

Met Ala Leu Thr Val Asn Thr Asn Ile Ala Ser Leu Asn Thr Gln Arg
1               5                   10                  15

Asn Leu Asn Asn Ser Ser Ala Ser Leu Asn Thr Ser Leu Gln Arg Leu
                20                  25                  30

Ser Thr Gly Ser Arg Ile Asn Ser Ala Lys Asp Asp Ala Ala Gly Leu
            35                  40                  45

Gln Ile Ala Asn Arg Leu Thr Ser Gln Val Asn Gly Leu Asn Val Ala
    50                  55                  60

Thr Lys Asn Ala Asn Asp Gly Ile Ser Leu Ala Gln Thr Ala Glu Gly
65                  70                  75                  80

Ala Leu Gln Gln Ser Thr Asn Ile Leu Gln Arg Met Arg Asp Leu Ser
                85                  90                  95

Leu Gln Ser Ala Asn Gly Ser Asn Ser Asp Ser Glu Arg Thr Ala Leu
            100                 105                 110

Asn Gly Glu Val Lys Gln Leu Gln Lys Glu Leu Asp Arg Ile Ser Asn
    115                 120                 125
```

```
Thr Thr Thr Phe Gly Gly Arg Lys Leu Leu Asp Gly Ser Phe Gly Val
        130                 135                 140

Ala Ser Phe Gln Val Gly Ser Ala Ala Asn Glu Ile Ile Ser Val Gly
145                 150                 155                 160

Ile Asp Glu Met Ser Ala Glu Ser Leu Asn Gly Thr Tyr Phe Lys Ala
                165                 170                 175

Asp Gly Gly Gly Ala Val Thr Ala Ala Thr Ala Ser Gly Thr Val Asp
            180                 185                 190

Ile Ala Ile Gly Ile Thr Gly Ser Ala Val Asn Val Lys Val Asp
        195                 200                 205

Met Lys Gly Asn Glu Thr Ala Glu Gln Ala Ala Lys Ile Ala Ala
210                 215                 220

Ala Val Asn Asp Ala Asn Val Gly Ile Gly Ala Phe Thr Asp Gly Ala
225                 230                 235                 240

Gln Ile Ser Tyr Val Ser Lys Ala Ser Ala Asp Gly Thr Thr Ser Ala
                245                 250                 255

Val Ser Gly Val Ala Ile Thr Asp Thr Gly Ser Thr Gly Ala Gly Thr
            260                 265                 270

Ala Ala Gly Thr Thr Thr Phe Thr Glu Ala Asn Asp Thr Val Ala Lys
        275                 280                 285

Ile Asp Ile Ser Thr Ala Lys Gly Ala Gln Ser Ala Val Leu Val Ile
290                 295                 300

Asp Glu Ala Ile Lys Gln Ile Asp Ala Gln Arg Ala Asp Leu Gly Ala
305                 310                 315                 320

Val Gln Asn Arg Phe Asp Asn Thr Ile Asn Asn Leu Lys Asn Ile Gly
                325                 330                 335

Glu Asn Val Ser Ala Ala Arg Gly Arg Ile Glu Asp Thr Asp Phe Ala
            340                 345                 350

Ala Glu Thr Ala Asn Leu Thr Lys Asn Gln Val Leu Gln Gln Ala Gly
        355                 360                 365

Thr Ala Ile Leu Ala Gln Ala Asn Gln Leu Pro Gln Ser Val Leu Ser
370                 375                 380

Leu Leu Arg
385

<210> SEQ ID NO 37
<211> LENGTH: 585
<212> TYPE: PRT
<213> ORGANISM: Escherichia coli

<400> SEQUENCE: 37

Met Ala Gln Val Ile Asn Thr Asn Ser Leu Ser Leu Ile Thr Gln Asn
1               5                   10                  15

Asn Leu Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
50                  55                  60

Ala Arg Asn Ala Asn Asp Gly Ile Ser Val Ala Gln Thr Thr Glu Gly
65                  70                  75                  80

Ala Leu Ser Glu Ile Asn Asn Asn Leu Gln Arg Ile Arg Glu Leu Thr
                85                  90                  95

Val Gln Ala Thr Thr Gly Thr Asn Ser Asp Ser Asp Leu Asp Ser Ile
            100                 105                 110
```

-continued

```
Gln Asp Glu Ile Lys Ser Arg Leu Asp Glu Ile Asp Arg Val Ser Gly
            115                 120                 125
Gln Thr Gln Phe Asn Gly Val Asn Val Leu Ala Lys Asp Gly Ser Met
        130                 135                 140
Lys Ile Gln Val Gly Ala Asn Asp Gly Glu Thr Ile Thr Ile Asp Leu
145                 150                 155                 160
Lys Lys Ile Asp Ser Asp Thr Leu Gly Leu Asn Gly Phe Asn Val Asn
                165                 170                 175
Gly Lys Gly Thr Ile Thr Asn Lys Ala Ala Thr Val Ser Asp Leu Thr
            180                 185                 190
Ser Ala Gly Ala Lys Leu Asn Thr Thr Gly Leu Tyr Asp Leu Lys
        195                 200                 205
Thr Glu Asn Thr Leu Leu Thr Thr Asp Ala Ala Phe Asp Lys Leu Gly
    210                 215                 220
Asn Gly Asp Lys Val Thr Val Gly Gly Val Asp Tyr Thr Tyr Asn Ala
225                 230                 235                 240
Lys Ser Gly Asp Phe Thr Thr Lys Ser Thr Ala Gly Thr Gly Val
                245                 250                 255
Asp Ala Ala Ala Gln Ala Ala Asp Ser Ala Ser Lys Arg Asp Ala Leu
            260                 265                 270
Ala Ala Thr Leu His Ala Asp Val Gly Lys Ser Val Asn Gly Ser Tyr
        275                 280                 285
Thr Thr Lys Asp Gly Thr Val Ser Phe Glu Thr Asp Ser Ala Gly Asn
    290                 295                 300
Ile Thr Ile Gly Gly Ser Gln Ala Tyr Val Asp Asp Ala Gly Asn Leu
305                 310                 315                 320
Thr Thr Asn Asn Ala Gly Ser Ala Ala Lys Ala Asp Met Lys Ala Leu
                325                 330                 335
Leu Lys Ala Ala Ser Glu Gly Ser Asp Gly Ala Ser Leu Thr Phe Asn
            340                 345                 350
Gly Thr Glu Tyr Thr Ile Ala Lys Ala Thr Pro Ala Thr Thr Pro
        355                 360                 365
Val Ala Pro Leu Ile Pro Gly Gly Ile Thr Tyr Gln Ala Thr Val Ser
    370                 375                 380
Lys Asp Val Val Leu Ser Glu Thr Lys Ala Ala Ala Thr Ser Ser
385                 390                 395                 400
Ile Thr Phe Asn Ser Gly Val Leu Ser Lys Thr Ile Gly Phe Thr Ala
                405                 410                 415
Gly Glu Ser Ser Asp Ala Ala Lys Ser Tyr Val Asp Lys Gly Gly
            420                 425                 430
Ile Thr Asn Val Ala Asp Tyr Thr Val Ser Tyr Ser Val Asn Lys Asp
        435                 440                 445
Asn Gly Ser Val Thr Val Ala Gly Tyr Ala Ser Ala Thr Asp Thr Asn
    450                 455                 460
Lys Asp Tyr Ala Pro Ala Ile Gly Thr Ala Val Asn Val Asn Ser Ala
465                 470                 475                 480
Gly Lys Ile Thr Thr Glu Thr Ser Ala Gly Ser Ala Thr Thr Asn
                485                 490                 495
Pro Leu Ala Ala Leu Asp Asp Ala Ile Ser Ser Ile Asp Lys Phe Arg
            500                 505                 510
Ser Ser Leu Gly Ala Ile Gln Asn Arg Leu Asp Ser Ala Val Thr Asn
        515                 520                 525
Leu Asn Asn Thr Thr Thr Asn Leu Ser Glu Ala Gln Ser Arg Ile Gln
    530                 535                 540
```

```
Asp Ala Asp Tyr Ala Thr Glu Val Ser Asn Met Ser Lys Ala Gln Ile
545                 550                 555                 560

Ile Gln Gln Ala Gly Asn Ser Val Leu Ala Lys Ala Asn Gln Val Pro
                565                 570                 575

Gln Gln Val Leu Ser Leu Leu Gln Gly
            580                 585

<210> SEQ ID NO 38
<211> LENGTH: 348
<212> TYPE: PRT
<213> ORGANISM: Serratia marcescens

<400> SEQUENCE: 38

Met Ala Gln Val Ile Asn Thr Asn Ser Leu Ser Leu Met Ala Gln Asn
1               5                   10                  15

Asn Leu Asn Lys Ser Gln Ser Ser Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ser Asp Arg Phe Thr Ala Asn Ile Lys Gly Leu Thr Gln Ala
    50                  55                  60

Ser Arg Asn Ala Asn Asp Gly Ile Ser Leu Ala Gln Thr Thr Glu Gly
65                  70                  75                  80

Ala Leu Asn Glu Val Asn Asp Asn Leu Gln Asn Ile Arg Arg Leu Thr
                85                  90                  95

Val Gln Ala Gln Asn Gly Ser Asn Ser Thr Ser Asp Leu Lys Ser Ile
            100                 105                 110

Gln Asp Glu Ile Thr Gln Arg Met Ser Glu Ile Asn Arg Ile Ser Glu
        115                 120                 125

Gln Thr Asp Phe Asn Gly Val Lys Val Leu Ser Ser Asp Gln Lys Leu
    130                 135                 140

Thr Ile Gln Val Gly Ala Asn Asp Gly Glu Thr Ile Asp Ile Asp Leu
145                 150                 155                 160

Gln Gly Leu Thr Gly Phe Asp Val Thr Glu Asn Gly Thr Lys Ile Gly
                165                 170                 175

Ser Ala Ile Ala Asp Lys Ala Met Val Lys Asp Asp Thr Gly Thr Asp
            180                 185                 190

Val Ala Phe Asp Leu Gly Glu Ser Phe Gln Thr Gly Gly Ala Leu Glu
        195                 200                 205

Lys Ala Thr Leu Val Ser Gly Lys Thr Lys Asp Gly Lys Glu Gly Tyr
    210                 215                 220

Tyr Ile Gln Thr Thr Asp Ala Ala Thr Gly Ala Lys Thr Tyr Ala Thr
225                 230                 235                 240

Ala Lys Ile Asp Asp Lys Gly Val Val Thr Lys Gly Ala Asp Val Thr
                245                 250                 255

Asp Val Lys Asp Pro Leu Ala Thr Leu Asp Lys Ala Leu Ala Gln Val
            260                 265                 270

Asp Gly Leu Arg Ser Ser Leu Gly Ala Val Gln Asn Arg Phe Asp Ser
        275                 280                 285

Val Ile Ser Asn Leu Asn Ser Thr Val Asn Asn Leu Ser Ala Ser Gln
    290                 295                 300

Ser Arg Ile Gln Asp Ala Asp Tyr Ala Thr Glu Val Ser Asn Met Ser
305                 310                 315                 320
```

```
Arg Ala His Ile Leu Gln Gln Ala Gly Thr Ser Val Leu Ala Gln Ala
                325                 330                 335

Asn Gln Ser Thr Gln Asn Val Leu Ser Leu Leu Arg
            340                 345

<210> SEQ ID NO 39
<211> LENGTH: 505
<212> TYPE: PRT
<213> ORGANISM: Salmonella muenchen

<400> SEQUENCE: 39

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Gly Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Glu Ile Ser Ser Lys Thr Leu Gly Leu Asp Lys Leu Asn Val Gln
                165                 170                 175

Asp Ala Tyr Thr Pro Lys Glu Thr Ala Val Thr Val Asp Lys Thr Thr
            180                 185                 190

Tyr Lys Asn Gly Thr Asp Thr Ile Thr Ala Gln Ser Asn Thr Asp Ile
        195                 200                 205

Gln Thr Ala Ile Gly Gly Gly Ala Thr Gly Val Thr Gly Ala Asp Ile
    210                 215                 220

Lys Phe Lys Asp Gly Gln Tyr Tyr Leu Asp Val Lys Gly Gly Ala Ser
225                 230                 235                 240

Ala Gly Val Tyr Lys Ala Thr Tyr Asp Glu Thr Thr Lys Lys Val Asn
                245                 250                 255

Ile Asp Thr Thr Asp Lys Thr Pro Leu Ala Thr Ala Glu Ala Thr Ala
            260                 265                 270

Ile Arg Gly Thr Ala Thr Ile Thr His Asn Gln Ile Ala Glu Val Thr
        275                 280                 285

Lys Glu Gly Val Asp Thr Thr Thr Val Ala Ala Gln Leu Ala Ala Ala
    290                 295                 300

Gly Val Thr Gly Ala Asp Lys Asp Asn Thr Ser Leu Val Lys Leu Ser
305                 310                 315                 320

Phe Glu Asp Lys Asn Gly Lys Val Ile Asp Gly Gly Tyr Ala Val Lys
                325                 330                 335

Met Gly Asp Asp Phe Tyr Ala Ala Thr Tyr Asp Glu Lys Gln Val Gln
            340                 345                 350
```

```
Leu Leu Leu Asn Asn His Tyr Thr Asp Gly Ala Gly Val Leu Gln Thr
        355                 360                 365

Gly Ala Val Lys Phe Gly Gly Ala Asn Gly Lys Ser Glu Val Val Thr
    370                 375                 380

Ala Thr Val Gly Lys Thr Tyr Leu Ala Ser Asp Leu Asp Lys His Asn
385                 390                 395                 400

Phe Arg Thr Gly Gly Glu Leu Lys Glu Val Asn Thr Asp Lys Thr Glu
                405                 410                 415

Asn Pro Leu Gln Lys Ile Asp Ala Ala Leu Ala Gln Val Asp Thr Leu
            420                 425                 430

Arg Ser Asp Leu Gly Ala Val Gln Asn Arg Phe Asn Ser Ala Ile Thr
        435                 440                 445

Asn Leu Gly Asn Thr Val Asn Asn Leu Ser Ser Ala Arg Ser Arg Ile
    450                 455                 460

Glu Asp Ser Asp Tyr Ala Thr Glu Val Ser Asn Met Ser Arg Ala Gln
465                 470                 475                 480

Ile Leu Gln Gln Ala Gly Thr Ser Val Leu Ala Gln Ala Asn Gln Val
                485                 490                 495

Pro Gln Asn Val Leu Ser Leu Leu Arg
            500                 505

<210> SEQ ID NO 40
<211> LENGTH: 490
<212> TYPE: PRT
<213> ORGANISM: Salmonella typhimurium

<400> SEQUENCE: 40

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65              70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Asn Gly
        115                 120                 125

Gln Thr Gln Phe Ser Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Glu Lys Ile Asp Gly Asp Leu Lys Phe Asp
    210                 215                 220
```

-continued

```
Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
            245                 250                 255

Val Thr Leu Ala Ala Val Thr Pro Ala Thr Val Thr Thr Ala Thr Ala
        260                 265                 270

Leu Ser Gly Lys Met Tyr Ser Ala Asn Pro Asp Ser Asp Ile Ala Lys
    275                 280                 285

Ala Ala Leu Thr Ala Ala Gly Val Thr Gly Thr Ala Ser Val Val Lys
290                 295                 300

Met Ser Tyr Thr Asp Asn Asn Gly Lys Thr Ile Asp Gly Gly Leu Ala
305                 310                 315                 320

Val Lys Val Gly Asp Asp Tyr Tyr Ser Ala Thr Gln Asp Lys Asp Gly
            325                 330                 335

Ser Ile Ser Ile Asp Thr Thr Lys Tyr Thr Ala Asp Asn Gly Thr Ser
        340                 345                 350

Lys Thr Ala Leu Asn Lys Leu Gly Gly Ala Asp Gly Lys Thr Glu Val
    355                 360                 365

Val Thr Ile Asp Gly Lys Thr Tyr Asn Ala Ser Lys Ala Ala Gly His
370                 375                 380

Asp Phe Lys Ala Glu Pro Glu Leu Ala Glu Gln Ala Ala Lys Thr Thr
385                 390                 395                 400

Glu Asn Pro Leu Gln Lys Ile Asp Ala Ala Leu Ala Gln Val Asp Thr
            405                 410                 415

Leu Arg Ser Asp Leu Gly Ala Val Gln Asn Arg Phe Asn Ser Ala Ile
        420                 425                 430

Thr Asn Leu Gly Asn Thr Val Asn Asn Leu Ser Ser Ala Arg Ser Arg
    435                 440                 445

Ile Glu Asp Ser Asp Tyr Ala Thr Glu Val Ser Asn Met Ser Arg Ala
450                 455                 460

Gln Ile Leu Gln Gln Ala Gly Thr Ser Val Leu Ala Gln Ala Asn Gln
465                 470                 475                 480

Val Pro Gln Asn Val Leu Ser Leu Leu Arg
            485                 490
```

<210> SEQ ID NO 41
<211> LENGTH: 468
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
aaggaaaaga tcatggcaca agtcattaat acaaacagcc tgtcgctgtt gacccagaat      60
aacctgaaca atcccagtc cgctctgggc accgctatcg agcgtctgtc ttccggtctg     120
cgtatcaaca gcgcgaaaga cgatgcggca ggtcaggcga ttgctaaccg tttcaccgcg     180
aacatcaaag gtctgactca ggcttcccgt aacgctaacg acggtatctc cattgcgcag     240
accactgaag gcgcgctgaa cgaaatcaac aacaacctgc agcgtgtgcg tgaactggcg     300
gttcagtctg ctaacggtac taactcccag tctgaccttg actctatcca ggctgaaatc     360
acccagcgtc tgaacgaaat cgaccgtgta tccggtcaga ctcagttcaa cggcgtgaaa     420
gtcctggcgc aggacaacac cctgaccatc caggttggtg ccaacgac                 468
```

ANTIBODIES AGAINST FLAGELLIN AND USES THEREOF

CROSS-REFERENCE TO RELATED APPLICATION

This application claims priority to U.S. Provisional Patent Application No. 60/967,718, filed Sep. 5, 2007, entitled, "Antibodies Against Flagellin and Uses Thereof," which is hereby incorporated by reference in its entirety.

GOVERNMENT FUNDING

This invention was made with government support under National Institute Health grant #'s R01GM57407, R43AI48249, R29GM54773 and ROGM60699. The United States government has certain rights in the invention.

BACKGROUND OF THE INVENTION

The human intestine is colonized by a large and diverse population of commensal bacteria and, on occasion, is exposed to potentially pathogenic bacteria. One particular subset of intestinal bacteria have flagella, which are whip-like organelles that attach to a rotatory motor embedded in the bacterial cell wall. Flagella provide bacteria with motility and enable these microbes to reach, adhere and eventually invade or colonize a particular niche in their host. An individual flagellum is composed of approximately 20,000 subunits of the monomeric protein flagellin. Due to physical constraints by its function, flagellin has a relatively conserved structure among widely diverse bacterial species (Steiner, T. S. *Infect Immun.* 2007 February; 75(2):545-52).

Flagellin is highly antigenic and is a major immunoglobulin target in a variety of infectious events (Sitaraman et al., *Am J Physiol Gastrointest Liver Physiol.* 2005 February; 288(2): G403-6). As such, it is a potent and direct activator of the innate immune system. From the perspective of the host, flagellin is a microbial-associated molecular pattern (MAMP) i.e., a microbial-associated determinant that can be perceived by the innate immune system, typically by pattern recognition receptors. Flagellin therefore serves as a danger signal across a wide variety of eukaryotes and is a potent inducer of inflammatory effector responses in the mammalian gut (Neish, A. S., *Am J Physiol Gastrointest Liver Physiol.* 2007 February; 292(2):G462-6). Specifically, upon detection of miniscule levels of the monomeric protein flagellin, the mammalian germline encoded cell surface receptor Toll-like receptor 5 (TRL5) can directly promote a mucosal inflammatory response and trigger a massive induction of host gene expression designed to arm and protect the host against the invading microbe. The resulting inflammatory cascade triggered by flagellin can be profound, causing clinical manifestations and tissue damage (Gewirtz, A. T., *Am J Physiol Gastrointest Liver Physiol.* 2007 March; 292(3):G706-10).

Inflammatory bowel disease (IBD) is characterized by inflammation of the bowel, i.e., the large or small intestine, and causes abdominal pain, rectal bleeding and/or diarrhea. The most common types of IBD are Ulcerative Colitis and Crohn's Disease. While the inflammation in Ulcerative Colitis is more superficial and limited to the inner lining of the colon and rectum, the inflammation associate with Crohn's Disease extends from the mucosa through the entire thickness of the bowel wall and can affect any area of the gastrointestinal tract from the mouth to the anus.

IBD, in general, and Crohn's Disease, in particular, is thought to be driven by exaggerated mucosal immune responses to enteric microflora. For example, in a spontaneously colitic mouse model (C3H/HejBir mice), sera screened for differential expression of bacterial protein antigens identified hundreds of antigens, with approximately 25% being bacterial flagellins (Lodes, et al., *J Clin Invest.* 2004 May; 113(9):1296-306). Additionally, it has been demonstrated that flagellin released by commensal *E. coli* isolates activates the expression of chemokines (e.g., IL-8) that ultimately cause recruitment of activated neutrophils. Neutrophils however, are not merely an indicator of active IBD, but instead are thought to cause much of the damage and symptoms associated with active inflammation and to actually drive acute flares of IBD (Gewirtz, A. T., *Am J Physiol Gastrointest Liver Physiol.* 2007 March; 292(3):G706-10).

Further, the identification of a dominant-negative TLR5 polymorphism, which reduces the adaptive immune response to flagellin and negatively associates with Crohn's Disease, suggests that immune responses to flagellin are not merely associated with Crohn's Disease, but instead actually promote the pathogenic response (Gewirtz, et al., *Am J Physiol Gastrointest Liver Physiol.* 2006 June; 290(6):G1157-63). Notwithstanding, the specific organisms that drive the immune response associated with IBD are not well defined and there still remains a question as to whether host responses to flagellin are, in fact, part of the healthy, beneficial immune response or, alternatively, whether they are part of an aberrant immune response that should be therapeutically targeted (Gewirtz, A. T., *Am J Physiol Gastrointest Liver Physiol.* 2007 March; 292(3):G706-10).

Current treatments for IBD typically involve administration of anti-inflammatory drugs, corticosteroids such as prednisone, immune system suppressors, antibiotics, as well as anti-diarrheals, laxatives, pain relievers or other over-the-counter (OTC) drugs, and in some cases surgery. These therapies, however, have clear drawbacks in that they are associated with potentially long-term side effects and are merely palliative in nature. Accordingly, improved treatments for IBD, as well as other flagellated bacterial infections would be beneficial.

SUMMARY OF THE INVENTION

The present invention provides a novel class of high affinity monoclonal antibodies that bind to flagellin and neutralize a broad spectrum of bacteria including, but not limited, to gram-negative bacteria, such as *E. coli, Salmonella, Serratia, Proteus, Enterobacter, Citrobacter, Campylobacter* and *Pseudomonas*. Accordingly, the antibodies of the present invention can be used to treat, prevent and diagnose a variety of bacterial diseases, including both infectious and non-infectious diseases in humans, other animals and birds.

Antibodies of the invention generally are characterized as having one or more of the following properties: (i) neutralization (i.e., inhibition) of bacterial flagellin, (including flagellin bound to bacteria or "free", circulating flagellin in the systemic circulation); (ii) cross-reactivity with flagellin from a broad spectrum of bacteria; (iii) inhibition of bacterial invasion into susceptible epithelial cells; (iv) binding to flagellin with an affinity of at least $10^{10}$ M$^{-1}$; (v) reduction or prevention of flagellin-induced tissue injury; (vi) reduction or prevention of flagellin-stimulated neutrophil infiltration; (vii) reduction or prevention of colonic mucosal congestion, erosion and/or hemorrhagic ulcerations associated with IBD; and (viii) reduction or prevention of cytokine production, including MDA, IL-1β, TNFα, MIP-1, MIP-2, IL-6 and IL-8, and pro-inflammatory free radical synthesizing enzymes, such as the inducible nitric-oxide synthases; (ix) ability to opsonize bacteria; and (x) ability to promote macrophage ingestion of bacteria.

From a structural standpoint, particular representative antibodies of the invention include a heavy chain variable region comprising an amino acid sequence which is at least 80% (e.g., 85%, 90%, 95%, 96%, 97%, 98% or 99%) identical to the heavy chain variable region amino acid sequence set forth in SEQ ID NO: 1 or 2. Other particular antibodies of the present invention include a light chain variable region comprising an amino acid sequence which is at least 80% (e.g., 85%, 90%, 95%, 96%, 97%, 98% or 99%) identical to the light chain variable region amino acid sequence set forth in SEQ ID NO:3 or 4. The antibodies may also include both of the aforementioned heavy chain and light chain variable regions.

The variable heavy and light chain regions of the antibodies typically include one or more complementarity determining regions (CDRs). These include one or more CDR1, CDR2, and CDR3 regions. Accordingly, other particular antibodies of the present invention include one or more CDR sequences selected from a heavy chain variable region CDR1 comprising SEQ ID NO:5 or 6; a heavy chain variable region CDR2 comprising SEQ ID NO:7 or 8; a heavy chain variable region CDR3 comprising SEQ ID NO:9 or 10; a light chain variable region CDR1 comprising SEQ ID NO:11 or 12; a light chain variable region CDR2 comprising SEQ ID NO:13 or 14; a light chain variable region CDR3 comprising SEQ ID NO:15 or 16; and combinations thereof.

The antibodies may also comprise one or more CDRs which are at least 80% (e.g., 85%, 90%, 95%, 96%, 97%, 98% or 99%) identical to any of the aforementioned CDRs, or combinations of CDRs.

Also provided by the present invention are antibodies that bind to the same or overlapping epitopes bound by any of the aforementioned antibodies. In a particular embodiment, these antibodies cross-react with a variety of gram-negative bacteria, including *Proteus Vulgaris*, non-pathogenic *E. Coli*, *Citrobacter freundii*, *Serratia marcenscens*, *Enterobacter cloacae*, *Campylobacter jejuni*, *Helicobacter pylori*, *Pseudomonas aeruginosa*, *Salmonella typhimurium*, *Salmonella muenchen*, *Proteus mirabilis* and Enteropathogenic *E. Coli*. In another particular embodiment, the antibodies bind to an epitope on flagellin of *Salmonella muenchen* located between amino acids 37-43, part of another highly conserved RINSA region (amino acids 31-52) within a conserved N-terminal region.

In another aspect, the invention pertains to antibodies that cross compete for binding to flagellin with the anti-flagellin antibodies described herein. For example, the present invention provides for an antibody that cross competes for binding to flagellin with an antibody comprising heavy and light chain variable regions comprising the amino acid sequences set forth in SEQ ID NOs: 2 and 4 or SEQ ID NOs: 1 and 3, respectively. The invention also pertains to antibodies that bind to an epitope on flagellin recognized by an antibody described herein. For example, the present invention provides for an antibody that binds to an epitope on flagellin recognized by an antibody comprising heavy and light chain variable regions comprising the amino acid sequences set forth in SEQ ID NOs: 2 and 4 or SEQ ID NOs: 1 and 3, respectively.

Antibodies of the present invention include all known immunoglobulin forms and other protein scaffolds with antibody-like properties. For example, the antibody can be a murine antibody, a human antibody, a humanized antibody, a chimeric antibody or a protein scaffold with antibody-like properties, such as fibronectin or Ankyrin repeats. The antibody also can have any of the following isotypes: IgG1, IgG2, IgG3, IgG4, IgM, IgA1, IgA2, IgAsec, IgD and IgE. Antibodies of the invention also include antibody fragments, such as an Fab, Fab'2, ScFv, SMIP, affibody, avimer, nanobody or a domain antibody.

In one embodiment, the invention provides fully human antibodies (i.e., which contain human CDR and framework sequences) that bind to and neutralize flagellin. Particular human antibodies of the invention comprise a heavy chain variable region from a human VH 1-24 or VH 3-23 germline gene, and/or a light chain variable region from human VK A26 or VK V2-17 germline gene. The sequences of these and other human germline genes are publicly available and can be found, for example, in the "VBase" human germline sequence database (available on the Internet at mrc-cpe.cam.ac.uk/vbase) and the "IMGT" database (available on the Internet at imgt.cines.fr/), and are hereby incorporated by reference.

Antibodies of the invention can be administered alone or in combination with other therapeutic agents. For example, the antibodies can be administered in combination with (i.e., together with or linked to) cytotoxins, antibacterial agents, including antibiotics and/or other therapeutic antibodies. In one embodiment, the antibody is linked to a second antibody (i.e., thereby forming a bispecific antibody) or other binding agent that binds to a different target (e.g., an Fc receptor on an immune cell) or a different epitope on flagellin.

In yet another aspect, the present invention provides isolated nucleic acids encoding the aforementioned antibodies of the invention. In particular embodiments, the nucleic acid encodes a heavy chain variable region comprising a nucleotide sequence which is at least 80% (e.g., 85%, 90%, 95%, 96%, 97%, 98% or 99%) identical to, or which hybridizes under high stringency conditions to, SEQ ID NO$_{19}$ or 20; or a light chain variable region comprising a nucleotide sequence which is at least 80% (e.g., 85%, 90%, 95%, 96%, 97%, 98% or 99%) identical to, or which hybridizes under high stringency conditions to, SEQ ID NO:21 or 22; or combinations of such heavy and light variable regions.

The present invention also provides hybridomas that express and/or produce the aforementioned antibodies.

Further provided by the invention are kits comprising one or more of the aforementioned antibodies, optionally, with instructions for use in treating or diagnosing bacterial diseases associated with flagellin in humans, other animals and birds.

As noted above, antibodies of the present invention can be used in a broad variety of diagnostic and therapeutic applications, or used in the manufacture of one or more medicaments for diagnostic or therapeutic applications. These applications include treatment and prevention of both infectious and non-infectious bacterial diseases. Particular non-infectious diseases include, but are not limited to, inflammatory bowel diseases (IBDs), such as Crohn's Disease and colitis. Other particular diseases include gram negative bacterial infections (e.g., enterobacterial infections) sepsis and septic shock, in particular. Still other particular diseases include Anthrax, Bacterial Meningitis, Botulism, Brucellosis, Cat Scratch Disease, Cholera, Diphtheria, Epidemic Typhus, Impetigo, Legionellosis, Leprosy, Leptospirosis, Listeriosis, Lyme Disease, Melioidosis, MRSA infection, Nocardiosis, Pertussis, Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Urinary Tract Infections and Necrotizing enterocolitis.

Other features and advantages of the invention will be apparent from the following detailed description, and from the claims.

BRIEF DESCRIPTION OF THE DRAWINGS

FIG. 1 shows the nucleotide sequence (SEQ ID NO:19) and primary amino acid sequence (SEQ ID NO:1) of the heavy chain variable region of murine mAb 741. The CDR1 (SEQ ID NOs: 23 and 5), CDR2 (SEQ ID NOs: 25 and 7) and CDR3 (SEQ ID NOs:27 and 9) nucleotide and amino acid sequences regions, respectively, are delineated.

FIG. 2 shows the nucleotide sequence (SEQ ID NO:21) and primary amino acid sequence (SEQ ID NO:3) of the light chain variable region of murine mAb 741. The CDR1 (SEQ ID NOs:29 and 1), CDR2 (SEQ ID NOs:31 and 13) and CDR3 (SEQ ID NOs:33 and 15) regions are delineated.

FIG. 3 shows the nucleotide sequence (SEQ ID NO:20) and primary amino acid sequence (SEQ ID NO:2) of the heavy chain variable region of human mAb 763. The CDR1 (SEQ ID NOs:24 and 6), CDR2 (SEQ ID NOs:26 and 8) and CDR3 (SEQ ID NOs:28 and 10) regions are delineated.

FIG. 4 shows the nucleotide sequence (SEQ ID NO:22) and primary amino acid sequence (SEQ ID NO:4) of the light chain variable region of human mAb 763. The CDR1 (SEQ ID NOs:30 and 12), CDR2 (SEQ ID NOs:32 and 14) and CDR3 (SEQ ID NOs:34 and 16) regions are delineated.

FIG. 19 is a chart depicting the effects of mAb 763, a positive control mAb (Infliximab) and CBH2, a non-relevant human mAb control, on DNBS-induced mediator (i.e., MDA, IL-1β, TNFα, MIP-1, MIP-2 and IL-8) production from colon extracts.

DETAILED DESCRIPTION OF THE INVENTION

Figure 5:
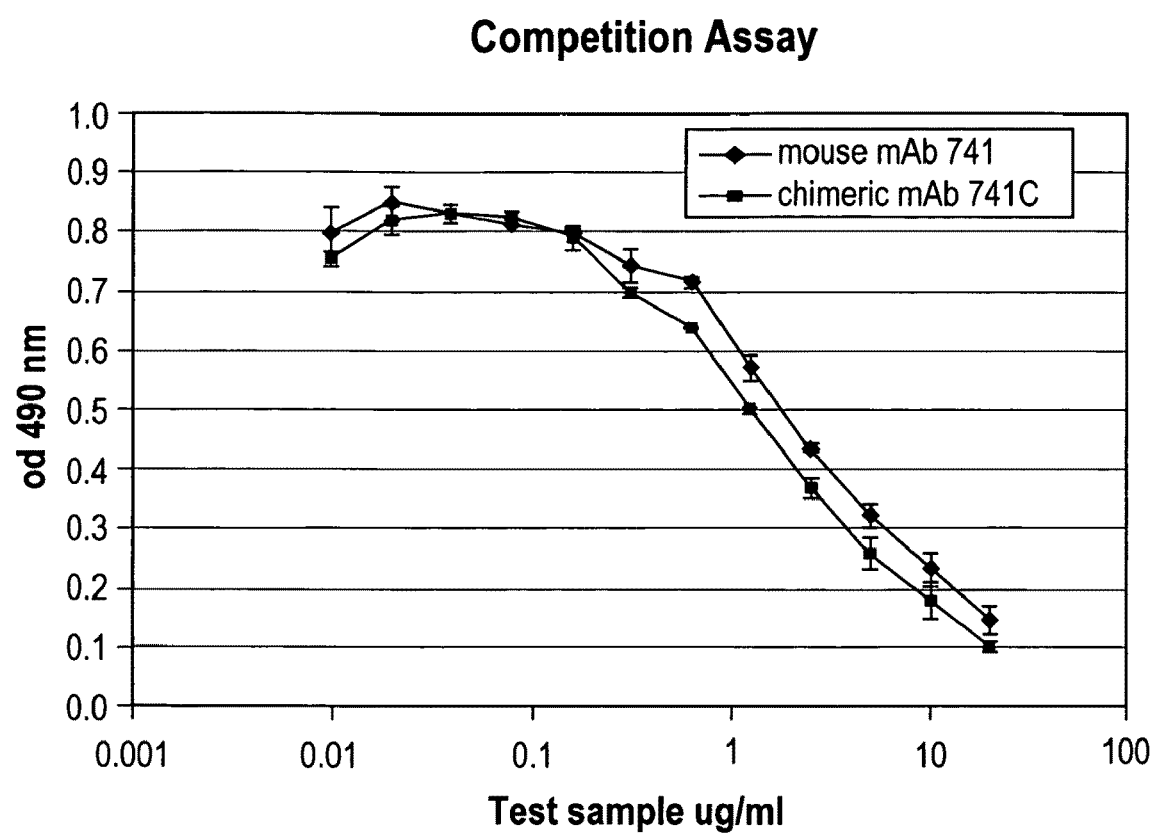
FIG. 5 shows the binding affinities of chimeric mAb 741C and murine mAb 741, as assessed by competition ELISA.

In order that the present invention may be more readily understood, certain terms are first defined. Additional definitions are set forth throughout the detailed description.

I. Definitions

As used herein, the term "flagellin" carries its art recognized meaning as referring to a monomeric subunit of bacterial flagellum. The term "flagellin" includes the monomeric protein flagellin bound to bacteria, free circulating flagellin, and flagellin subunits of an individual flagellum or flagella. The amino acid sequences of flagellins from different bacterial strains are known in the art and are widely conserved, as discussed by Steiner, T. S. (*Infect Immun.* 2007 February; 75(2):545-52), the teachings of which are incorporated by reference herein. Preferred antibodies of the invention cross react with flagellins of multiple bacterial species, including, but not limited to, *Proteus Vulgaris*, non-pathogenic *E. Coli*, *Citrobacter freundii*, *Serratia marcescens*, *Pseudomonas aeruginosa*, *Salmonella typhimurium*, *Proteus mirabilis*, and Enteropathogenic *E. Coli*. Representative flagellin sequences, include, but are not limited to, the sequences set forth below.

*Proteus mirabilis* (GI:1169696)

(SEQ ID NO:35)
MAQVINTNYLSLVTQNNLNKSQGTLGSAIERLSSGLRINSAKDDAAGQAI
ANRFTSNVNGLTQASRNANDGISIAQTTEGALNEINNNLQRIRELTVQAK
NGTNSNSDITSIQNEVKNVLDEINRISEQTQFNGVKVLSGEKSEMVIQVG
TNDNETIKFNLDKVDNDTLGVASDKLFDTKTEKKGVTAAGAGVTDAKKIN
AAATLDMMVSLVKEFNLDGKPVTDKFIVTKGGKDYVATKSDFELDATGTK
LGLKASATTEFKVDAGKDVKTLNVKDDALATLDKAINTIDESRSKLGAIQ
NRFESTINNLNNTVNNLSASRSRILDADYATEVSNMSRGQILQQAGTSVL
AQANQVPQTVLSLLR
(Belas, et al. (1994). Gene 148, 33-41.)

*Pseudomonas aeruginosa* (GI:3386643)

(SEQ ID NO:36)
MALTVNTNIASLNTQRNLNNSSASLNTSLQRLSTGSRINSAKDDAAGLQI
ANRLTSQVNGLNVATKNANDGISLAQTAEGALQQSTNILQRMRDLSLQSA
NGSNSDSERTALNGEVKQLQKELDRISNTTTFGGRKLLDGSFGVASFQVG
SAANEIISVGIDEMSAESLNGTYFKADGGGAVTAATASGTVDIAIGITGG
SAVNVKVDMKGNETAEQAAAKIAAAVNDANVGIGAFTDGAQISYVSKASA
DGTTSAVSGVAITDTGSTGAGTAAGTTTFTEANDTVAKIDISTAKGAQSA
VLVIDEAIKQIDAQRADLGAVQNRFDNTINNLKNIGENVSAARGRIEDTD
FAAETANLTKNQVLQQAGTAILAQANQLPQSVLSLLR
(Spangenberg, C. et al., (1996). FEBS Lett. 396, 213-217)

*Escherichia coli* (GI:1655807)

(SEQ ID NO:37)
MAQVINTNSLSLITQNNLNKNQSALSSSIERLSSGLRINSAKDDAAGQAI
ANRFTSNIKGLTQAARNANDGISVAQTTEGALSEINNNLQRIRELTVQAT
TGTNSDSDLDSIQDEIKSRLDEIDRVSGQTQFNGVNVLAKDGSMKIQVG
ANDGETITIDLKKIDSDTLGLNGFNVNGKGTITNKAATVSDLTSAGAKLN
TTTGLYDLKTENTLLTTDAAFDKLGNGDKVTVGGVDYTYNAKSGDFTTTK
STAGTGVDAAAQAADSASKRDALAATLHADVGKSVNGSYTTKDGTVSFET
DSAGNITIGGSQAYVDDAGNLTTNNAGSAAKADMKALLKAASEGSDGASL
TFNGTEYTIAKATPATTTPVAPLIPGGITYQATVSKDVVLSETKAAAATS
SITFNSGVLSKTIGFTAGESSDAAKSYVDDKGGITNVADYTVSYSVNKDN
GSVTVAGYASATDTNKDYAPAIGTAVNVNSAGKITTETTSAGSATTNPLA
ALDDAISSIDKFRSSLGAIQNRLDSAVTNLNNTTTNLSEAQSRIQDADYA
TEVSNMSKAQIIQQAGNSVLAKANQVPQQVLSLLQG

*Serratia marcescens* (GI:514988)

(SEQ ID NO:38)
MAQVINTNSLSLMAQNNLNKSQSSLGTAIERLSSGLRINSAKDDAAGQAI
SDRFTANIKGLTQASRNANDGISLAQTTEGALNEVNDNLQNIRRLTVQAQ
NGSNSTSDLKSIQDEITQRMSEINRISEQTDFNGVKVLSSDQKLTIQVG
ANDGETIDIDLQGLTGFDVTENGTKIGSAIADKAMVKDDTGTDVAFDLGE
SFQTGGALEKATLVSGKTKDGKEGYYIQTTDAATGAKTYATAKIDDKGVV
TKGADVTDVKDPLATLDKALAQVDGLRSSLGAVQNRFDSVISNLNSTVNN
LSASQSRIQDADYATEVSNMSRAHILQQAGTSVLAQANQSTQNVLSLLR
(Akatsuka, H. etal., (1995). Gene 163, 157-158)

*Salmonella muenchen* (GI:1333832)

(SEQ ID NO:39)
MAQVINTNSLSLLTQNNLNKSQSALGTAIERLSSGLRINSAKDDAAGQAI
ANRFTANIKGLTQASRNANDGISIAQTTEGALNEINNNLQRVRELAVQSA
NGTNSQSDLDSIQAEITQRLNEIDRVSGQTQFNGVKVLAQDNTLTIQVGA
NDGETIDIDLKEISSKTLGLDKLNVQDAYTPKETAVTVDKTTYKNGTDTI
TAQSNTDIQTAIGGGATGVTGADIKFKDGQYYLDVKGGASAGVYKATYDE
TTKKVNIDTTDKTPLATAEATAIRGTATITHNQIAEVTKEGVDTTTVAAQ
LAAAGVTGADKDNTSLVKLSFEDKNGKVIDGGYAVKMGDDFYAATYDEK
QVQLLLNNHYTDGAGVLQTGAVKFGGANGKSEVVTATVGKTYLASDLDKH
NFRTGGELKEVNTDKTENPLQKIDAALAQVDTLRSDLGAVQNRFNSAITN
LGNTVNNLSSARSRIEDSDYATEVSNMSRAQILQQAGTSVLAQANQVPQN
VLSLLR
(Wei, L. N. et al., (1985). J. Mol. Biol. 186, 791-803)

*Salmonella typhimurium* (GI:153979)

(SEQ ID NO:40)
MAVINTNSLSLLTQNNLNKSQSALGTAIERLSSGLRINSAKDDAAGQAIA
NRFTANIKGLTQASRNANDGISIAQTTEGALNEINNNLQRVRELAVQSAN
STNSQSDLDSIQAEITQRLNEIEDRVNGQTQFSGVKVLAQDNTLTIQVGA
NDGETIDIDLKQINSQTLGLDTLNVQQKYKVSDTAATVTGYADTTIALDN
STFKASATGLGGTDEKIDGDLKFDDTTGKYYAKVTVTGGTGKDGYYEVSV
DKTNGEVTLAAVTPATVTTATALSGKMYSANPDSDIAKAALTAAGVTGTA
SVVKMSYTDNNGKTIDGGLAVKVGDDYYSATQDKDGSISIDTTKYTADNG
TSKTALNKLGGADGKTEVVTIDGKTYNASKAAGHDFKAEPELAEQAAKTT
ENPLQKIDAALAQVDTLRSDLGAVQNRFNSAITNLGNTVNNLSSARSRIE
DSDYATEVSNMSRAQILQQAGTSVLAQANQVPQNVLSLLR
(Joys, T. M. (1985). J. Biol. Chem. 260, 15758-15761.)

As used herein, the term "bacteria" or "bacterium" refers to unicellular prokaryotic microorganisms, i.e., organisms without a cell nucleus or any other membrane-bound organelles. Bacteria are typically a few micrometres in length and individual bacteria have a wide-range of shapes, ranging from spheres to rods to spirals. Although the vast majority of bacteria are rendered harmless or beneficial by the protective effects of the immune system, a few pathogenic bacteria cause infectious diseases.

As used herein, "gram-negative bacteria" or "gram-negative bacterium" refer to bacteria having characteristic staining properties under the microscope, where they either do not stain or are decolorized by alcohol during Gram's method of staining.

Gram-negative bacteria generally have the following characteristics: (1) their cell wall only contains a few layers of peptidoglycan (which is present in much higher levels in Gram-positive bacteria); (2) the cells are surrounded by an outer membrane containing lipopolysaccharide (which consists of Lipid A, core polysaccharide, and O-polysaccharide) outside the peptidoglycan layer; (3) porins exist in the outer membrane, which act like pores for particular molecules; (4) there is a space between the layers of peptidoglycan and the secondary cell membrane called the periplasmic space; (5) the S-layer is directly attached to the outer membrane, rather than the peptidoglycan; (6) if present, flagella have four supporting rings instead of two; (7) no teichoic acids or lipoteichoic acids are present; (8) lipoproteins are attached to the polysaccharide backbone, whereas in Gram-positive bacteria no lipoproteins are present; and (9) most do not sporulate.

Examples of gram-negative bacteria include, but are not limited to, *Escherichia coli*, Enterobacteriaceae, *Moraxella, Helicobacter, Burkholderia cepacia, Stenotrophomonas, Bdellovibrio*, acetic acid bacteria, cyanobacteria, spirochaetes, green sulfur and green non-sulfur bacteria, *Neisseria gonorrhoeae, Neisseria meningitides, Moraxella catarrhalis, Hemophilus influenzae, Klebsiella pneumoniae, Legionella pneumophila, Pseudomonas aeruginosa, Proteus mirabilis, Enterobacter cloacae, Serratia marcescens, Helicobacter pylori, Salmonella enteritidis*, and *Salmonella typhi*.

As used herein, "a bacterial infectious disease" is a disease or infection caused by bacteria.

As used herein, "a gram negative bacterial infection" is a disease or infection caused by gram negative bacteria.

As used herein, "an enterobacterial infection" is an infection caused by Enterobacteriaceae.

As used herein, "Enterobacteriaceae" and "enterobacteria" refer to a large family of bacteria, including many of the more familiar pathogens, such as *Salmonella* and *Escherichia coli*. Genetic studies place them among the Proteobacteria, and they are given their own order (Enterobacteriales). Members of the Enterobacteriaceae are rod-shaped, and are typically 1-5 µm in length. Like other Proteobacteria, they have Gram-negative stains, and they are facultative anaerobes, fermenting sugars to produce lactic acid and various other end products. They also reduce nitrate to nitrite. Unlike most similar bacteria, enterobacteria generally lack cytochrome C oxidase, although there are exceptions (e.g., *Plesiomonas*). Most have many flagella used to move about, but a few genera are non-motile. They are non-spore forming, and except for *Shigella dysenteriae* strains they are catalase-positive. Many members of this family are a normal part of the gut flora found in the intestines of humans and other animals, while others are found in water or soil, or are parasites on a variety of different animals and plants.

Examples of Enterobacteriaceae include, but are not limited to, *Alishewanella, Alterococcus, Aquamonas, Aranicola, Arsenophonus, Azotivirga, Blochmannia, Brenneria, Buchnera, Budvicia, Buttiauxella, Cedecea, Citrobacter, Dickeya, Edwardsiella, Enterobacter, Erwinia* (e.g. *Erwinia amylovora*), *Escherichia* (e.g. *Escherichia coli*), *Ewingella, Grimontella, Hafnia, Klebsiella* (e.g. *Klebsiella pneumoniae*), *Kluyvera, Leclercia, Leminorella, Moellerella, Morganella, Obesumbacterium, Pantoea, Pectobacterium, Candidatus Phlomobacter, Photorhabdus* (e.g. *Photorhabdus luminescens*), *Plesiomonas* (e.g. *Plesiomonas shigelloides*), *Pragia Proteus* (e.g. *Proteus vulgaris*), *Providencia, Rahnella, Raoultella, Salmonella, Samsonia, Serratia* (e.g. *Serratia marcescens*), *Shigella, Sodalis, Tatumella, Trabulsiella, Wigglesworthia, Xenorhabdus, Yersinia* (e.g. *Yersinia pestis*), and *Yokenella*.

Examples of enterobacterial infections include, but are not limited to, Anthrax (by the bacterium *Bacillus anthracis*), Bacterial Meningitis (caused by a variety of bacteria, including, but not limited to, *Neisseria meningitides, Streptococcus pneumoniae, Listeria monocytogenes, Pseudomonas aeruginosa, Staphylococcus aureus, Streptococcus agalactiae* and *Haemophilus influenzae*), Botulism (caused by bacterium *Clostridium botulinum*), Brucellosis (caused by bacteria of the genus *Brucella*), Campylobacteriosis (caused by bacteria of the genus *Campylobacter*), Cat Scratch Disease (caused by *Bartonella henselae* and *Bartonella clarridgeiae*), Cholera (caused by the bacterium *Vibrio cholerae*), Diphtheria (caused by *Corynebacterium diphtheriae*), Epidemic Typhus (causative organism is *Rickettsia prowazekii*), Impetigo (caused by several bacteria, including, *Staphylococcus aureus* and *Streptococcus pyogenes*), Legionellosis (caused by bacteria belonging to the genus *Legionella*), Leprosy (Hansen's Disease) (caused by the bacterium *Mycobacterium leprae*), Leptospirosis (caused by spirochaetes of the genus *Leptospira*), Listeriosis (caused by the bacterium *Listeria monocytogenes*), Lyme Disease (caused by spirochete bacteria from the genus *Borrelia*), Melioidosis (caused by the bacterium *Burkholderia pseudomallei*), MRSA infection (caused by *Staphylococcus aureus*), Nocardiosis (bacterium of the genus *Nocardia*, most commonly *Nocardia asteroides* or *Nocardia brasiliensis*), Pertussis (Whooping Cough) (caused by the bacterium *Bordetella pertussis*), Plague (caused by the enterobacteria *Yersinia pestis*), Pneumococcal pneumonia (caused by a variety of bacteria, including, but not limited to, *Streptococcus pneumoniae, Staphylococcus aureus, Haemophilus influenzae, Klebsiella pneumoniae, Escherichia coli, Pseudomonas aeruginosa, Moraxella catarrhalis, Chlamydophila pneumoniae, Mycoplasma pneumoniae*, and *Legionella pneumophila*), Psittacosis (caused by a bacterium called *Chlamydophila psittaci*), Q fever (caused by infection with *Coxiella burnetii*), Rocky Mountain Spotted Fever (RMSF) (by *Rickettsia rickettsii*), Salmonellosis (caused by bacteria of the genus *Salmonella*), Scarlet Fever, Shigellosis (caused by bacteria of the genus *Shigella*), Syphilis (caused by *Treponema pallidum*), Tetanus (*Clostridium tetani*), Trachoma, Tuberculosis (caused by mycobacteria, mainly *Mycobacterium tuberculosis*), Tularemia (by the bacterium *Francisella tularensis*), Typhoid Fever (caused by the bacterium *Salmonella typhi*), and Urinary Tract Infections (caused by bacteria such as *Escherichia coli, Staphylococcus saprophyticus, Proteus mirabilis, Klebsiella pneumoniae, Enterobacter* spp., *Pseudomonas* and *Enterococcus*).

As used herein, "gram-positive bacteria" or "gram-positive bacterium" refer to bacteria that retain the stain or that are resistant to decolourisation by alcohol during Gram's method of staining. Gram-positive bacteria generally have the following characteristics: (1) a very thick cell wall (peptidoglycan); (2) if a flagellum is present, it contains two rings for support as opposed to four in Gram-negative bacteria because Gram-positive bacteria have only one membrane layer; and (3) teichoic acids and lipoteichoic acids are present, which serve to act as chelating agents, and also for certain types of adherence. Examples of gram-positive bacteria genera include, but are not limited to, *Bacillus, Listeria, Staphylococcus, Streptococcus, Enterococcus*, and *Clostridium*.

As used herein, "Inflammatory Bowel Disease (IBD)" refers to a group of chronic intestinal diseases characterized by inflammation of the bowel, i.e., the large or small intestine. The most common types of IBD are Ulcerative Colitis and Crohn's Disease. The symptoms of IBD include abdominal pain, diarrhea, bloody diarrhea, severe urgency to have a bowel movement, fever, loss of appetite, weight loss, anemia. IBD can also cause intestinal complications including profuse bleeding from the ulcers, perforation of the bowel, strictures and obstructions, fistulae, perianal disease, toxic megacolon and cancer. The disease can be limited to the intestine or affect the skin, joints, spine, liver, eyes, and other organs.

As used herein, "Crohn's Disease" is a form of IBD that causes severe irritation in the gastrointestinal tract. It usually affects the lower small intestine (i.e., the ileum) or the colon, but can affect other parts of the digestive system including the small intestine, mouth, esophagus, and stomach. The inflammation in Crohn's Disease involves the entire thickness of the bowel wall. There are five different types of Crohn's disease: (1) Ileocolitis (the most common form, which affects the ileum and the colon); (2) Ileitis (which affects the ileum); (3) Gastroduodenal Crohn's Disease (which causes inflammation in the stomach and the duodenum); (4) Jejunoileitis (which causes spotty patches of inflammation in the top half of the small intestine (i.e., the jejunum); and (5) Crohn's (Granulomatous) Colitis (which affects only affects the large intestine).

As used herein, "Ulcerative Colitis" is a form of IBD that affects the colon (the large intestine) alone and inflammation is confined to the mucosa (the inner lining) of the intestine. It can be difficult to diagnose because its symptoms are similar to other intestinal disorders and Crohn's Disease.

The term "Toll-like receptor (TLR)" as used herein, refers to an important family of innate immune receptors that recognize pathogen-associated molecular patterns, i.e., evolutionarily conserved structures that are required for microbial fitness and are not present in the host.

The term "Toll-like receptor 5 (TLR5)" as used herein, refers to the Toll-like receptor which recognizes and binds bacterial flagellin from both gram-positive and gram-negative and activates host inflammatory responses. TLR5 is specifically expressed in monocytes, immature dendritic cells and epithelial cells.

The term "neutralizes" and "inhibits" are used interchangeably herein, and refer to any statistically significant decrease in the biological activity (e.g., motility) of flagellin, including full blocking of the activity. For example, "neutralizes" or "inhibits" can refer to a decrease of about 10%, 20%, 30%, 40%, 50%, 60%, 70%, 80%, 90%, or 100% in flagellin activity.

In particular embodiments of the invention, neutralization or inhibition of flagellin activity results in one or more of the following effects: it prevents bacterial invasion into susceptible epithelial cells, reduces the symptoms of an enterobacterial infection or IBD in a subject, reduces the extent and severity of flagellin-induced tissue injury, reduces flagellin-stimulated neutrophil infiltration, decreases colonic mucosal congestion, erosion and hemorrhagic ulcerations associated with IBD, inhibits or decrease the production of mediators (e.g., MDA, IL-1β, TNFα, MIP-1, MIP-2 and IL-8); and/or counteracts a reduction in body weight associated with IBD.

The term "antibody" or "immunoglobulin," as used interchangeably herein, includes whole antibodies and any antigen binding fragment (i.e., "antigen-binding portion") or single chains thereof. An "antibody" comprises at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. Exemplary antibodies of the invention include mAbs 741 and 763, and antigen-binding portions thereof.

The term "antigen-binding portion" of an antibody (or simply "antibody portion"), as used herein, refers to one or more fragments of an antibody that retain the ability to specifically bind to an antigen (e.g., flagellin). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including $V_H$ and $V_L$ domains; (vi) a dAb fragment (Ward et al. (1989) Nature 341, 544-546), which consists of a $V_H$ domain; (vii) a dAb which consists of a $V_H$ or a $V_L$ domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242, 423-426; and Huston et al. (1988) *Proc. Natl. Acad. Sci. USA* 85, 5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies can be prepared using any art recognized technique and those described herein such as, for example, a hybridoma method, as described by Kohler et al. (1975) *Nature*, 256:495, a transgenic animal, as described by, for example, (see e.g., Lonberg, et al. (1994) *Nature* 368(6474): 856-859), recombinant DNA methods (see, e.g., U.S. Pat. No. 4,816,567), or using phage antibody libraries using the techniques described in, for example, Clackson et al., *Nature*, 352:624-628 (1991) and Marks et al., *J. Mol. Biol.*, 222:581-597 (1991). Monoclonal antibodies include chimeric antibodies, human antibodies and humanized antibodies and may occur naturally or be recombinantly produced.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody," as used herein, is intended to include antibodies having variable regions in which both the framework and CDR regions are derived from human germline immunoglobulin sequences as described, for example, by Kabat et al. (See Kabat, et al. (1991) *Sequences of proteins of Immunological Interest*, Fifth Edition, U.S. Department of Health and Human Services, NIH Publication No. 91-3242). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue which is not encoded by the human germline immunoglobulin sequence. Typically, the human antibody can have up to twenty positions replaced with amino acid residues which are not part of the human germline immunoglobulin sequence. In a particular embodiment, these replacements are within the CDR regions as described in detail below.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) *Clin. Exp. Immunol.* 79, 315-321; Kostelny et al. (1992) *J. Immunol.* 148, 1547-1553.

As used herein, a "heterologous antibody" is defined in relation to the transgenic non-human organism or plant producing such an antibody.

An "isolated antibody," as used herein, is intended to refer to an antibody which is substantially free of other antibodies having different antigenic specificities (e.g., an isolated antibody that specifically binds to flagellin is substantially free of antibodies that specifically bind antigens other than flagellin). In addition, an isolated antibody is typically substantially free of other cellular material and/or chemicals. In one embodiment of the invention, a combination of "isolated" monoclonal antibodies having different flagellin binding specificities are combined in a well defined composition.

As used herein, "isotype" refers to the antibody class (e.g., IgM or IgG1) that is encoded by heavy chain constant region genes. In one embodiment, an antibody or antigen binding portion thereof is of an isotype selected from an IgG1, an IgG2, an IgG3, an IgG4, an IgM, an IgA1, an IgA2, an IgAsec, an IgD, or an IgE antibody isotype. In some embodiments, a monoclonal antibody of the invention is of the IgG1 isotype. In other embodiments, a monoclonal antibody of the invention is of the IgG2 isotype.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence regions in a gene encoding an antibody. Non-classical isotype switching may occur by, for example, homologous recombination between human $\sigma_\mu$ and human $\Sigma_\mu$ ($\delta$-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a $\mu$ switch region, will be 5' (i.e., upstream) of the construct region to be deleted during the switch recombination. The "switch acceptor" region will be between the construct region to be deleted and the replacement constant region (e.g., $\gamma$, $\epsilon$, etc.). As there is no specific site where recombination always occurs, the final gene sequence will typically not be predictable from the construct.

An "antigen" is an entity (e.g., a proteinaceous entity or peptide) to which an antibody or antigen-binding portion thereof binds. In various embodiments of the present invention, an antigen is flagellin.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance. See, e.g., *Epitope Mapping Protocols in Methods in Molecular Biology*, Vol. 66, G. E. Morris, Ed. (1996).

Also encompassed by the present invention are antibodies that bind the same or an overlapping epitope as the particular antibodies described herein, i.e., antibodies that compete for binding to flagellin, or bind to an epitope on flagellin recognized by the particular antibodies described herein. For example, the antibodies of the present invention may specifically bind to an epitope located between amino acids 1-55 of flagellin from *Salmonella* (Genbank Accession No. GI: 1333832) (SEQ ID NO:39) or *Pseudomonas* (Genbank Accession No. GI:3386643) (SEQ ID NO:36). In one embodiment, the antibodies of the present invention may specifically bind to an epitope located between amino acids 1-40 or 30-50 or 30-40 or 37-43 or 31-47 or 41-52 of flagellin from *Salmonella* (Genbank Accession No. GI: 1333832) (SEQ ID NO:39) or *Pseudomonas* (Genbank Accession No. GI:3386643) (SEQ ID NO:36).

Antibodies that recognize the same or an overlapping epitope can be identified using routine techniques such as an immunoassay, for example, by showing the ability of one antibody to block the binding of another antibody to a target antigen, i.e., a competitive binding assay. Competitive binding is determined in an assay in which the immunoglobulin under test inhibits specific binding of a reference antibody to an antigen, such as flagellin. Numerous types of competitive binding assays are known, for example: solid phase direct or indirect radioimmunoassay (RIA), solid phase direct or indirect enzyme immunoassay (EIA), sandwich competition assay (see Stahli et al., (1983) *Methods in Enzymology* 9:242); solid phase direct biotin-avidin EIA (see Kirkland et al., (1986) *J. Immunol.* 137:3614); solid phase direct labeled assay, solid phase direct labeled sandwich assay (see Harlow and Lane, (1988) *Antibodies: A Laboratory Manual*, Cold Spring Harbor Press); solid phase direct label RIA using I-125 label (see Morel et al., (1988) *Mol. Immunol.* 25(1):7); solid phase direct biotin-avidin EIA (Cheung et al., (1990) *Virology* 176:546); and direct labeled RIA. (Moldenhauer et al., (1990) *Scand. J. Immunol.* 32:77). Typically, such an assay involves the use of purified antigen (e.g., flagellin) bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

As used herein, the terms "specific binding," "specifically binds," "selective binding," and "selectively binds," mean that an antibody or antigen-binding portion thereof, exhibits appreciable affinity for a particular antigen or epitope and, generally, does not exhibit significant cross-reactivity with other antigens and epitopes. "Appreciable" or preferred binding includes binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^{-1}$. An antibody that "does not exhibit significant cross-reactivity" is one that will not appreciably bind to an undesirable entity (e.g., an undesirable proteinaceous entity). Specific or selective binding can be determined according to any art-recognized means for determining such binding, including, for example, according to Scatchard analysis and/or competitive binding assays.

The term "$K_D$," as used herein, is intended to refer to the dissociation equilibrium constant of a particular antibody-antigen interaction or the affinity of an antibody for an antigen. In one embodiment, the antibody or antigen binding portion thereof according to the present invention binds an antigen (e.g., flagellin) with an affinity ($K_D$) of 50 nM or better (i.e., or less) (e.g., 40 nM or 30 nM or 20 nM or 10 nM or less), as measured using a surface plasmon resonance assay or a cell binding assay. In a particular embodiment, an antibody or antigen binding portion thereof according to the present invention binds flagellin with an affinity ($K_D$) of 8 nM or better (e.g., 7 nM, 6 nM, 5 nM, 4 nM, 2 nM, 1.5 nM, 1.4 nM, 1.3 nM, 1 nM or less), as measured by a surface plasmon resonance assay or a cell binding assay. In other embodiments, an antibody or antigen binding portion thereof binds an antigen (e.g., flagellin) with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument using recombinant flagellin as the analyte and the antibody as the ligand, and binds to the predetermined antigen with an affinity that is at least two-fold greater than its affinity for binding to a non-specific antigen (e.g., BSA, casein) other than the predetermined antigen or a closely-related antigen.

The term "$K_{off}$," as used herein, is intended to refer to the off rate constant for the dissociation of an antibody from the antibody/antigen complex.

The term "EC50," as used herein, refers to the concentration of an antibody or an antigen-binding portion thereof, which induces a response, either in an in vitro or an in vivo assay, which is 50% of the maximal response, i.e., halfway between the maximal response and the baseline.

As used herein, "glycosylation pattern" is defined as the pattern of carbohydrate units that are covalently attached to a protein, more specifically to an immunoglobulin protein.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies (e.g., $V_H$, $V_L$, CDR3) that bind to flagellin, is intended to refer to a nucleic acid molecule in which the nucleotide sequences encoding the antibody are free of other nucleotide sequences encoding antibodies that bind antigens other than flagellin, which other sequences may naturally flank the nucleic acid in human genomic DNA.

Alternatively, antibodies can comprise an amino acid sequence which is encoded by a nucleotide sequence which hybridizes, e.g., hybridizes under stringent conditions to a nucleotide sequence disclosed herein. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those of ordinary skill in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

The term "modifying," or "modification," as used herein, is intended to refer to changing one or more amino acids in the antibodies. The change can be produced by adding, substituting or deleting an amino acid at one or more positions. The change can be produced using known techniques, such as PCR mutagenesis. For example, in some embodiments, an antibody identified using the methods of the invention can be modified, to thereby modify the binding affinity of the antibody to flagellin.

The present invention also encompasses "conservative amino acid substitutions" in the sequences of the antibodies of the invention, i.e., nucleotide and amino acid sequence modifications which do not abrogate the binding of the antibody encoded by the nucleotide sequence or containing the amino acid sequence, to the antigen, i.e., flagellin. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an anti-flagellin antibody of the present invention is preferably replaced with another amino acid residue from the same class. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

The term "non-conservative amino acid substitution" refers to the substitution of an amino acid in one class with an amino acid from another class; for example, substitution of an Ala, a class II residue, with a class III residue such as Asp, Asn, Glu, or Gln.

Alternatively, in another embodiment, mutations (conservative or non-conservative) can be introduced randomly along all or part of an anti-flagellin antibody coding sequence, such as by saturation mutagenesis, and the resulting modified anti-flagellin antibodies can be screened for binding activity.

A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

Similarly, the consensus sequence for the CDRs of can be derived by optimal alignment of the CDR amino acid sequences of flagellin antibodies of the present invention.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "operably linked" refers to a nucleic acid sequence placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration to a subject, an antibody of the present invention, for example, a subject having an infection or disease associated with flagellin or predisposed to having such an infection or disease, in order to prevent, cure, delay, reduce the severity of, or ameliorate one or more symptoms of the infection or disease in order to prolong the survival of a subject beyond that expected in the absence of such treatment.

The terms "effective amount" and "therapeutically effective amount" as used herein, refers to that amount of an antibody thereof that binds flagellin, which is sufficient to effect treatment, prognosis or diagnosis of an infection or disease associated with flagellin, as described herein, when administered to a subject. A therapeutically effective amount will vary depending upon the subject and the infection or disease condition being treated, the weight and age of the subject, the severity of the infection or disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody of the present invention. Dosage regimens may be adjusted to provide the optimum therapeutic response. An effective amount is also one in which any toxic or detrimental effects (i.e., side effects) of an antibody are minimized and/or outweighed by the beneficial effects.

The term "patient" includes human and other mammalian subjects that receive either prophylactic or therapeutic treatment.

As used herein, the term "subject" includes any human or non-human animal. For example, the methods and compositions of the present invention can be used to treat a subject having a bacterial disease. In a particular embodiment, the subject is a human. The term "non-human animal" includes all vertebrates, e.g., mammals and non-mammals, such as non-human primates, sheep, dog, cow, chickens, amphibians, reptiles, etc.

The term "sample" refers to tissue, body fluid, or a cell from a patient or a subject. Normally, the tissue or cell will be removed from the patient, but in vivo diagnosis is also contemplated. Other patient samples, include urine, tear drops, serum, cerebrospinal fluid, feces, sputum, cell extracts etc.

The term "therapeutic agent" refers to any agent which acts in conjunction with or synergistically with the antibody to treat or prevent an infection-associated infection or disease. Therapeutic agents include, but are not limited to, chemotherapeutic agents, cytotoxic agents, anti-inflammatory agents, e.g., a steroidal or nonsteroidal inflammatory agent, or a cytotoxin antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The term "cytotoxin" or "cytotoxic agent" includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Various aspects of the invention are described in further detail in the following subsections.

II. Methods for Producing Anti-Flagellin Antibodies (i) Monoclonal Antibodies

Monoclonal antibodies of the invention can be produced using a variety of known techniques, such as those described in the examples, as well as the standard somatic cell hybridization technique described by Kohler and Milstein (1975) *Nature* 256: 495, viral or oncogenic transformation of B lymphocytes or phage display technique using libraries of human antibody genes. In particular embodiments, the antibodies are fully human monoclonal antibodies.

Accordingly, in one embodiment, a hybridoma method is used for producing an antibody that binds flagellin. In this method, a mouse or other appropriate host animal can be immunized with flagellin protein (or a fragment of flagellin) in order to elicit lymphocytes that produce or are capable of producing antibodies that will specifically bind to this antigen. Suitable flagellin protein can be obtained using a variety of methods, purified from a source, produced recombinantly or chemically synthesized. In a particular embodiment of the present invention, antibodies are raised against flagellin from *Salmonella* (Genbank Accession No. GI:1333832) (SEQ ID NO:39) or *Pseudomonas* (Genbank Accession No. GI:3386643) (SEQ ID NO:36).

Alternatively, lymphocytes may be immunized in vitro. Lymphocytes can then be fused with myeloma cells using a suitable fusing agent, such as polyethylene glycol, to form a hybridoma cell (Goding, Monoclonal Antibodies: Principles and Practice, pp. 59-103 (Academic Press, 1986)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In another embodiment, antibodies (and binding fragments thereof) that bind flagellin can be isolated from antibody phage libraries generated using the techniques described in, for example, McCafferty et al., *Nature*, 348:552-554 (1990). Clackson et al., *Nature*, 352:624-628 (1991), Marks et al., *J. Mol. Biol.*, 222:581-597 (1991) and Hoet et al (2005) *Nature Biotechnology* 23, 344-348; U.S. Pat. Nos. 5,223,409; 5,403, 484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Additionally, production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)), may also be used.

In a particular embodiment, the antibodies of the invention are fully human antibodies. Such antibodies can be produced using a variety of known methods, for example, the phage display technique described by Hoet et al., supra. This technique involves the generation of a human Fab library having a unique combination of immunoglobulin sequences isolated from human donors and having synthetic diversity in the heavy-chain CDRs is generated. The library is then screened for Fabs that bind to flagellin.

Additionally, fully human antibodies directed against flagellin can be generated using transgenic or transchromosomic mice carrying parts of the human immune system rather than the mouse system (see e.g., Lonberg, et al. (1994) Nature 368(6474): 856-859; Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.).

Other techniques for generating fully human antibodies of the invention include the use of a mouse that carries human immunoglobulin sequences on transgenes and transchomosomes, such as a mouse that carries a human heavy chain transgene and a human light chain transchromosome (see e.g., PCT Publication WO 02/43478 to Ishida et al.).

Still further, alternative transgenic animal systems expressing human immunoglobulin genes are available in the art and can be used to raise anti-flagellin antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-flagellin antibodies of the invention. For example, mice carrying both a human heavy chain transchromosome and a human light chain tranchromosome can be used; as described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise antibodies of the present invention.

In yet another embodiment, antibodies of the present invention can be prepared using a transgenic plant and/or cultured plant cells (such as, for example, tobacco, maize and duckweed) that produce such antibodies. For example, transgenic tobacco leaves expressing antibodies or antigen binding portions thereof can be used to produce such antibodies by, for example, using an inducible promoter (see, e.g., Cramer et al., Curr. Top. Microbol. Immunol. 240:95 118 (1999)). Also, transgenic maize can be used to express such antibodies and antigen binding portions thereof (see, e.g., Hood et al., Adv. Exp. Med. Biol. 464:127 147 (1999)). Antibodies can also be produced in large amounts from transgenic plant seeds including antibody portions, such as single chain antibodies (scFv's), for example, using tobacco seeds and potato tubers (see, e.g., Conrad et al., Plant Mol. Biol. 38:101 109 (1998)). Methods of producing antibodies or antigen binding portions in plants can also be found in, e.g., Fischer et al., Biotechnol. Appl. Biochem. 30:99 108 (1999), Ma et al., Trends Biotechnol. 13:522 7 (1995); Ma et al., Plant Physiol. 109:341 6 (1995); Whitelam et al., Biochem. Soc. Trans. 22:940 944 (1994) and U.S. Pat. Nos. 6,040,498 and 6,815,184.

The binding specificity of the antibodies of the present invention can be identified using any technique including those disclosed here, can be determined by immunoprecipitation or by an in vitro binding assay, such as radioimmunoassay (RIA) or enzyme-linked immunoabsorbent assay (ELISA). The binding affinity of a monoclonal antibody or portion thereof can be determined by the Scatchard analysis of Munson et al., Anal. Biochem., 107:220 (1980). Art recognized techniques can also be used to alter or optimize particular binding specificities and/or affinities (see, for example, Carter P J, Nature Reviews Immunology 6: 343-357 (2006)).

In certain embodiments, partial antibody sequences derived from antibodies of the invention may be used for producing structurally and functionally related antibodies. For example, antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332: 323-327; Jones, P. et al., 1986, Nature 321:522-525; Tamura et al., J Immunol., 2000 Feb. 1; 164(3):1432-41; and Queen, C. et al., 1989, Proc. Natl. Acad. See. U.S.A. 86:10029-10033). Such framework sequences can be obtained from public DNA databases that include germline antibody gene sequences.

Thus, in one embodiment, one or more structural features of the particular anti-flagellin antibodies of the invention are used to create structurally related anti-flagellin antibodies that retain the functional properties of the parent antibodies of the invention, such as binding to the same epitope or overlapping epitopes bound by the anti-flagellin antibodies exemplified herein, as well as cross-competing for antigen-binding with the anti-flagellin antibodies exemplified herein.

In another embodiment, one or more structural features of the particular antibodies of the invention are used to create structurally related anti-flagellin antibodies that retain functional properties of the parent antibodies of the invention, such as (i) neutralizing flagellin; (ii) inhibiting the activity of flagellin; (iii) cross-reacting with a broad spectrum of gram-negative bacteria; (iv) inhibiting bacterial invasion into susceptible epithelial cells; (v) binding to flagellin with an affinity of at least $10^6$ $M^{-1}$; (vi) reducing the symptoms of an enterobacterial infection or IBD in a subject; (vii) reducing the extent and severity of flagellin-induced tissue injury; (viii) reducing flagellin-stimulated neutrophil infiltration; (ix)

decreasing colonic mucosal congestion, erosion and hemorrhagic ulcerations associated with IBD; (x) inhibiting or decreasing the production of mediators (e.g., MDA, IL-1β, TNFα, MIP-1, MIP-2 and IL-8); and (xi) counteracting a reduction in body weight associated with IBD.

Methods known in the art for creating such structural and functional related antibodies include, for example, Marks et al. (*Biotechnology* (N Y). 1992 July; 10(7):779-83) (monoclonal antibodies diversification by shuffling light chain variable regions, then heavy chain variable regions with fixed CDR3 sequence changes), Jespers et al., (*Biotechnology* (N Y). 1994 September; 12(9):899-903) (selection of human antibodies from phage display repertoires to a single epitope of an antigen), Sharon et al., (*Proc Natl Acad Sci USA*. 1986 April; 83(8):2628-31) (site-directed mutagenesis of an invariant amino acid residue at the variable-diversity segments junction of an antibody); Casson et al., (*J Immunol*. 1995 Dec. 15; 155(12):5647-54) (evolution of loss and change of specificity resulting from random mutagenesis of an antibody heavy chain variable region).

In one embodiment, one or more CDR regions of antibodies of the invention can be combined recombinantly with known human framework regions and CDRs to create additional, recombinantly-engineered, anti-flagellin antibodies of the invention. The heavy and light chain variable framework regions can be derived from the same or different antibody sequences.

It is well known in the art that antibody heavy and light chain CDR3 domains play a particularly important role in the binding specificity/affinity of an antibody for an antigen. See, for example, Brummel et al. (*Biochemistry.* 1993 Feb. 2; 32(4):1180-7), which showed that binding activity is retained in a wide range of CDR3 mutants for each of the four residues that directly hydrogen bond to the antigen. Only Gly$^{102}$ could not be replaced without significant loss of affinity (see also, Hall et al., *J. Immunol.*, 149:1605-1612 (1992); Polymenis et al., *J. Immunol.*, 152:5318-5329 (1994); Jahn et al., *Immunobiol.*, 193:400-419 (1995); Klimka et al., *Brit. J Cancer,* 83:252-260 (2000); Beiboer et al., *J. Mol. Biol,* 296:833-849 (2000); Rader et al., *Proc. Natl. Acad. Sci. USA,* 95:8910-8915 (1998); Barbas et al., *J. Am. Chem. Soc.,* 116:2161-2162 (1994); Ditzel et al., *J. Immunol.,* 157:739-749 (1996)). Accordingly, in certain embodiments, antibodies can be prepared to include the heavy and/or light chain CDR3s of the antibodies of the present invention (e.g., SEQ ID NOs:9 and 10 and/or SEQ ID NOs: 15 and 16). The antibodies can further include the heavy and/or light chain CDR2s of the antibodies of the present invention (e.g., SEQ ID NOs:7 and 8 and/or SEQ ID NOs:13 and 14). The antibodies can further include the heavy and/or light chain CDR1s of the antibodies of the present invention (e.g., SEQ ID NOs:5 and 6 and/or SEQ ID NOs:11 and 12).

The CDR1, 2, and/or 3 regions of the engineered antibodies described above can comprise the exact amino acid sequence(s) as those disclosed herein (e.g., CDRs of monoclonal antibody 741 ("mAb 741") and monoclonal antibody 763 ("mAb 763"), set forth in SEQ ID NOs:5, 7, 9, 11, 13, 15 and 6, 8, 10, 12, 14 and 16, respectively). However, the ordinarily skilled artisan will appreciate that some deviation from the exact CDR sequences may be possible while still retaining the ability of the antibody to bind flagellin effectively (e.g., conservative amino acid substitutions). Accordingly, in another embodiment, the engineered antibody may be composed of one or more CDRs that are, for example, 90%, 95%, 98%, 99% or 99.5% identical to one or more CDRs of mAbs 741 and 763.

In another embodiment, one or more residues of a CDR may be altered to modify binding to achieve a more favored on-rate of binding. Using this strategy, an antibody having ultra high binding affinity of, for example, $10^{10}$ M$^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

In addition to, or instead of, modifications within the CDRs, modifications can also be made within one or more of the framework regions, FR1, FR2, FR3 and FR4, of the heavy and/or the light chain variable regions of an antibody, so long as these modifications do not eliminate the binding affinity of the antibody.

In another embodiment, it may be desirable to modify the antibody of the invention with respect to effector function, so as to enhance the effectiveness of the antibody in treating an inflammatory bowel disease in a subject, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

Also encompassed by the present invention are bispecific antibodies and immunoconjugates, as discussed below.

(ii) Bispecific Antibodies

Bispecific antibodies of the present invention include at least one binding specificity for flagellin and at least one binding specificity for another target (such as an immune cell (e.g., an Fc receptor on an immune cell) or a second epitope on flagellin). Bispecific antibodies can be prepared as full length antibodies or antibody fragments (e.g. F(ab')$_2$ bispecific antibodies).

Methods for making bispecific antibodies are well known in the art. For example, production of full length bispecific antibodies can be based on the coexpression of two immunoglobulin heavy chain-light chain pairs, where the two chains have different specificities (see, e.g., Millstein et al., *Nature,* 305:537-539 (1983)). Further details of generating bispecific antibodies can be found, for example, in Suresh et al., *Methods in Enzymology,* 121:210 (1986) and in Brennan et al., *Science,* 229: 81 (1985), which describes a chemical linkage process for making bispecific antibodies. Various techniques for making and isolating bispecific antibody fragments directly from recombinant cell culture have also been described. For example, bispecific antibodies have been produced using leucine zippers (see, e.g., Kostelny et al., *J. Immunol.,* 148(5):1547-1553 (1992)). Another strategy for making bispecific antibody fragments by the use of single-chain Fv (sFv) dimers has also been reported (see, e.g., Gruber et al., *J. Immunol.,* 152:5368 (1994)).

(iii) Immunoconjugates

In another aspect, the present invention provides immunoconjugates that bind to flagellin and target therapeutic agents (e.g., a toxin) to particular classes of bacteria. Immunoconjugates can be formed by conjugating (e.g., chemically linking or recombinantly expressing) antibodies of the invention to suitable therapeutic agents. Suitable agents include, for example, a cytotoxic agent, a toxin (e.g. an enzymatically active toxin of bacterial, fungal, plant or animal origin, or fragments thereof), and/or a radioactive isotope (i.e., a radioconjugate). Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. A variety of radionuclides are available for the production of radioconjugated anti-flagellin antibodies. Examples include $^{212}$Bi, $^{131}$I, $^{131}$In, $^{90}$Y and $^{186}$Re.

Immunoconjugates of the invention can be made using a variety of bifunctional protein coupling agents such as N-succinimidyl-3-(2-pyridyldithiol) propionate (SPDP), iminothiolane (IT), bifunctional derivatives of imido esters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody (see, e.g., WO94/11026).

III. Methods for Screening Anti-Flagellin Antibodies

Subsequent to producing antibodies that bind to flagellin, the antibodies can be screened and selected for various properties, such as (i) their effect on bacterial invasion into susceptible epithelial cells, (ii) inhibition of flagellin-stimulated NO or IL-8 production from epithelial cells, (iii) bacterial opsonophagocytosis, (iv) macrophage ingestion of bacteria, (v) superoxide production, (vi) ability to neutralize flagellin, (vii) ability to inhibit the activity of flagellin, (viii) cross-reactivity with a broad spectrum of gram-negative bacteria, (ix) ability to inhibit bacterial invasion into susceptible epithelial cells, (x) ability to bind to flagellin with an affinity of at least $10^6$ M$^{-1}$, (xi) capability of reducing the symptoms of an enterobacterial infection or IBD in a subject, (xii) capability of reducing the extent and severity of flagellin-induced tissue injury, (xiii) capability of reducing flagellin-stimulated neutrophil infiltration; (xiv) capability of decreasing colonic mucosal congestion, erosion and hemorrhagic ulcerations associated with IBD; (xv) capability of inhibiting or decreasing the production of mediators (e.g., MDA, IL-1β, TNFα, MIP-1, MIP-2 and IL-8); and (xvi) capability of counteracting a reduction in body weight associated with IBD, using a variety of assays that are well known in the art. Assays for screening for such properties include the assays exemplified and described herein, as well as those well known in the art, such as binding to immobilized recombinant or bacterial flagellin on ELISA, binding to recombinant or bacterial extracts on SDS-PAGE, affinity binding determinations to purified antigens by BIACore analysis.

Antibodies or antigen binding portions thereof that bind to the same or overlapping epitopes as one or more antibodies of the present invention can also be identified using standard techniques known in the art and described herein. For example, in order to screen for antibodies which bind to the same or an overlapping epitope on flagellin bound by an antibody of interest, a cross-blocking assay, such as that described in *Antibodies*, A Laboratory Manual, Cold Spring Harbor Laboratory, Ed Harlow and David Lane (1988), can be performed.

IV. Pharmaceutical Compositions

In another aspect, the present invention provides compositions, e.g., a pharmaceutical composition, containing one or a combination of antibodies of the invention thereof, of the present invention, formulated together with a pharmaceutically acceptable carrier. In one embodiment, the compositions include a combination of multiple (e.g., two or more) isolated antibodies of the invention, which bind different epitopes on flagellin.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutical compositions of the invention can be administered alone or in combination therapy, i.e., combined with other agents. For example, the combination therapy can include a composition of the present invention with at least one or more additional therapeutic agents, such as chemotherapeutic agents. The pharmaceutical compositions of the invention can also be administered in conjunction with radiation therapy.

Pharmaceutical compositions of the invention can administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the human antibodies of the invention may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Therapeutic compositions of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the antibodies of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, antibodies of the present invention and/or the pharmaceutical compositions thereof, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. No. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) Immunomethods 4:273.

V. Methods of Using Anti-Flagellin Antibodies

The present invention provides methods of using antibodies that bind to and neutralize bacterial flagellin in a variety of therapeutic and diagnostic applications.

Suitable diseases that can be treated and/or diagnosed using the antibodies provided herein include, for example, IBD, Ulcerative Colitis and Crohn's Disease, as well as infectious diseases, including, but not limited to, gram negative bacterial infections (e.g., enterobacterial infections), sepsis, septic shock, Anthrax (by the bacterium *Bacillus anthracis*), Bacterial Meningitis (caused by a variety of bacteria, including, but not limited to, *Neisseria meningitides, Streptococcus pneumoniae, Listeria monocytogenes, Pseudomonas aeruginosa, Staphylococcus aureus, Streptococcus agalactiae* and *Haemophilus influenzae*), Botulism (caused by bacterium *Clostridium botulinum*), Brucellosis (caused by bacteria of the genus *Brucella*), Campylobacteriosis (caused by bacteria of the genus *Campylobacter*), Cat Scratch Disease (caused by *Bartonella henselae* and *Bartonella clarridgeiae*), Cholera (caused by the bacterium *Vibrio cholerae*), Diphtheria (caused by *Corynebacterium diphtheriae*), Epidemic Typhus (causative organism is *Rickettsia prowazekii*), Impetigo (caused by several bacteria, including, *Staphylococcus aureus* and *Streptococcus pyogenes*), Legionellosis (caused by bacteria belonging to the genus *Legionella*), Leprosy (Hansen's Disease) (caused by the bacterium *Mycobacterium leprae*), Leptospirosis (caused by spirochaetes of the genus *Leptospira*), Listeriosis (caused by the bacterium *Listeria monocytogenes*), Lyme Disease (caused by spirochete bacteria from the genus *Borrelia*), Melioidosis (caused by the bacterium *Burkholderia pseudomallei*), MRSA infection (caused by *Staphylococcus aureus*), Nocardiosis (bacterium of the genus *Nocardia*, most commonly *Nocardia asteroides* or *Nocardia brasiliensis*), Pertussis (Whooping Cough)

(caused by the bacterium *Bordetella pertussis*), Plague (caused by the enterobacteria *Yersinia pestis*), Pneumococcal pneumonia (caused by a variety of bacteria, including, but not limited to, *Streptococcus pneumoniae*, *Staphylococcus aureus*, *Haemophilus influenzae*, *Klebsiella pneumoniae*, *Escherichia coli*, *Pseudomonas aeruginosa*, *Moraxella catarrhalis*, *Chlamydophila pneumoniae*, *Mycoplasma pneumoniae*, and *Legionella pneumophila*), Psittacosis (caused by a bacterium called *Chlamydophila psittaci*), Q fever (caused by infection with *Coxiella burnetii*), Rocky Mountain Spotted Fever (RMSF) (by *Rickettsia rickettsii*), Salmonellosis (caused by bacteria of the genus *Salmonella*), Scarlet Fever, Shigellosis (caused by bacteria of the genus *Shigella*), Syphilis (caused by *Treponema pallidum*), Tetanus (*Clostridium tetani*), Trachoma, Tuberculosis (caused by mycobacteria, mainly *Mycobacterium tuberculosis*), Tularemia (by the bacterium *Francisella tularensis*), Typhoid Fever (caused by the bacterium *Salmonella typhi*), and Urinary Tract Infections (caused by bacteria such as *Escherichia coli*, *Staphylococcus saprophyticus*, *Proteus mirabilis*, *Klebsiella pneumoniae*, *Enterobacter* spp., *Pseudomonas* and *Enterococcus*).

Antibodies of the present invention are particularly useful for treating enterobacterial infections, and can be selected for broad reactivity with multiple entobacterial strains, such *Alishewanella*, *Alterococcus*, *Aquamonas*, *Aranicola*, *Arsenophonus*, *Azotivirga*, *Blochmannia*, *Brenneria*, *Buchnera*, *Budvicia*, *Buttiauxella*, *Cedecea*, *Citrobacter*, *Dickeya*, *Edwardsiella*, *Enterobacter*, *Erwinia*, *Escherichia*, *Ewingella*, *Grimontella*, *Hafnia*, *Klebsiella*, *Kluyvera*, *Leclercia*, *Leminorella*, *Moellerella*, *Morganella*, *Obesumbacterium*, *Pantoea*, *Pectobacterium*, *Candidatus Phlomobacter*, *Photorhabdus*, *Plesiomonas*, *Pragia Proteus*, *Providencia*, *Rahnella*, *Raoultella*, *Salmonella*, *Samsonia*, *Serratia*, *Shigella*, *Sodalis*, *Tatumella*, *Trabulsiella*, *Wigglesworthia*, *Xenorhabdus*, *Yersinia* and *Yokenella*.

The antibodies can be administered alone or with other therapeutic agents, which act in conjunction with or synergistically with the antibodies, to treat diseases. Such therapeutic agents include, for example, toxins, chemotherapeutic agents, small molecules and radiation Also within the scope of the present invention are kits comprising antibodies and antigen binding portions thereof of the invention which optionally include instructions for use in treating a disease associated with flagellin. The kits may include a label indicating the intended use of the contents of the kit. The term label includes any writing, marketing materials or recorded material supplied on or with the kit, or which otherwise accompanies the kit.

Other embodiments of the present invention are described in the following Examples.

The present invention is further illustrated by the following examples which should not be construed as further limiting. The contents of Sequence Listing, figures and all references, patents and published patent applications cited throughout this application are expressly incorporated herein by reference.

EXAMPLES

Example 1

Generation of Anti-Flagellin Antibodies

Antigen Construction

The gene fragment corresponding to amino acids 1-156 of the flagellin gene of *Salmonella muenchen* was used as an antigen (Genbank Accession No. GI:47233) (SEQ ID NO:41):

```
aaggaaaagatcatggcacaagtcattaatacaaacagcctgtcgctgtt
gacccagaataacctgaacaaatcccagtccgctctgggcaccgctatcg
agcgtctgtcttccggtctgcgtatcaacagcgcgaaagacgatgcggca
ggtcaggcgattgctaaccgtttcaccgcgaacatcaaaggtctgactca
ggcttcccgtaacgctaacgacggtatctccattgcgcagaccactgaag
gcgcgctgaacgaaatcaacaacaacctgcagcgtgtgcgtgaactggcg
gttcagtctgctaacggtactaactcccagtctgaccttgactctatcca
ggctgaaatcacccagcgtctgaacgaaatcgaccgtgtatccggtcaga
ctcagttcaacggcgtgaaagtcctggcgcaggacaacaccctgaccatc
caggttggtgccaacgac
```

The antigen was prepared by expression of a cDNA clone obtained by PCR amplification of DNA from *S. muenchen* using a sense primer designated IS (5'-CGC GGATCCCAATGGCACAAGTCATTAATACAAACA) (SEQ ID NO:17) and an antisense primer designated 468A (5'-TCCG CTCGAGTTAAATAGTTTCACCGTCGTTGGCACC) (SEQ ID NO: 18). Underlined nucleotides represent adaptor sequences added to the ends of primers to maintain proper reading frame and facilitate cloning (BamHI recognition sites on sense primers and XhoI sites on antisense primers). The template DNA for PCR was plasmid CL402, a clone of pBR322 containing a 3.8-kb EcoRI fragment of *S. muenchen* chromosomal DNA that harbors the 1.5-kb flagellin gene. PCR-generated flagellin DNA were digested with BamHI plus XhoI, gel purified, and subcloned into the BamHI/XhoI sites at the 3' end of the His tag in expression vector pET 30C (Novagen, San Diego, Calif.). The correct reading frame and integrity of subcloned DNA was verified by DNA sequence analysis. The recombinant plasmids were then introduced into *Escherichia coli* BL21 (DE3) (Novagen) by transformation and selected in the presence of kanamycin (50 ug/ml).

Expression and Purification of Recombinant Antigen

A single colony of *E. coli* containing the recombinant plasmid was grown at 37° C. in Luria broth containing 50 ug/ml kanamycin to an A600 of 0.5 and then induced for 3 h with 0.5 mM isopropyl-1-thio-b-D-galactopyranoside. Following induction, bacteria were harvested and washed with phosphate-buffered saline (PBS, pH 7.2). Cell-free lysates were prepared in 6 M guanidine chloride containing 5 mM imidazole and 0.1% Nonidet P-40 (binding buffer). After removing the insoluble material by centrifugation, the lysate was applied to a nickel-nitrilotriacetic acid-agarose (Qiagen, Valencia, Calif.) column, washed extensively with binding buffer, and then eluted with binding buffer containing 200 mM imidazole. The purified proteins were extensively dialyzed against PBS, and protein concentrations were determined by the Bradford method. The final proteins were analyzed by 10% SDS-PAGE and visualized with Coomassie Blue staining to assess protein purity, integrity, and concentration.

Immunization

Female BALB/c mice of 12 week old were immunized with 50 ug of fusion protein in complete adjuvant. On day 14, 28 and 42 mice were boosted with 50 ug of protein in incomplete adjuvant. Three days after final boost, spleen cells will be prepared for fusion with SP2/O myeloma cells (ATCC). Antibody titer in serum was measured by ELISA and using recombinant *S. muenchen* flagellin as antigen.

Preparation of Monoclonal Antibodies

Anti-flagellin monoclonal antibodies were produced using previously described methods (Harlow and Lane, Antibodies, CSH laboratories). Spleens from immunized mice were broken apart with sterile forceps and passed through a sterile stainless-steel strainer by pressing the spleen tissue with the glass plunger. Splenocytes were collected, washed once in serum-free DMEM medium and then fused with SP2/O myeloma cells using sterile PEG (polyethylene glycol) solution. After fusion cells were seeded in 96-well microtiter plates and selected against HAT medium. Hybridoma culture supernatants were screened by ELISA using 96 well plates coated with recombinant flagellin and amplified the positive ones and tested for Ig-subclass (Southern Biotechnology Associates). The candidate hybridoma lines producing IgG subclass were selected and cloned by limited dilution.

Purification of Monoclonal Antibodies

Murine monoclonal antibodies to flagellin were purified using standard immunology techniques. In brief, hybridoma cells were grown in roller bottles for 14 days in BD medium and tissue culture supernatants wee collected. Antibodies were further purified by passing over a 10 ml protein G-sepharose affinity column, washed extensively with PBS, and eluted with 0.1 M glycine (pH 2.5). After dialysis of the eluate against PBS, antibodies titers were tested by ELISA and tested the purity by SDS-polyacrylamide gels.

Example 2

Generation of Human Monoclonal Antibodies

Human peripheral blood lymphocytes (PBL's) were obtained by leukophoresis from donors positive for anti-Salmonella muenchen IgG. PBL's were separated on a Ficoll-Hypaque gradient, washed twice, counted and resuspended in PBS. BALB/c mice were exposed to split dose total body irradiation (4 Gy followed 3 days later by 10-11 Gy) from a gamma beam 60 Co source with a focal skin distance of 75 cm and a dose rate of 0.7 Gy/min. Following irradiation, each recipient mouse was immediately injected i.v. with 4–6×10⁶ of SCID/NOD bone marrow cells and i.p. with 100×10⁶ human PBL's. These reconstituted mice were thereafter immunized once i.p. with 2.5 mcg recombinant SM flagellin protein (a/a 1-156) in 0.15% Aluminum hydroxide gel. Fourteen days later, animals were bled from the retro-orbital vein and screened for IgG reactivity to coated SM flagellin protein on ELISA plates and determination of human IgG. Spleen cells from mice that exhibited positive screening of plasma were harvested and taken for fusion with the human-mouse heteromyeloma HMMA2.1 TG/020 at a ratio of 3:1. Fusion was performed with 50% w/v PEG 1500 and fused cells seeded at a concentration of 30,000 cells per well in a 96 well U-bottom, microtiter plate in complete RPMI medium containing hypoxanthine, aminopterin and thymidine (HAT) supplement. Cells were fed with fresh HAT medium 1 week later. Two weeks after fusion, supernatants were harvested for ELISA of human IgG and anti-SM flagellin reactivity. Medium was replaced with fresh hypoxanthine, thymidine (HT)-containing medium. Hybridoma cultures secreting specific anti-SM flagellin IgG were cloned by limiting dilution at 0.5 cells per well in a 96 well U bottom microtiter plate. One clone, INO-763, repeatedly demonstrated the highest binding as well as being stable.

Example 3

Hybridoma Sequencing mRNA was extracted from two hybridoma cell lines, the first (mAb 741) expressing a murine antibody, and the second (mAb 763) expressing a human antibody. The mRNA was reverse transcribed and antibody specific transcripts were PCR amplified. PCR products were cloned for determination of the nucleotide and amino acid sequences of the heavy and light chain variable regions of both antibodies. Heavy chain variable region mRNA was amplified using a set of six degenerate primer pools (HA to HF) and light chain variable region mRNA was amplified using a set of eight degenerate primer pools (LA to LH).

mAb 741 Heavy Chain

Strong DNA bands of approximately the expected size were observed in primer pools HB and HE. DNA from each band was purified and cloned, and four clones were sequenced. All four clones aligned to give a functional, rearranged heavy chain (Table 1, FIG. 1).

mAb 741 Light Chain

Strong DNA bands of the expected size were observed in primer pools LB, LC and LG. DNA from each band was purified and cloned, and a total of nine clones were sequenced. Six of the clones were found to align with the well described aberrant kappa transcript found in some hybridomas and three clones aligned to give a functional, rearranged light chain (Table 1, FIG. 2).

TABLE 1

Antibody Sequence Analysis[1]

|  | VH Chain | VK Chain |
|---|---|---|
| CDR 1 Length | 5 amino acids | 10 amino acids |
| CDR 2 Length | 17 amino acids | 7 amino acids |
| CDR 3 Length | 4 amino acids | 9 amino acids |
| Mouse Germline[2] | J558.51 (93%) | Kn4 (96%) |
| Closest Human Germline[2] | VH1-24 (65%) | A26 (64%) |

[1]CDR definitions and sequence numbering according to Kabat.
[2]Germline ID(s) indicated followed by % homology.

mAb 763 Heavy Chain

A weak DNA band of the expected size was observed in primer pool HA. DNA from this band was purified and cloned, and three clones were sequenced. All clones aligned to give a functional, rearranged heavy chain (Table 2, FIG. 3).

mAb 763 Light Chain

Strong DNA bands of the expected size were observed in primer pools LB, LC and LG, and a weak band was observed in pool LH. DNA from each band was purified and cloned and a total of eighteen clones were sequenced. Twelve of the clones (from pools LB, LC and LG) aligned with the well described aberrant kappa transcript found in some hybridomas. Five clones (from pool LH) aligned to give a functional, rearranged light chain (Table 2, FIG. 4). Pool LH primers are specific for lambda light chains and this was confirmed by the sequence analysis.

TABLE 2

Antibody Sequence Analysis[1]

|  | VH Chain | Vλ Chain |
|---|---|---|
| CDR 1 Length | 5 amino acids | 11 amino acids |
| CDR 2 Length | 17 amino acids | 7 amino acids |
| CDR 3 Length | 10 amino acids | 11 amino acids |
| Mouse Germline[2] | N/A | N/A |
| Closest Human Germline[2] | VH3-23 (87%) | V2-17 (92%) |

[1]CDR definitions and sequence numbering according to Kabat.
[2]Germline ID(s) indicated followed by % homology.

Example 4

Generation of Chimeric Antibodies

As described above in Example 3, variable regions from the murine 741 anti-flagellin antibody were successfully cloned and sequenced. These murine variable region genes were then combined with human IgG1 heavy chain and kappa light chain constant regions and expressed in NS0 cells to produce a chimeric anti-flagellin antibody (referred to herein as mAb 741C or chimeric mAb 741C) as follows.

A. Expression of Chimeric Antibody

The variable regions of mAb 741 were transferred to appropriate expression vector (e.g., an Antitope expression vector) system for IgG1 heavy chains. NS0 cells were transfected via electroporation and selected using methotrexate (Sigma Catalogue No. M8407-500MG). A number of methotrexate resistant colonies were identified and cell lines positive for IgG expression were expanded. After several passages, the cell line with the highest level of IgG expression (mAb 741-4G4) was selected and expanded. Chimeric IgG1 from the mAb 741-4G4 stable cell line was purified from cell culture supernatants on a Protein A sepharose column (GE Healthcare Catalogue No. 110034-93). The concentration of the antibody was calculated by UV absorption based upon a calculated molar extinction coefficient such that Ec(0.1%) at 280 nm=1.41. 20 mg of the expressed chimeric antibody was purified. The purified chimeric antibody was analyzed by SDS-PAGE.

B. Binding of the Chimeric Antibody to Flagellin

The binding of chimeric mAb 741C to flagellin was assessed by competition ELISA. A dilution series of NS0-derived chimeric IgG1 or mouse control antibody from 20 µg/ml to 0.01 g/ml was premixed with a constant concentration of biotinylated control antibody (0.6 µg/ml) before incubating for 1 hour at room temperature on a Nunc Immulo MaxiSorp 96 well flat bottom microlitre plate (Fisher Catalogue No. DIS-971-030J) pre-coated with 100 µl 1 µg/ml *Salmonella muenchen* Flagellin (supplied by Inotek) per well. The binding of the biotinylated mAb was determined by detection with streptavidin-HRP (Sigma Catalogue No. S5512) and OPD substrate (Sigma Catalogue No. P9187-SOSET) and absorbance at 490 nm was measured on a Dynex Technologies MRX TC II plate reader. The results obtained (FIG. 5) show that the chimeric mAb 741C and mouse control antibodies have similar binding profiles, with IC50 values of 1.59 µg/ml and 1.90 µg/ml respectively.

Example 5

Generation of Humanized Antibodies

Antibodies of the invention can also be humanized using a variety of known techniques known in the art, such as those taught in U.S. Pat. No. 5,225,539 to Winter, and U.S. Pat. Nos. 5,530,101; 5,585,089; 5,693,762 and 6,180,370 to Queen et al., the substance of which is incorporated herein by reference. Additionally, the antibodies of the invention can be humanized using composite human antibody technologies, as described below.

A. Design of Humanized Heavy and Light Chains

The sequences of mAb 741 (or other anti-flagellin antibodies) heavy and light chain variable regions can be analyzed to identify CDRs, unusual amino acids and residues critical to binding as follows.

First, protein models of the murine antibody variable regions can be generated using existing antibody structures as templates. Structural information from the protein model can then be used to identify and compare residues critical for antibody conformation and binding with structurally equivalent residues from existing antibody structures and sequence databases. These amino acids can then be candidates for inclusion in one or more variants of the final humanized sequences.

Segments of monoclonal antibody heavy and light chain variable region amino acid sequences can then be compared with corresponding segments of human variable region sequences in order to identify potential heavy and light chain human sequences for possible inclusion in the humanized sequences.

A series of at least ten of each humanized heavy and light chain variable regions can then be designed entirely from segments of human variable region sequences. Alternative variants will differ in the inclusion of residues which might be critical to restoration of the original monoclonal antibody binding efficiency with the objective that the number of alterations in the frameworks needed to restore binding efficiency will be kept to the minimum and generation of T-cell epitopes avoided. Potential T cell epitopes as determined by in silico methods can be considered in the selection of alternative variants.

B. Construction of Humanized Heavy and Light Chains

Humanized variable regions can be constructed by PCR-ligation of long synthetic oligonucleotides. The initial heavy and light chain variable region genes can be used as templates for construction of additional sequences by mutagenesis using overlapping PCR with mutagenic oligonucleotide primers. Restriction enzyme sites can then be engineered upstream and downstream of each of the variable heavy and light chains for cloning into the appropriate expression vector (e.g., an Antitope expression vector). The entire DNA sequence can be confirmed to be correct for each modified variable region cassette.

C. Construction of Expression Plasmids Encoding Humanized Antibodies with Human Constant Regions At least ten humanized variable regions can be transferred into mammalian expression vectors as follows. First, the DNA sequences for each variable region can be inserted into mammalian expression vectors between an upstream cytomegalovirus immediate/early promoter/enhancer (CMV-ie) plus the immunoglobulin signal sequence and a downstream the immunoglobulin constant region. The heavy chain vector includes a genomic human IgG constant region of choice (IgG1, or IgG4) and the dhfr gene for selection in mammalian cells. The light chain vector includes the genomic human κ constant region.

DNA samples can then be prepared for transfection into mammalian cells. The humanized antibody heavy and light chain-encoding plasmids can be co-transfected into mammalian cells by electroporation.

D. Generation of Humanized Antibody-Producing Cell Lines and Selection of Lead Humanized Antibody Individual heavy and light chain plasmids can be paired in order to produce a final series of antibodies combining variant humanized variable region sequences. These combinations may also include chimeric heavy and light chains in order to determine the effects of individual modified humanized chains on binding efficiency.

Heavy and light chain plasmid DNA pairs can then be transfected into mammalian cells by electroporation, stable cell lines can be selected and tested for antibody production. Cell lines producing humanized antibodies comprising combinations of heavy and light chains can then be expanded and antibody samples (typically 100 ug) purified.

Antibodies can then be tested in a binding assay in order to determine the humanized best antibody lead. The entire coding sequence of the lead humanized antibody can then be subcloned into an appropriate mammalian expression vector.

Example 6

Anti-Flagellin Monoclonal Antibodies Are Protective in a Murine DNBS-Induced Colitis Model The following materials and methods were utilized in each of the following studies presented within this example:

Animals

The study was carried out in 6-8 weeks old (25-30 g) CD1 male mice (Harlan Nossan Udine, Italy). The animals were housed in a controlled environment and provided with standard rodent chow and water. Animal care was in compliance with Italian regulations on protection of animals used for experimental and other scientific purposes (D.M. 116192) as well as with the EEC regulations (O.J. of E.C. L 358/1 Dec. 18, 1986).

Administration of Antibodies

All monoclonal antibodies were administered by intraperitoneal injection one time only at 60 min prior to the DNBS challenge. In all the groups of animals, no evidence for lethargy or irritation was observed during the experimental time frame.

Induction of Experimental Colitis

Colitis was induced with a very low dose of DNBS (4 mg per mouse) by using a modification of the method first described in mice. In preliminary experiments, this dose of DNBS was found to induce reproducible colitis without mortality. Mice were anesthetized by Enflurane. DNBS (4 mg in 100 μl of 50% ethanol) was injected into the rectum through a catheter inserted 4.5 cm proximally to the anus. Carrier alone (100 μl of 50% ethanol) was administered in control experiments. Thereafter, the animals were kept for 15 minutes in a Trendelenburg position to avoid reflux. After colitis and sham-colitis induction, the animals were observed for 3 days. On Day 4, the animals were weighed and anaesthetized with chloral hydrate, and the abdomen was opened by a midline incision. The colon was removed, freed from surrounding tissues, opened along the antimesenteric border and processed for histology.

Evaluation of Colon Damage

After its removal, the colon was gently rinsed with saline solution, opened by a longitudinal incision, and immediately examined under a microscope. The visible colonic damage was assessed by a scoring system as previously described (Wallace et al., 1992).

Optical Microscopy

After fixation for 1 week at room temperature in Dietrich solution (14.25% ethanol, 1.85% formaldehyde, 1% acetic acid), samples were dehydrated in graded ethanol and embedded in Paraplast (Sherwood Medical, Mahwah, N.J.). Thereafter, 7-μm sections were deparaffinized with xylene, stained with hematoxylin-eosin and observed in a Dialux 22 Leitz (Wetziar, Germany) microscope. In order to have a quantitative estimation of colon damage, section (n=6 for each animals) was scored by an independent observer blinded to the experimental protocol. The following morphological criteria were considered: score 0, no damage; score 1 (mild), focal epithelial edema and necrosis; score 2 (moderate), diffuse swelling and necrosis of the villi; score 3 (severe), necrosis with presence of neutrophil infiltrate in the submucosa; score 4 (highly severe), widespread necrosis with massive neutrophil infiltrate and hemorrhage.

Myeloperoxidase Activity

Myeloperoxidase activity, an indicator of polymorphonuclear leukocyte accumulation, was determined. At the specified time following the intracolonic injection of DNBS, colon tissues were obtained and weighed. Each piece of tissue was homogenised in a solution containing 0.5% hexa-decyl-trimethyl-ammonium bromide dissolved in 10 mM potassium phosphate buffer (pH 7) and centrifuged for 30 min at 20,000×g at 4° C. An aliquot of the supernatant was then allowed to react with a solution of tetra-methyl-benzidine (1.6 mM) and 0.1 mM $H_2O_2$. The rate of change in absorbance was measured spectrophotometrically at 650 nm. Myeloperoxidase activity was defined as the quantity of enzyme degrading 1 μmol of peroxide min m at 37° C. and was expressed in Upper gram weight of wet tissue.

Reagents

All other reagents used were purchased from Sigma Chemical Company (Mlan, Italy).

Data Analysis

All values in the figures and text are expressed as mean±standard error (S.E.M.) of the mean of n observations. For the in vivo studies n represents the number of animals studied. In the experiments involving histology, the figures shown are representative of at least three experiments performed on different experimental days. The results were analyzed by one-way analysis of variance followed by a Bonferroni post-hoc test for multiple comparisons. A P-value less than 0.05 was considered significant.

A. Effects of mAb 763 at 20 (mg/kg) Versus DNBS-Induced Colitis

1. Experimental Groups: Animals were randomly divided into 5 groups (n=15 for each group):

| Group | DNBS | Treatment | Dosing |
| --- | --- | --- | --- |
| 1 | No | Sham-vehicle | 0.2 ml vehicle i.p. (saline solution) |
| 2 | Yes | Control-Vehicle | 0.2 ml vehicle i.p. (saline solution) |
| 3 | Yes | mAb 763 | 20 mg/kg i.p. |
| 4 | Yes | mAb CBH2 | 20 mg/kg i.p. |
| 5 | Yes | Infliximab | 5 mg/kg i.p. |

2. Effects of mAb 763 Treatment on the Degree of Colitis

Figure 6:
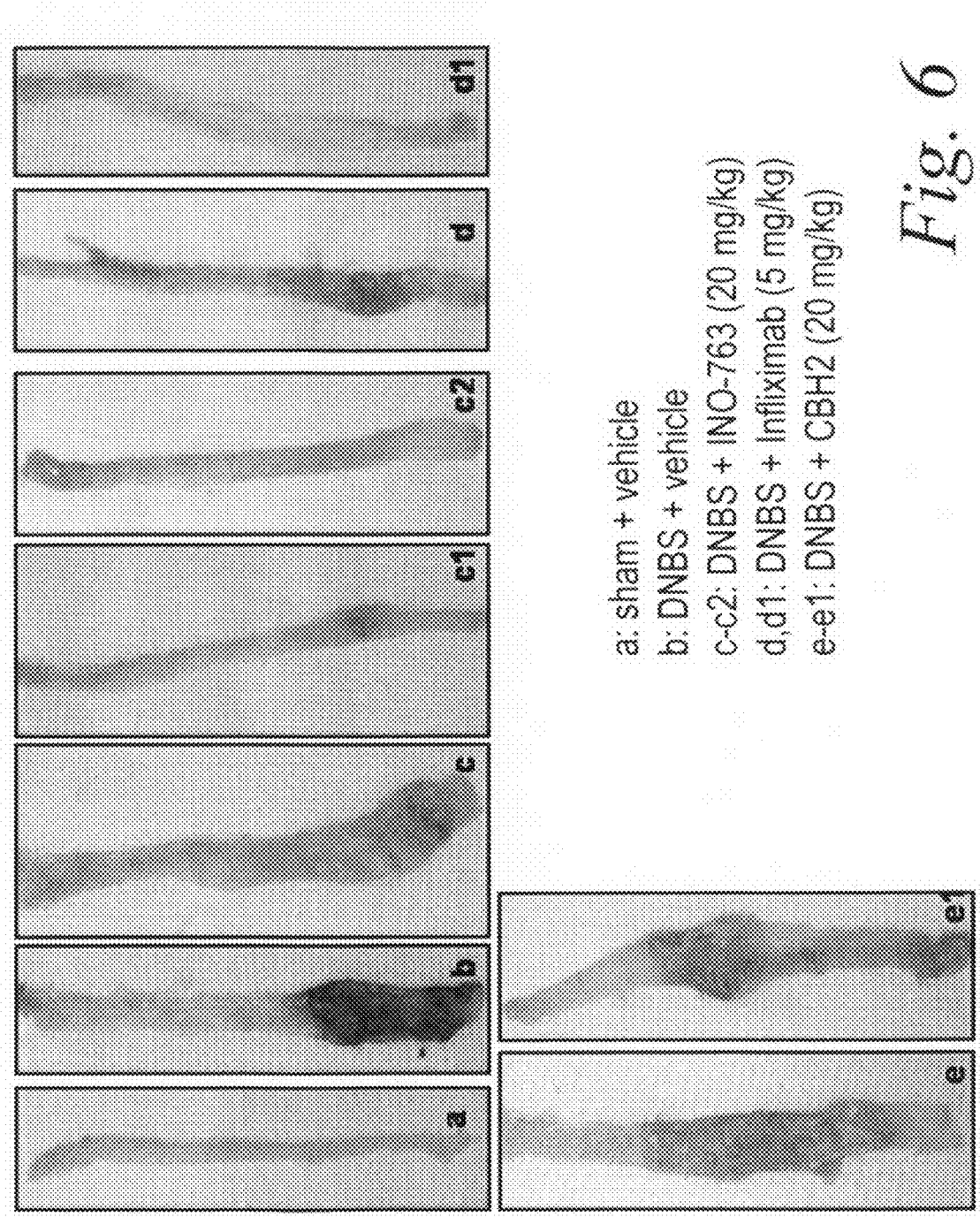
FIG. 6 depicts the macroscopic histological alterations of the colons of mice treated with either a sham-vehicle (FIG. 6a), a control-vehicle (FIG. 6b), DNBS and 20 mg/kg of mAb 763 (FIGS. 6c, 6c1 and 6c2), DNBS and 5 mg/kg of a positive control mAb, Infliximab (FIGS. 6d and 6d1), or DNBS and 20 mg/kg of an isotype human control mAb, CBH2 (FIGS. 6e and 6e1), as well as the macroscopic damage score for each of these experimental groups (FIG. 6f).
Figure 6F:
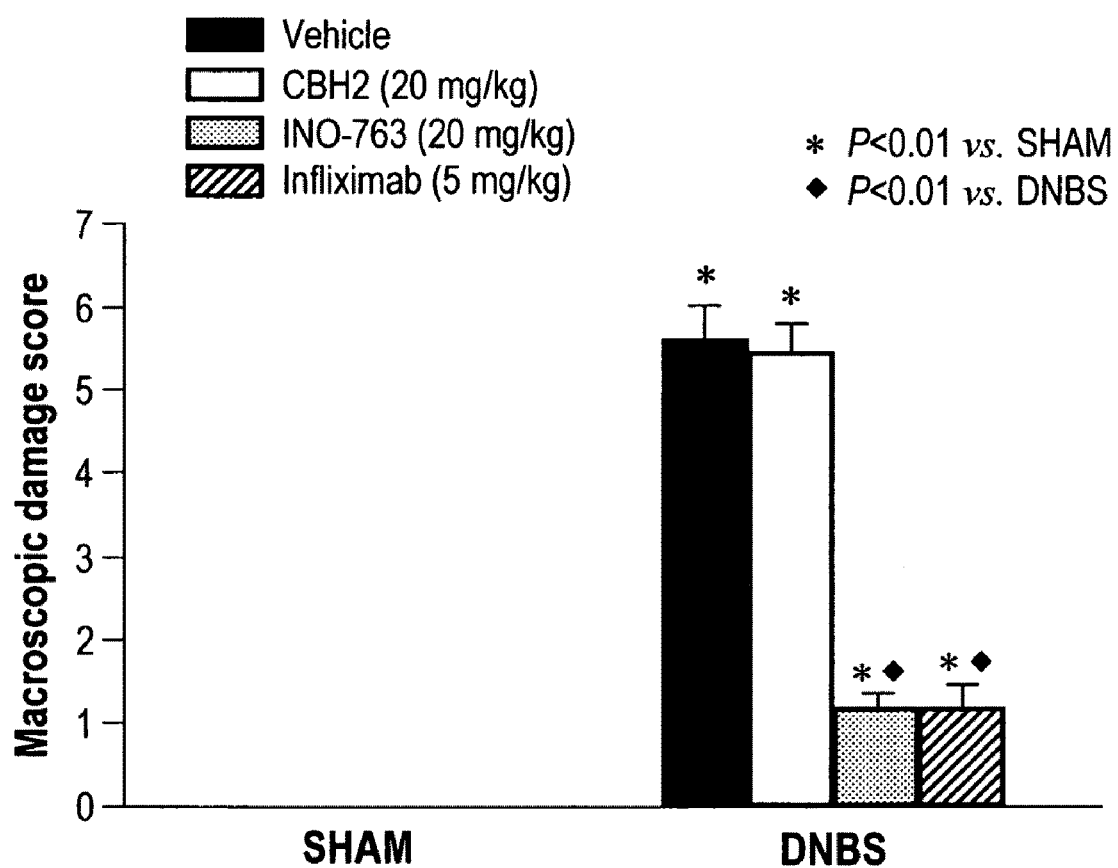
Figure 7:
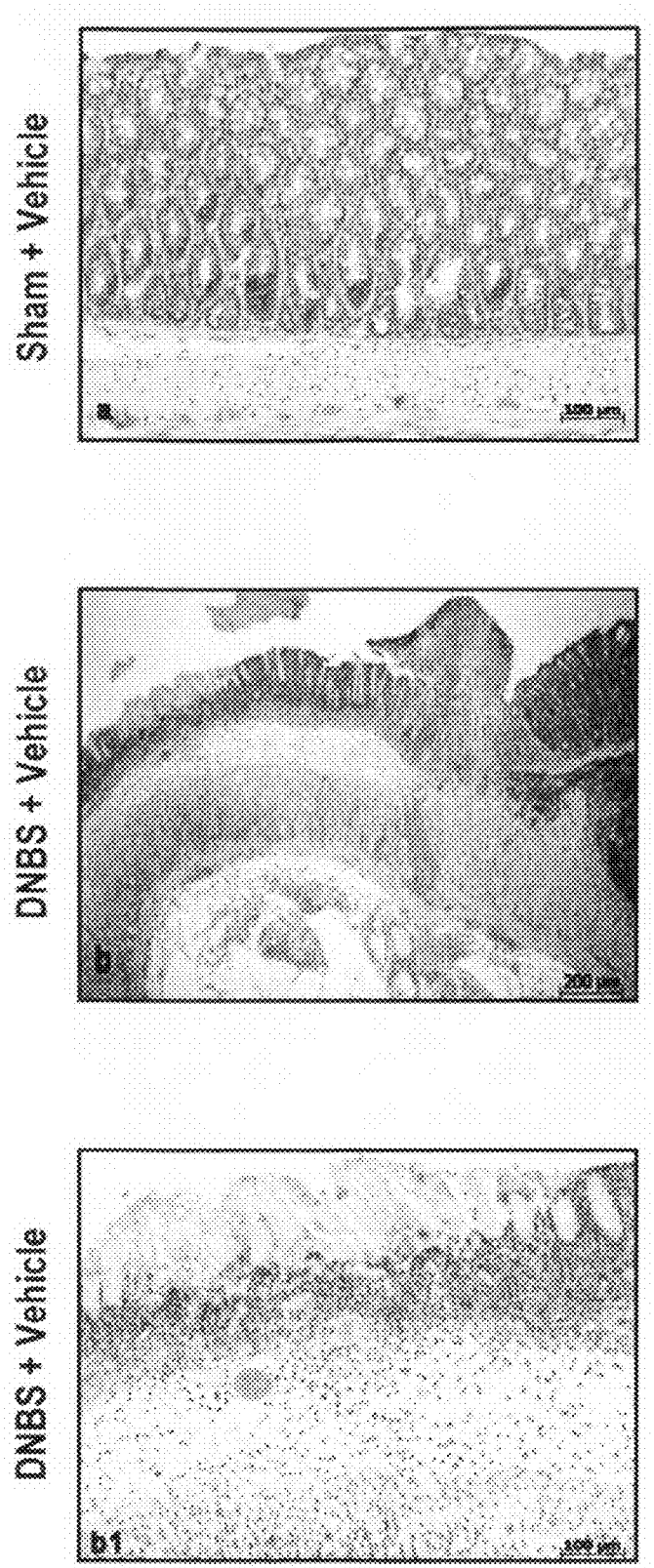
FIG. 7 depicts the histopathological features of the colons of mice treated with either a sham-vehicle (FIG. 7a), a control-vehicle (FIGS. 7b and 7b1), DNBS and 20 mg/kg of mAb 763 (FIGS. 7c and 7c1), DNBS and 5 mg/kg of a positive control mAb, Infliximab (FIGS. 7d, 7d1, and 7d2), or DNBS and 20 mg/kg of an isotype human control mAb, CBH2 (FIGS. 7e and 7e1), as well as the histological score for each of these experimental groups (FIG. 7f).
Figure 7:
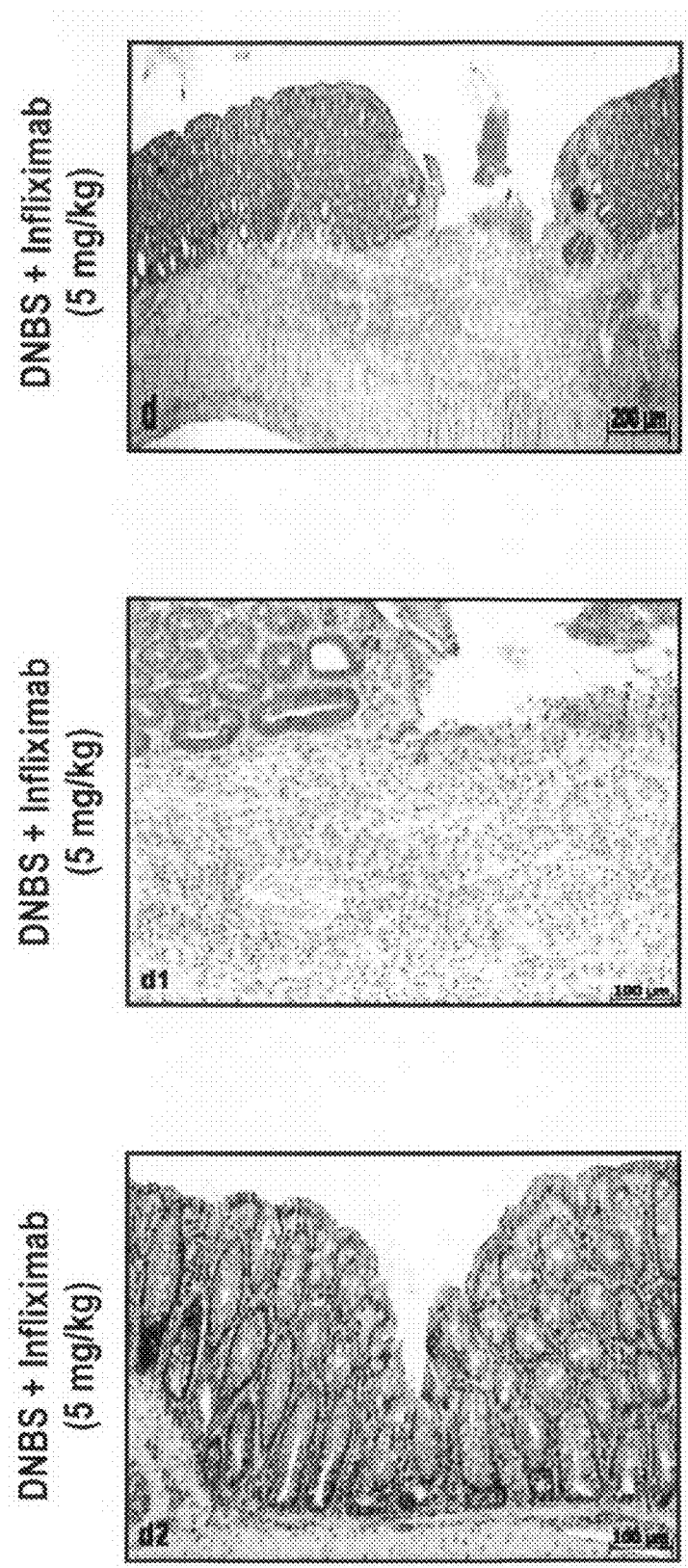
Figure 7F:
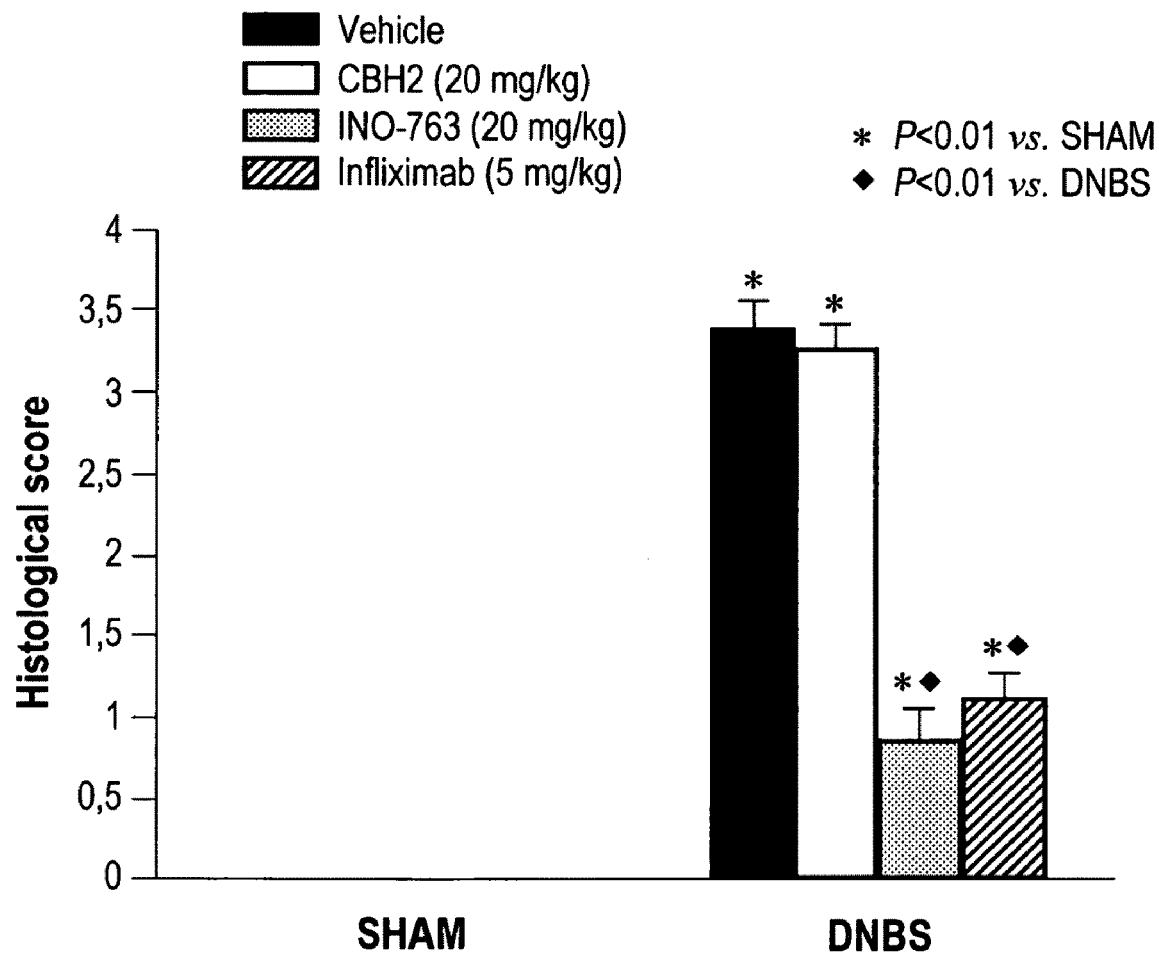
Figure 8:
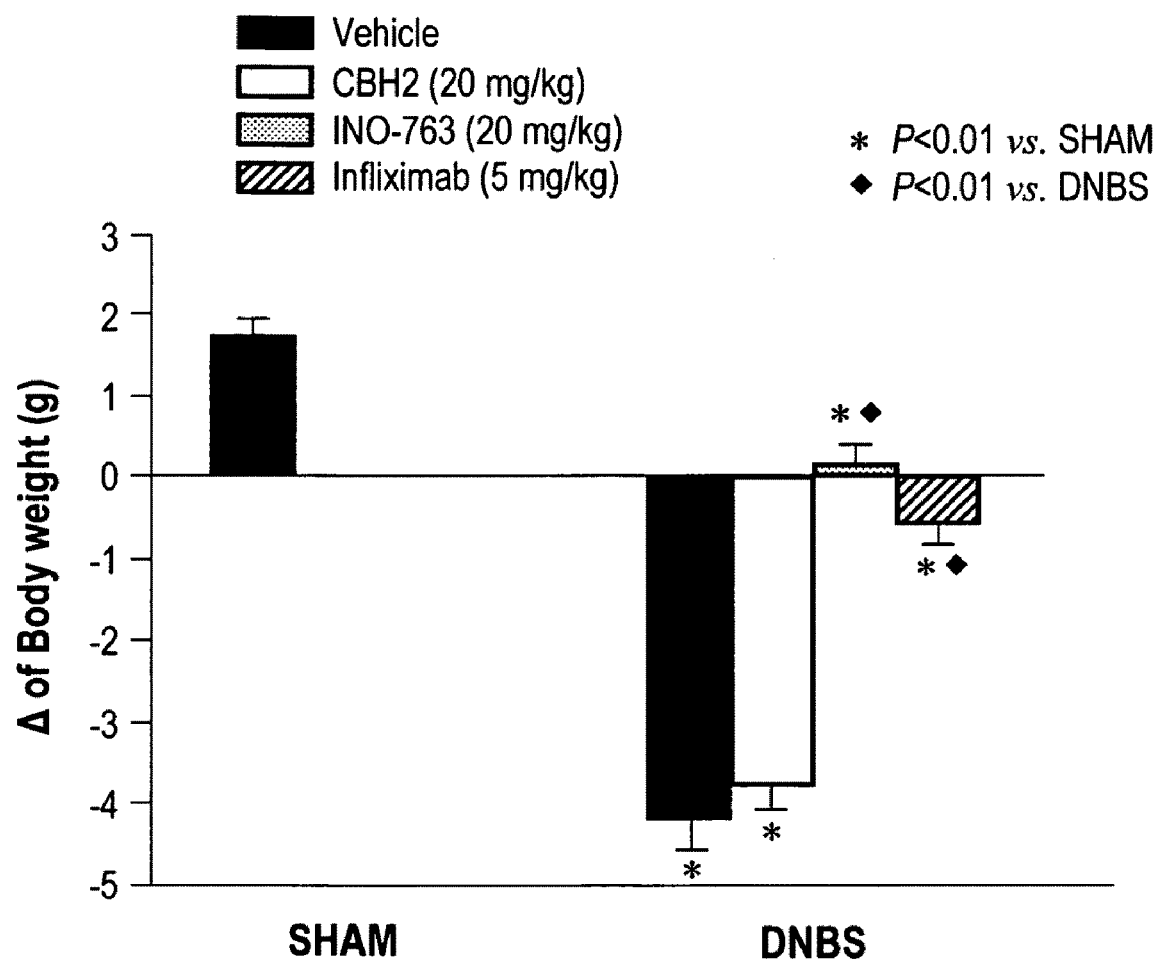
FIG. 8 is a graph illustrating the change in body weight in grams of mice treated with either a sham-vehicle, a control-vehicle, DNBS and 20 mg/kg of mAb 763, DNBS and 5 mg/kg of a positive control mAb, Infliximab, or DNBS and 20 mg/kg of an isotype human control mAb, CBH2.
Figure 9:
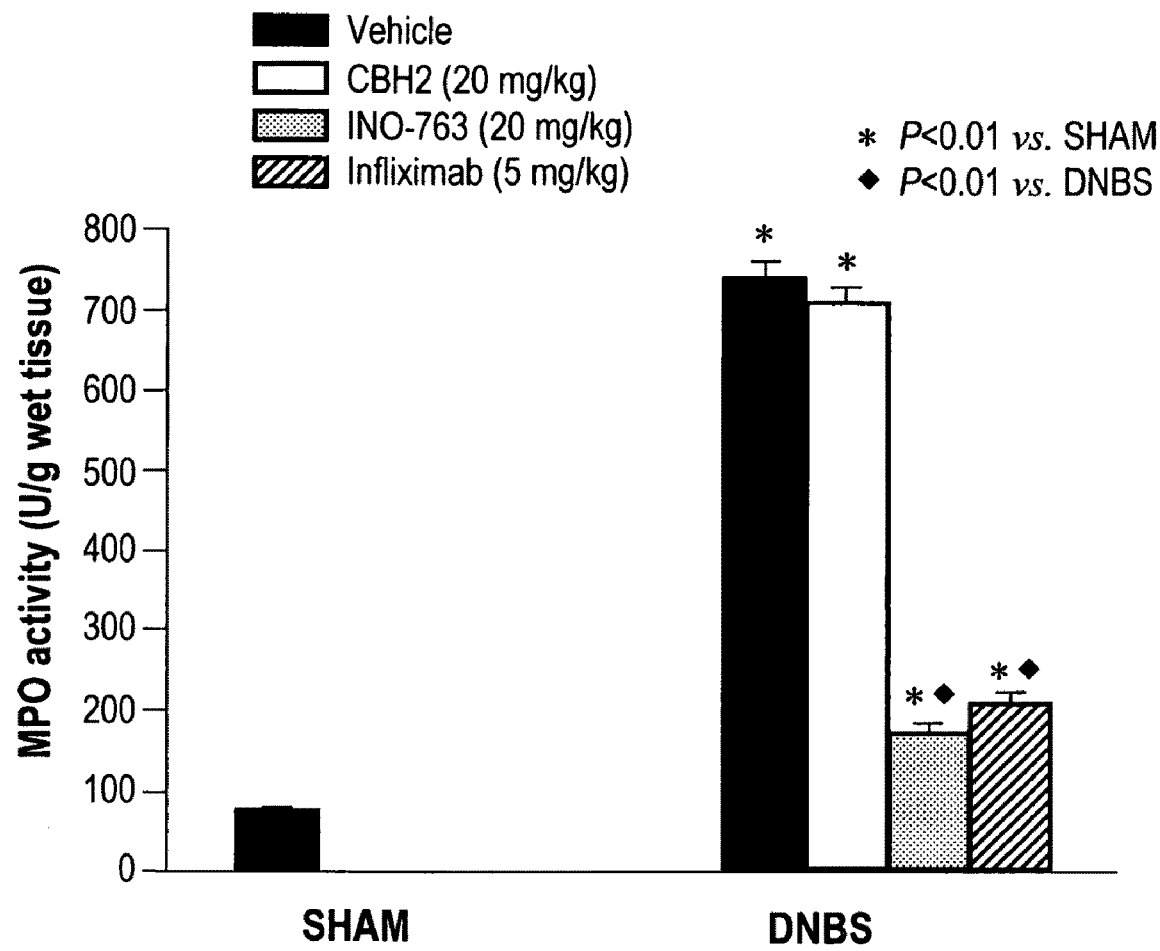
FIG. 9 is a graph illustrating myeloperoxidase (MPO) activity in mice treated with either a sham-vehicle, a control-vehicle, DNBS and 20 mg/kg of mAb 763, DNBS and 5 mg/kg of a positive control mAb, Infliximab, or DNBS and 20 mg/kg of an isotype human control mAb, CBH2.

No histological alteration was observed in the colon tissue from sham-treated mice (see FIG. 6a; see macroscopic score 6f; see FIG. 7a see histological score 7f). Four days after intra-colonic administration of DNBS, the colon appeared flaccid and filled with liquid stool. The macroscopic inspection of cecum, colon and rectum showed presence of mucosal congestion, erosion and hemorrhagic ulcerations (See FIG. 6b; see macroscopic score 6f). The histopathological features included a transmural necrosis and edema and a diffuse leukocyte cellular infiltrate in the submucosa of colon section from DNBS-treated mice (see FIG. 7b; see particle 7b1 and see histological score 7f). The treatment with mAb 763 (20 mg/kg) significantly reduced the extent and severity of the macroscopic (see FIGS. 6c, 6c1, and 6c2; see macroscopic score 6f) and histological signs of colon injury (see FIGS. 7c, 7c1, see histological score 7f). Similarly, the treatment with Infliximab (see FIGS. 6d and 6d1; see macroscopic score 6f and FIGS. 7d-72, see histological score 7f) significantly reduced the macroscopic and histological signs of colon injury. On the contrary the treatment with CBH2 (20 mg/kg) did not reduced the extent and severity of the macroscopic (see FIGS. 6e, 6e1; see macroscopic score 6f) and histological signs of colon injury (see FIGS. 7e, 7e1, see histological score 7f). Four days after colitis induced by DNBS treatment, all mice had diarrhea and a significant reduction in body weight (compared with the sham groups of mice) (FIG. 8). mAb 763 (20 mg/kg) treatment resulted in a significant reduction of loss of body weight induced by DNBS-administration in mice (FIG. 8). Similarly, but with less effectiveness, the treatment with Infliximab reduced the lost of body weight induced by DNBS-administration in mice (FIG. 8). On the contrary the treatment with CBH2 (20 mg/kg) did not reduced the loss of body weight induced by DNBS-administration in mice (FIG. 8). The colitis caused by DNBS was also characterized by an increase in myeloperoxidase activity, an indicator of the neutrophils accumulation in the colon (FIG. 9). This finding is consistent with the observation made with light microscopy that the colon of vehicle-treated DBNS-mice contained a large number of neutrophils. On the contrary, mAb 763 (20 mg/kg) treatment significantly reduced the degree of PMN infiltration (determined as increase in MPO activity) in inflamed colon (FIG. 9). Similarly, the treatment with Infliximab reduced the neutrophils infiltration in the colon tissues induced by DNBS-administration in mice (FIG. 9). On the contrary the treatment with CBH2 (20 mg/kg) did not reduced the neutrophils infiltration in the colon tissues induced by DNBS-administration in mice (FIG. 9).

B. Effects of Full-Dose Response Curve of mAb 741 (0.3-10 mg·kg) Versus DNBS-Induced Colitis 1. Experimental Groups: Animals were randomly divided into 7 groups (n=15 for each group):

| Group | DNBS | Treatment | Dosing |
|---|---|---|---|
| 1 | No | Sham-vehicle | 0.2 ml vehicle i.p. (saline solution) |
| 2 | Yes | Control-Vehicle | 0.2 ml vehicle i.p. (saline solution) |
| 3 | Yes | mAb 763 | 20 mg/kg i.p. |
| 4 | Yes | mAb 741 | 5 mg/kg i.p. |
| 5 | Yes | mAb 741 | 10 mg/kg i.p. |
| 6 | Yes | mAb 741 | 20 mg/kg i.p. |
| 7 | Yes | mAb 18.8 | 20 mg/kg i.p. |

2. Effects of mAb 763 and mAb 741 Treatment on the Degree of Colitis

Figure 10:
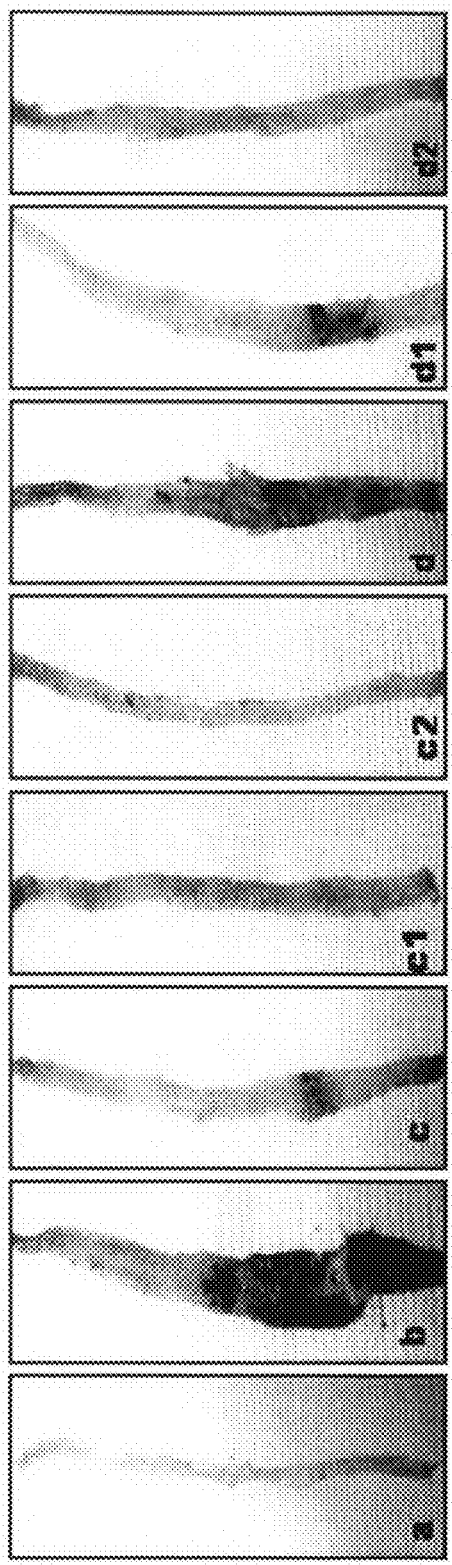
FIG. 10 depicts the macroscopic histological alterations of the colons of mice treated with either a sham-vehicle (FIG. 10a), a control-vehicle (FIG. 10b), DNBS and 20 mg/kg of mAb 741 (FIGS. 10c, 10c1 and 10c2), DNBS and 10 mg/kg of mAb 741 (FIGS. 10d, 10d1 and 10d2), DNBS and 5 mg/kg of mAb 741 (FIGS. 10e and 10e1), DNBS and 20 mg/kg of mAb 763 (FIGS. 10f and 10f1), and DNBS and 20 mg/kg of an isotype mouse control mAb, 18.8 (FIGS. 10g and 10g1), as well as the macroscopic damage score for each of these experimental groups (FIG. 10h).
Figure 10H:
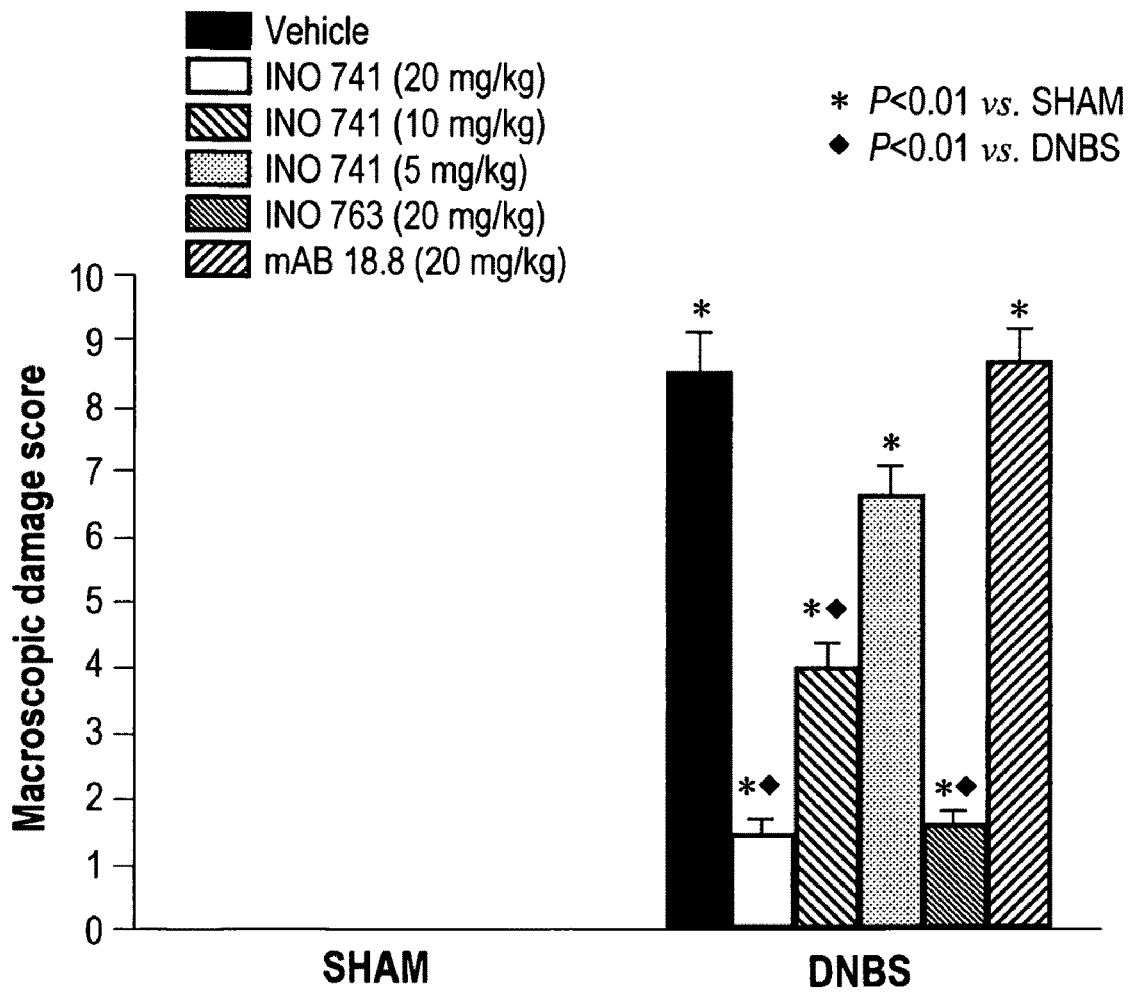
Figure 11:
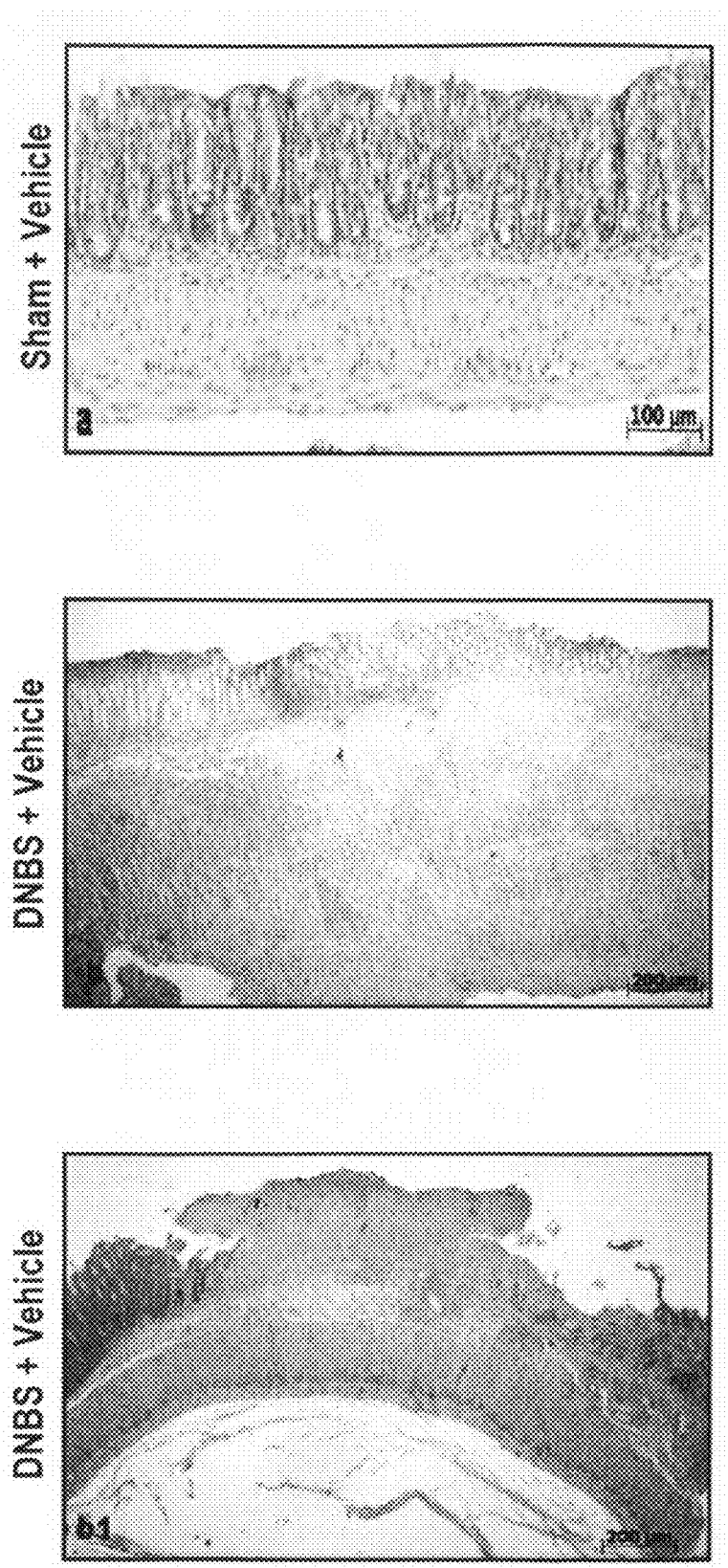
FIG. 11 depicts the histopathological features of the colons of mice treated with either a sham-vehicle (FIG. 11a), a control-vehicle (FIGS. 11b and 11b1), DNBS and 20 mg/kg of mAb 741 (FIGS. 11c and 11c1), DNBS and 10 mg/kg of mAb 741 (FIGS. 11d and 11d1), DNBS and 5 mg/kg of mAb 741 (FIGS. 11e and 11e1), DNBS and 20 mg/kg of mAb 763 (FIG. 11f), DNBS and 20 mg/kg of an isotype mouse control mAb, 18.8 (FIG. 11g), as well as the histological score for each of these experimental groups (FIG. 11h).
Figure 11:
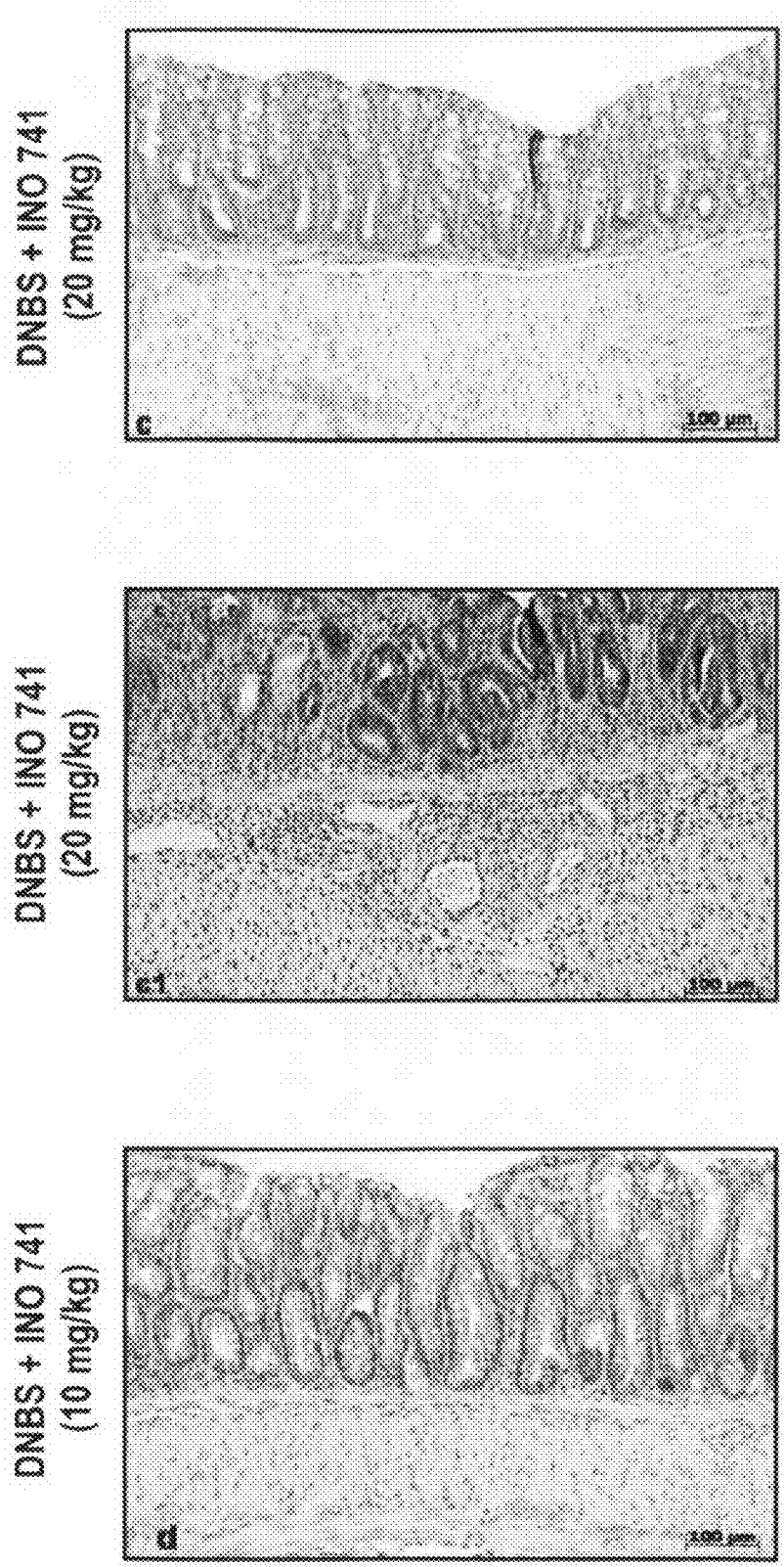
Figure 11:
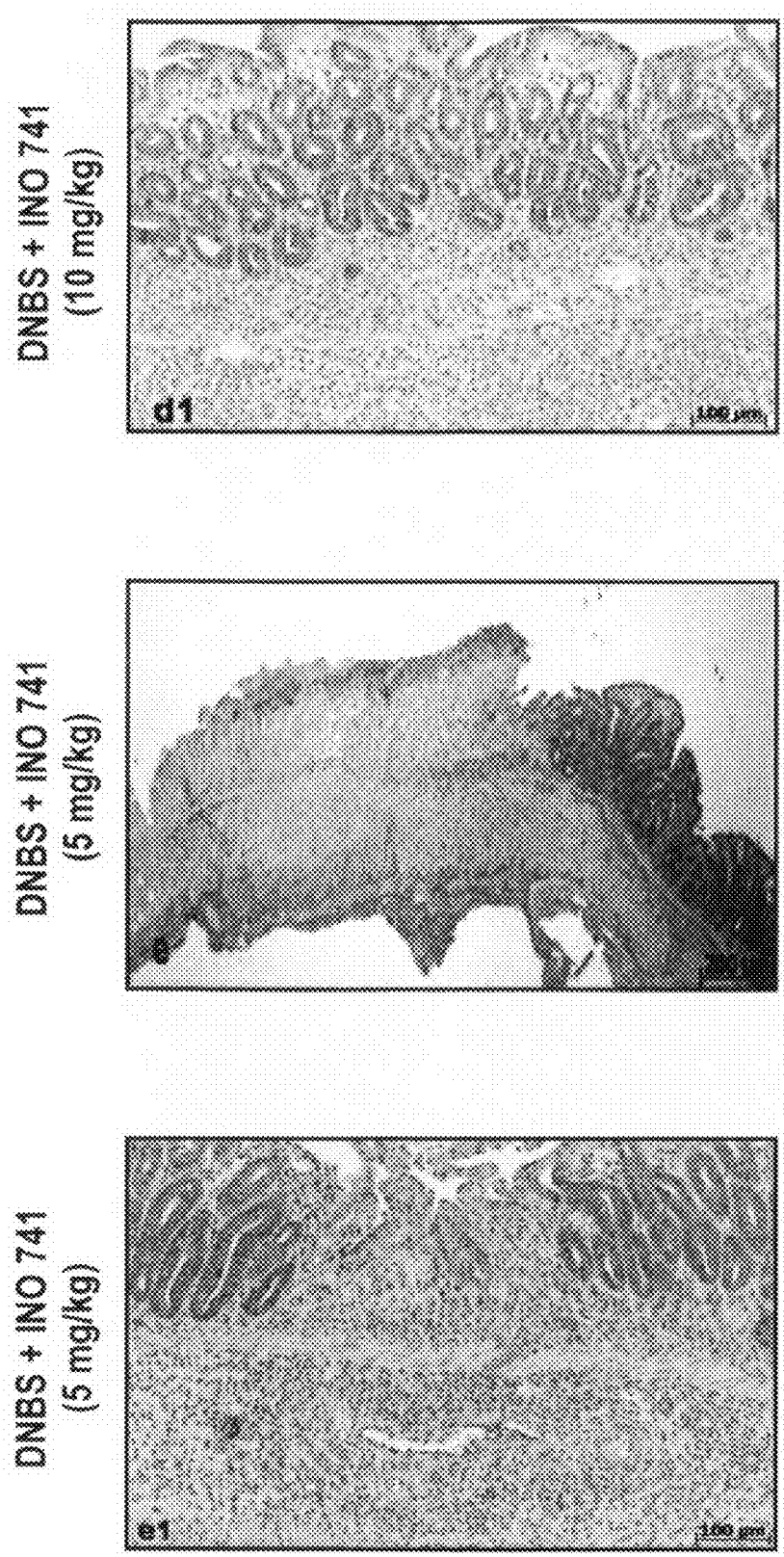
Figure 11H:
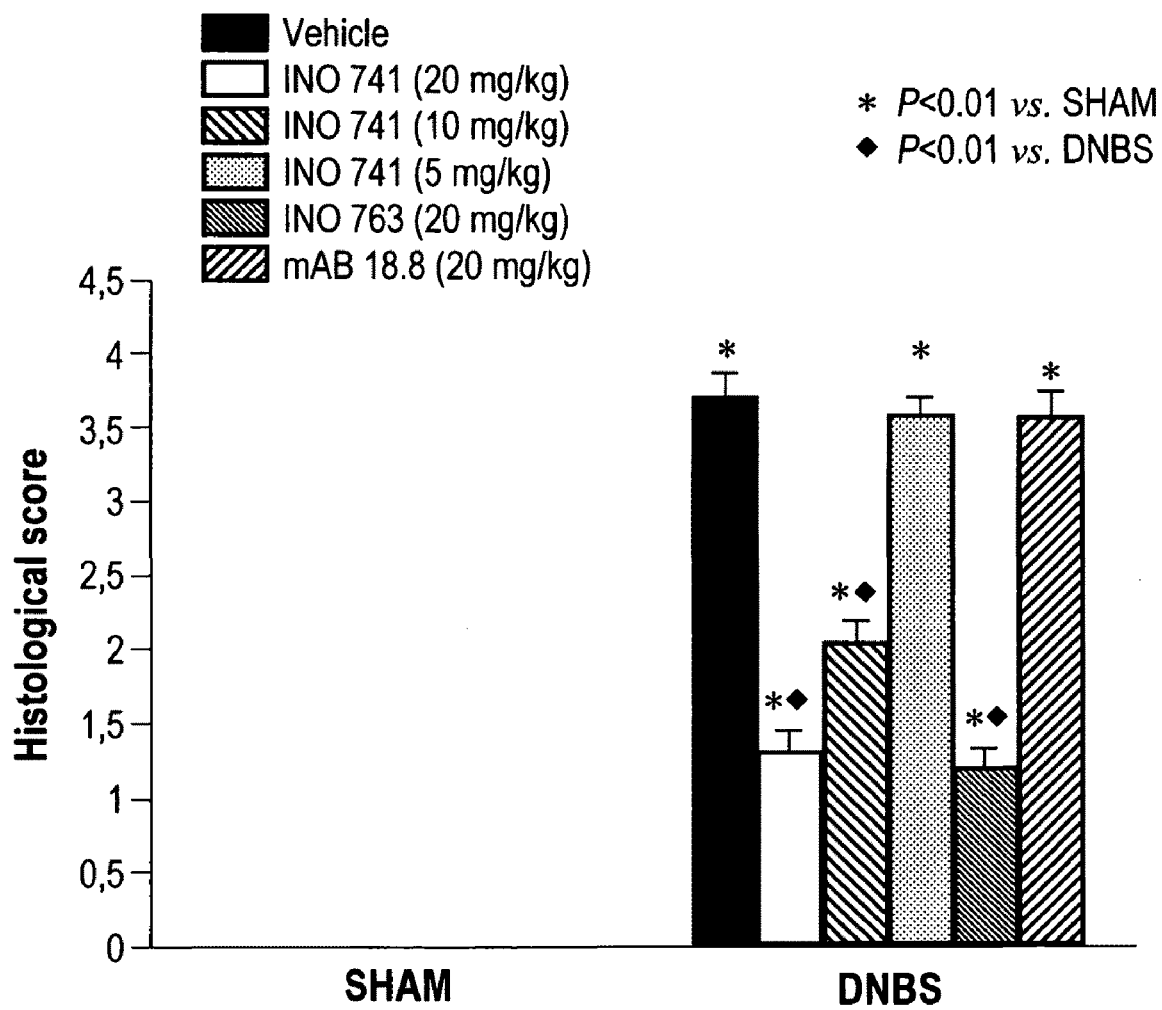
Figure 12:
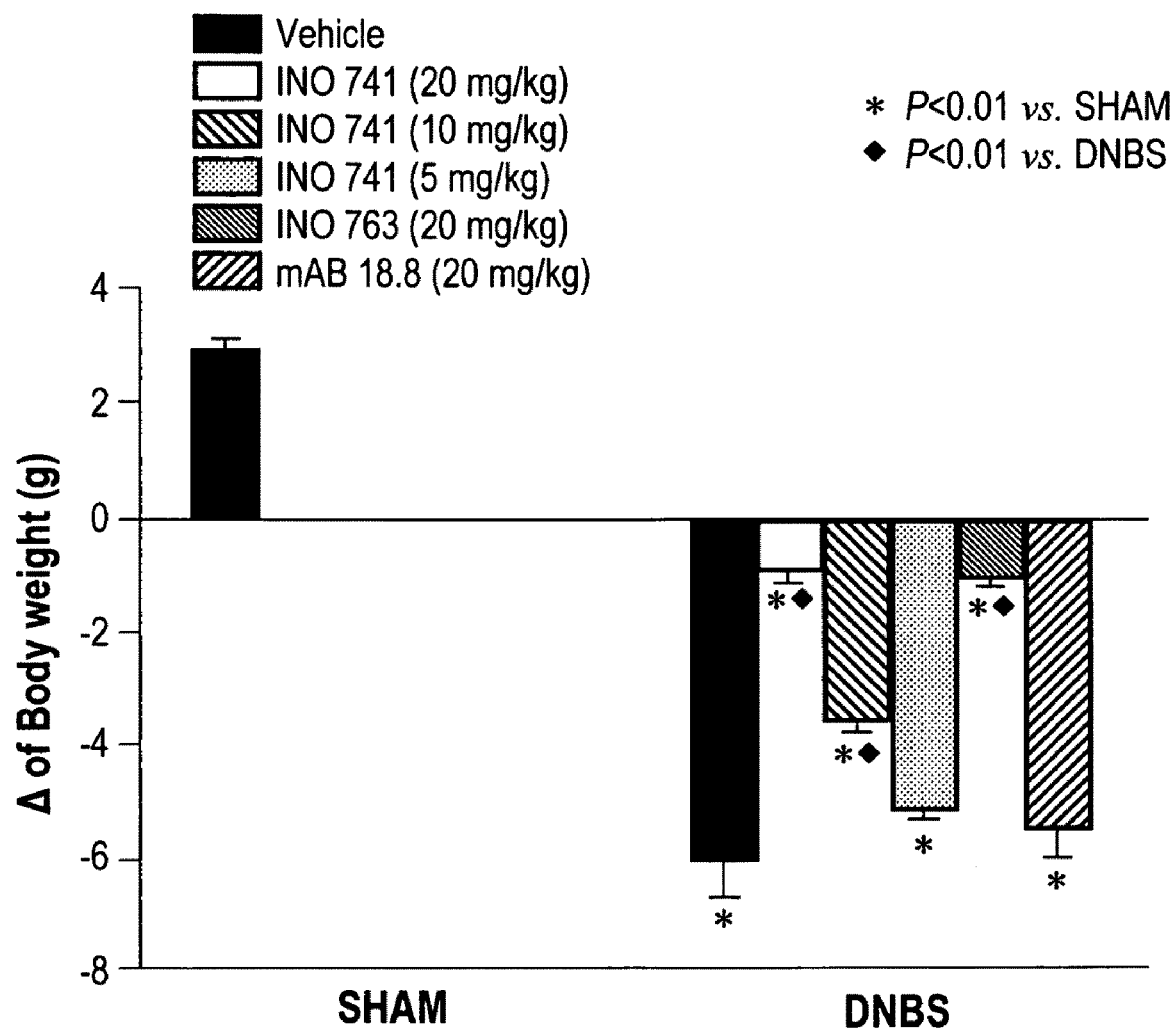
FIG. 12 is a graph illustrating the change in body weight in grams of mice treated with either a sham-vehicle, a control-vehicle, DNBS and 20 mg/kg of mAb 741, DNBS and 10 mg/kg of mAb 741, DNBS and 5 mg/kg of mAb 741, DNBS and 20 mg/kg of mAb 763, and DNBS and 20 mg/kg of an isotype mouse control mAb, 18.8.
Figure 13:
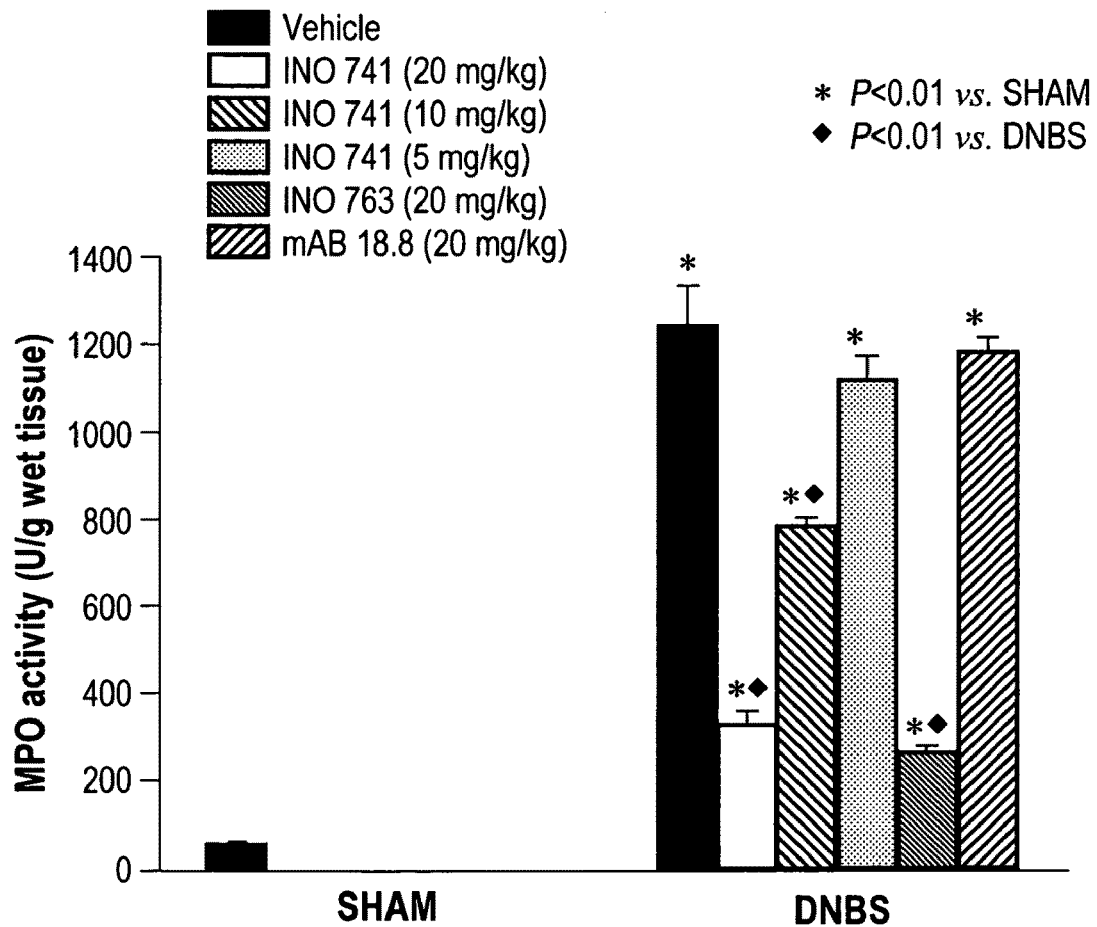
FIG. 13 is a graph illustrating myeloperoxidase (MPO) activity in mice treated with either a sham-vehicle, a control-vehicle, DNBS and 20 mg/kg of mAb 741, DNBS and 10 mg/kg of mAb 741, DNBS and 5 mg/kg of mAb 741, DNBS and 20 mg/kg of mAb 763, and DNBS and 20 mg/kg of an isotype mouse control mAb, 18.8.

No histological alteration was observed in the colon tissue from sham-treated mice (see FIG. 10a; see macroscopic score 10h, FIG. 11a see histological score 11h). Four days after intra-colonic administration of DNBS, the colon appeared flaccid and filled with liquid stool. The macroscopic inspection of cecum, colon and rectum showed presence of mucosal congestion, erosion and hemorrhagic ulcerations (see FIG. 10b; see macroscopic score 10h). The histopathological features included a transmural necrosis and edema and a diffuse leukocyte cellular infiltrate in the submucosa of colon section from DNBS-treated mice (see FIGS. 11b and 11b1; see histological score 11h). The treatment with mAb 763 (20 mg/kg) significantly reduced the extent and severity of the macroscopic (see FIGS. 10f and 10f1; see macroscopic score 9h) and histological signs of colon injury (see FIG. 11f; see histological score 11h). Similarly, the treatment with mAb 741 (20 and 10 mg/kg) reduced in a dose dependent manner the macroscopic and histological signs of colon injury (see FIGS. 10c, 10c1, 10c2, 10d, 10d1, and 10d2; see macroscopic score 10h; FIGS. 11c, 11c1, 11d, and 11d1; see histological score 11h respectively. On the contrary the treatment with mAb 741 at 5 mg/kg did not reduced the extent and severity of the macroscopic 20 (see FIGS. 10e, 10e1; see macroscopic score 10h) and histological signs of colon injury (FIGS. 11e and 11e1 respectively, see histological score 11h). Four days after colitis induced by DNBS treatment, all mice had diarrhea and a significant reduction in body weight (compared with the sham groups of mice) (FIG. 12).

mAb 763 (20 mg/kg) treatment resulted in a significant reduction of lost of body weight induced by DNBS-administration in mice (FIG. 12). Similarly, the treatment with mAb 741 (20 and 10 mg/kg) reduced in a dose dependent manner the lost of body weight induced by DNBS-administration in mice (FIG. 12). On the contrary the treatment with mAb 741 at 5 mg/kg did not reduced the lost of body weight induced by DNBS-administration in mice (FIG. 12). The colitis caused by DNBS was also characterized by an increase in myeloperoxidase activity, an indicator of the neutrophils accumulation in the colon (FIG. 13). This finding is consistent with the observation made with light microscopy that the colon of vehicle-treated DBNS-mice contained a large number of neutrophils. mAb 763 (20 mg/kg) treatment significantly reduced the degree of PMN infiltration (determined as increase in MPO activity) in inflamed colon (FIG. 13). Similarly, the treatment with mAb 741 (20 and 10 mg/kg) reduced in a dose dependent manner the neutrophils infiltration in the colon tissues induced by DNBS-administration in mice (FIG. 13). On the contrary the treatment with mAb 741 at 5 mg/kg did not reduced the neutrophils infiltration in the colon tissues induced by DNBS-administration in mice (FIG. 13).

Treatment with mAB 18.8 (20 mg/kg) did not reduced the macroscopic (FIGS. 10g and 10g1; see macroscopic score 10h) and histological signs of colon injury (see FIG. 11g, see histological score 11h), the degree of PMN infiltration (FIG. 12) and the lost of body weight induced by DNBS-administration in mice (FIG. 13).

3. Effects of mAb 763 and mAb 741 Treatment on the Mortality

Figure 14:
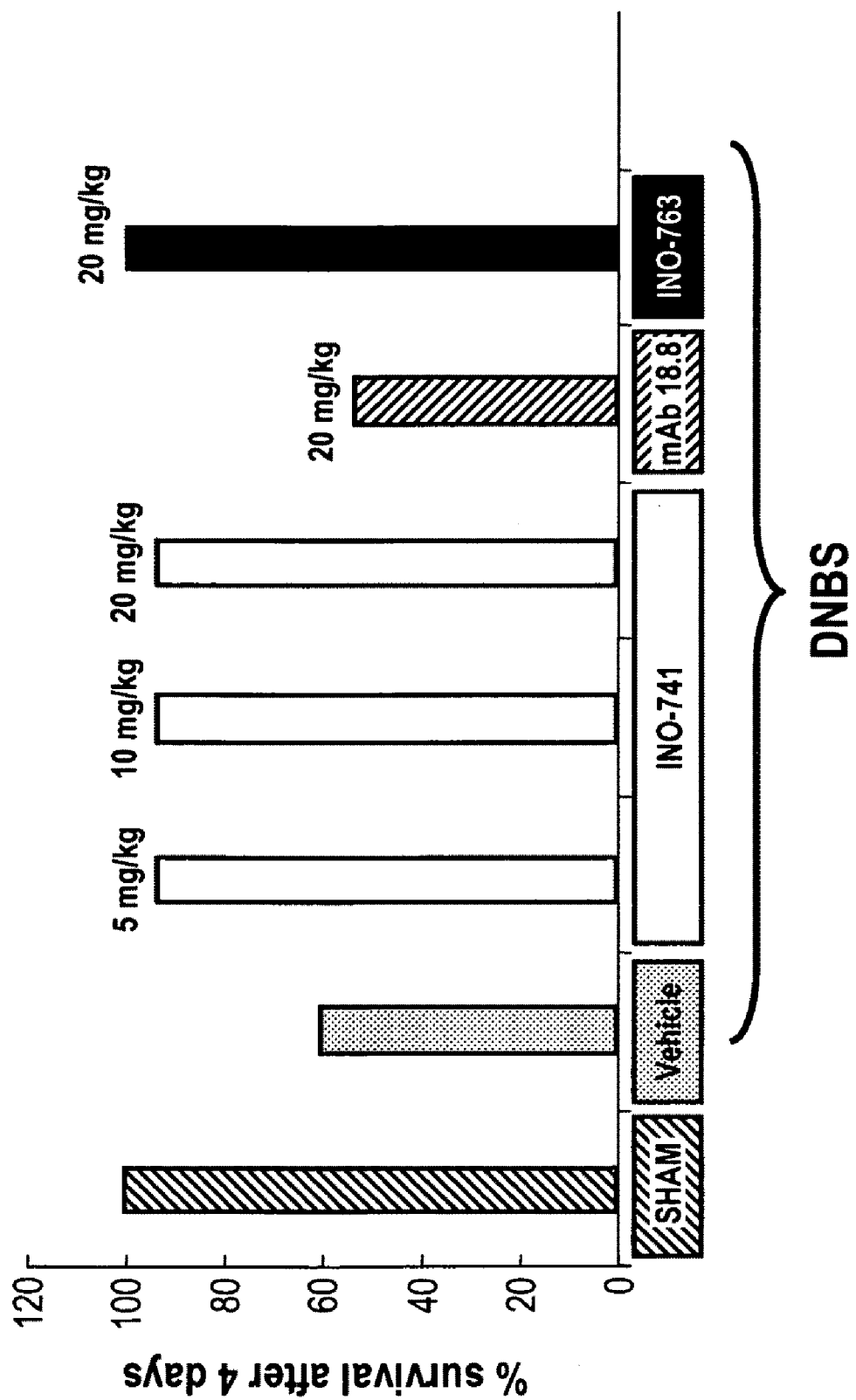
FIG. 14 is a graph showing the effects of mAb 741 and mAb 763 on mortality in an in vivo murine model of colitis, wherein the mice were sham treated or treated with either DNBS and a control-vehicle, DNBS and 5 mg/kg of mAb 741, DNBS and 10 mg/kg of mAb 741, DNBS and 20 mg/kg of mAb 741, DNBS and 20 mg/kg of mAb 18.8, or DNBS and 20 mg/kg of mAb 763.

DNBS-mice, which had received vehicle, developed severe hemorrhagic diarrhea, and 46% of these animals died within 4 days (FIG. 14). In contrast, no DNBS-treated mice which had been treated with mAb 763 (20 mg/kg) died. Similarly, only 6.6% of the DNBS-treated mice, which had been treated with mAb 741 (20, 10 and 5 mg/kg) had hemorrhagic diarrhoea and died. Please note that DNBS-mice, which had received monoclonal antibody 18.8 (20 mg/kg) developed severe hemorrhagic diarrhoea, and 40% of these animals died within 4 days.

C. Effects of Full-Dose Response Curve of mAb 763 (5-20 mg/kg) Versus DNBS-Induced Colitis 1. Experimental Groups: Animals were randomly divided into 7 groups (n=15 for each group):

| Group | DNBS | Treatment | Dosing |
|---|---|---|---|
| 1 | No | Sham-vehicle | 0.2 ml vehicle i.p. (saline solution) |
| 2 | Yes | Control-Vehicle | 0.2 ml vehicle i.p. (saline solution) |
| 3 | Yes | mAb 763 | 10 mg/kg i.p. |
| 4 | Yes | mAb 763 | 3 mg/kg i.p. |
| 5 | Yes | mAb 763 | 1 mg/kg i.p. |
| 6 | Yes | mAb 763 | 0.3 mg/kg i.p. |
| 7 | Yes | mAb CBH2 | 10 mg/kg i.p. |

2. Effects of mAb 763 Treatment on the Degree of Colitis

Figure 15:
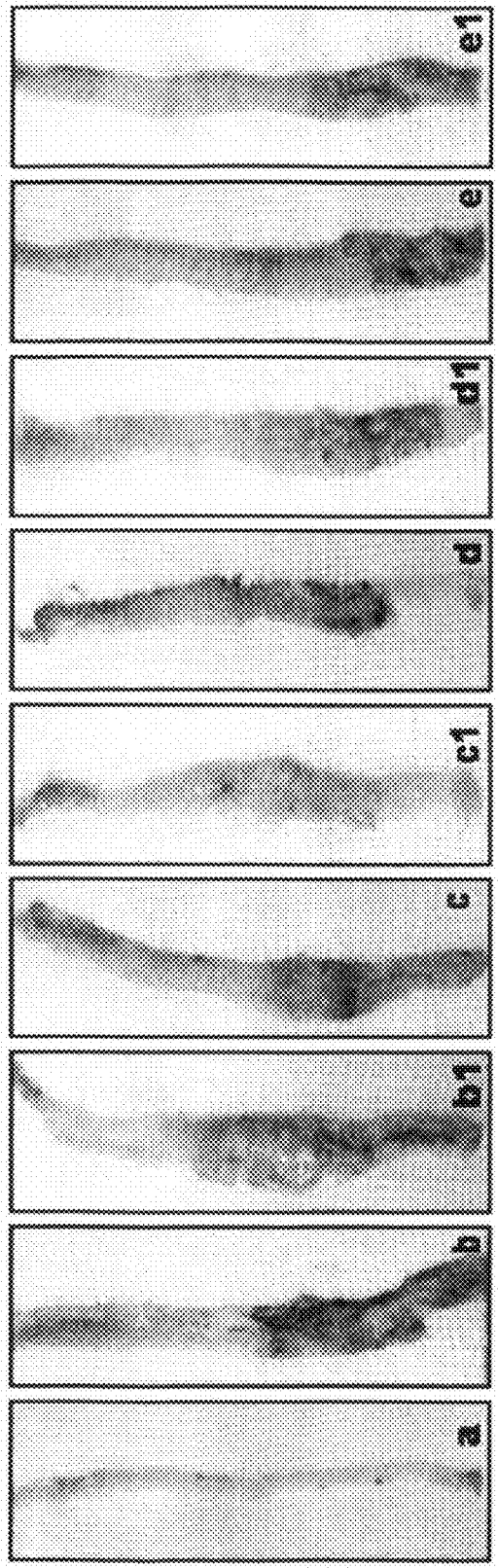
FIG. 15 depicts the macroscopic histological alterations of the colons of mice treated with either a sham-vehicle (FIG. 15a), a control-vehicle (FIG. 15b), DNBS and 10 mg/kg of mAb 763 (FIGS. 15c, 15c1 and 15c2), DNBS and 3 mg/kg of mAb 763 (FIGS. 15d and 15d1), DNBS and 1 mg/kg of mAb 763 (FIGS. 15e and 15e1), DNBS and 0.3 mg/kg of mAb 763 (FIGS. 15f and 15f1), and DNBS and 10 mg/kg of an isotype human control mAb, CBH2 (FIGS. 15g and 15g1), as well as the macroscopic damage score for each of these experimental groups (FIG. 15h).
Figure 15H:
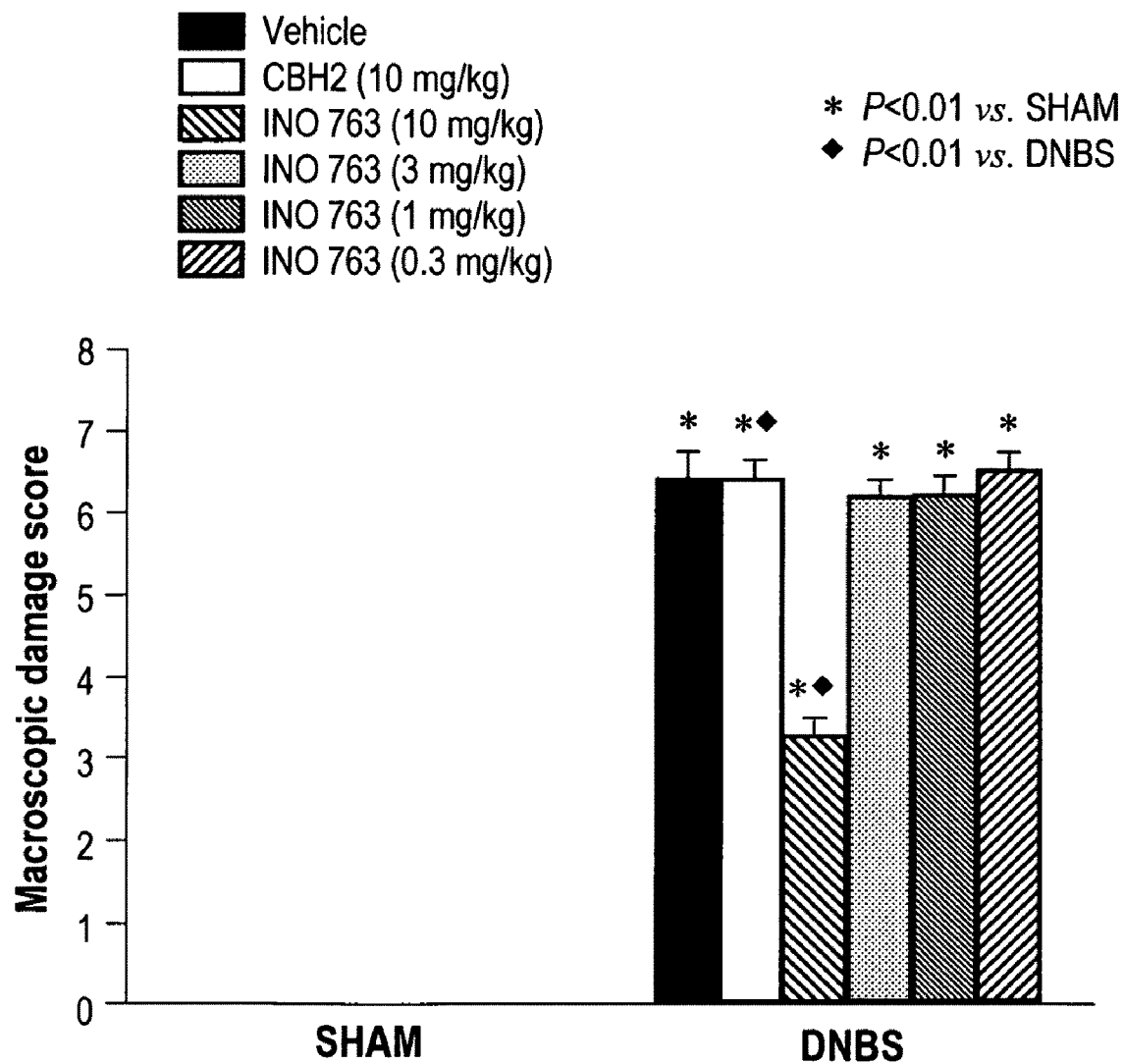
Figure 16:
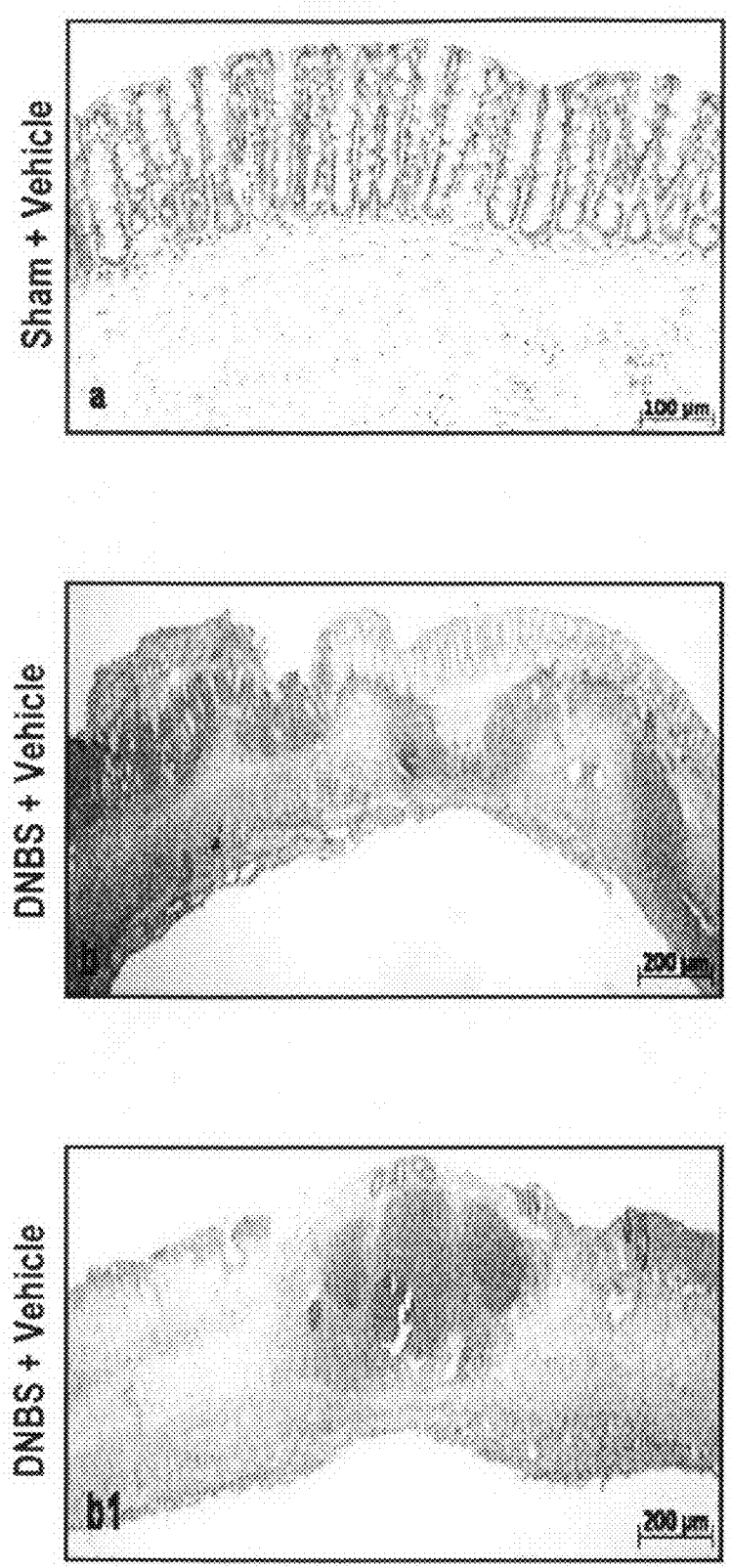
FIG. 16 depicts the histopathological features of the colons of mice treated with either a sham-vehicle (FIG. 16a), a control-vehicle (FIGS. 16b and 16b1), DNBS and 10 mg/kg of mAb 763 (FIGS. 16c, 16c1 and 16c2), DNBS and 3 mg/kg of mAb 763 (FIG. 16d), DNBS and 1 mg/kg of mAb 763 (FIG. 16e), DNBS and 0.3 mg/kg of mAb 763 (FIG. 16f), and DNBS and 10 mg/kg of an isotype human control mAb, CBH2 (FIG. 16g), as well as the histological score for each of these experimental groups (FIG. 16h).
Figure 16:
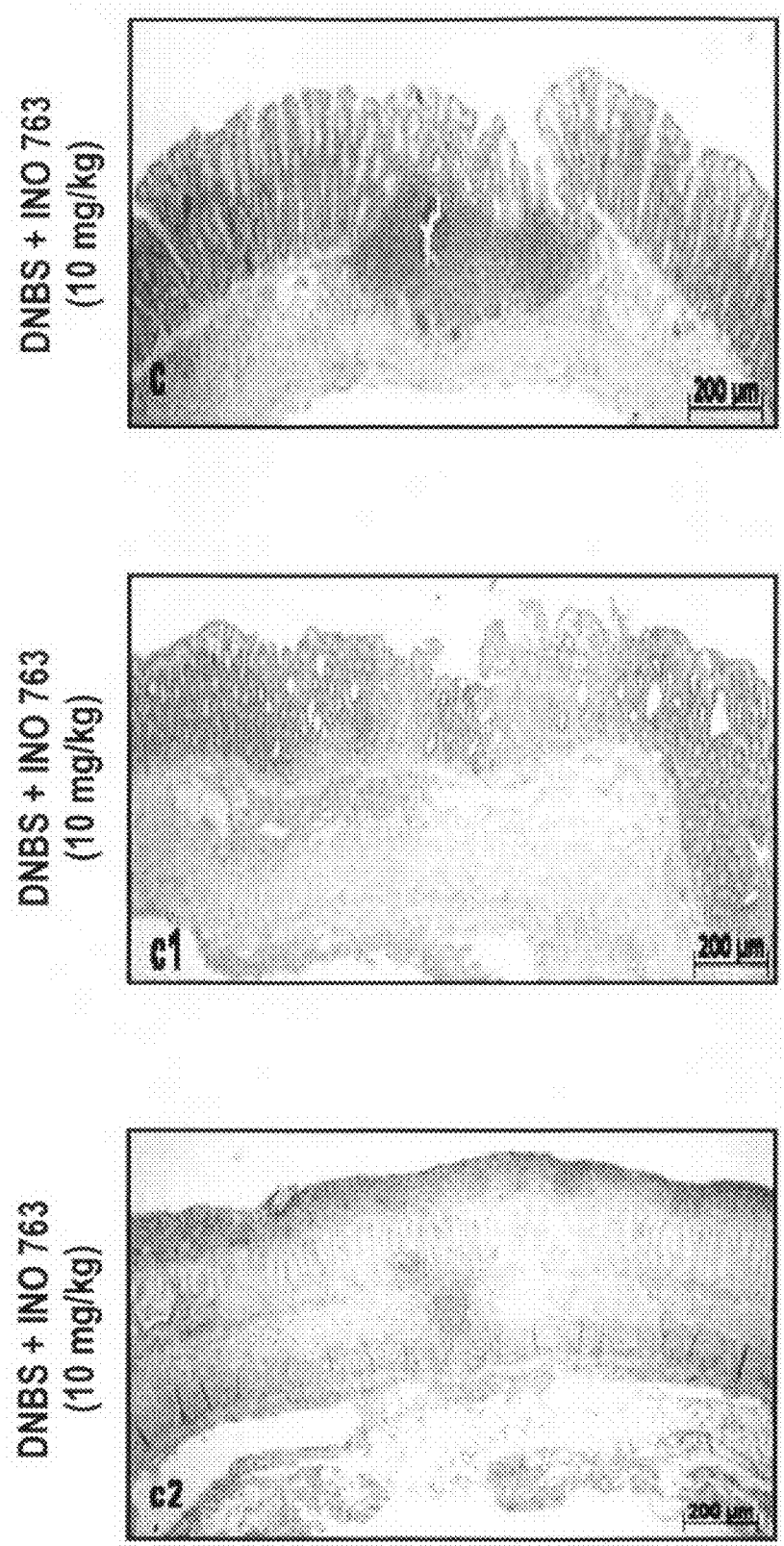
Figure 16:
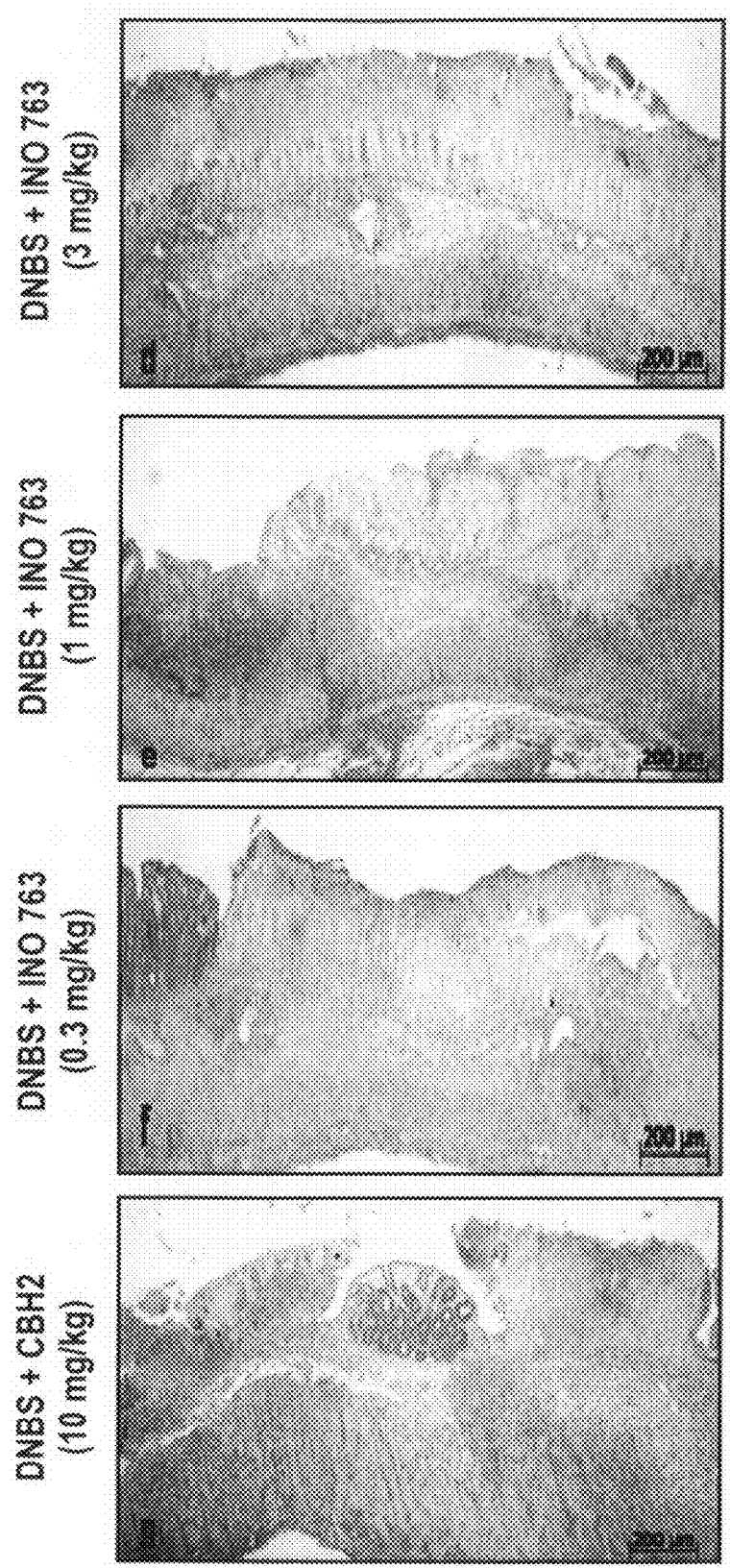
Figure 16H:
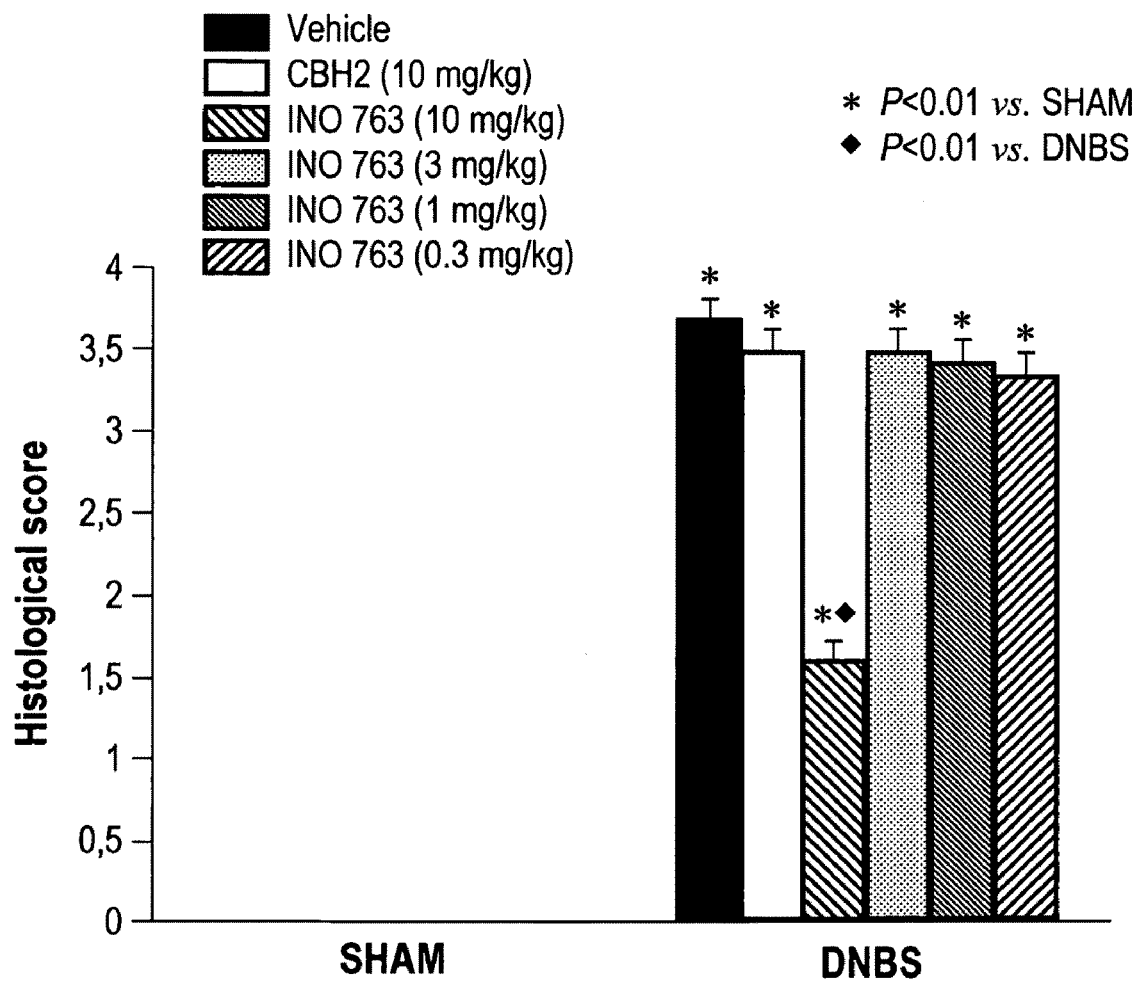
Figure 17:
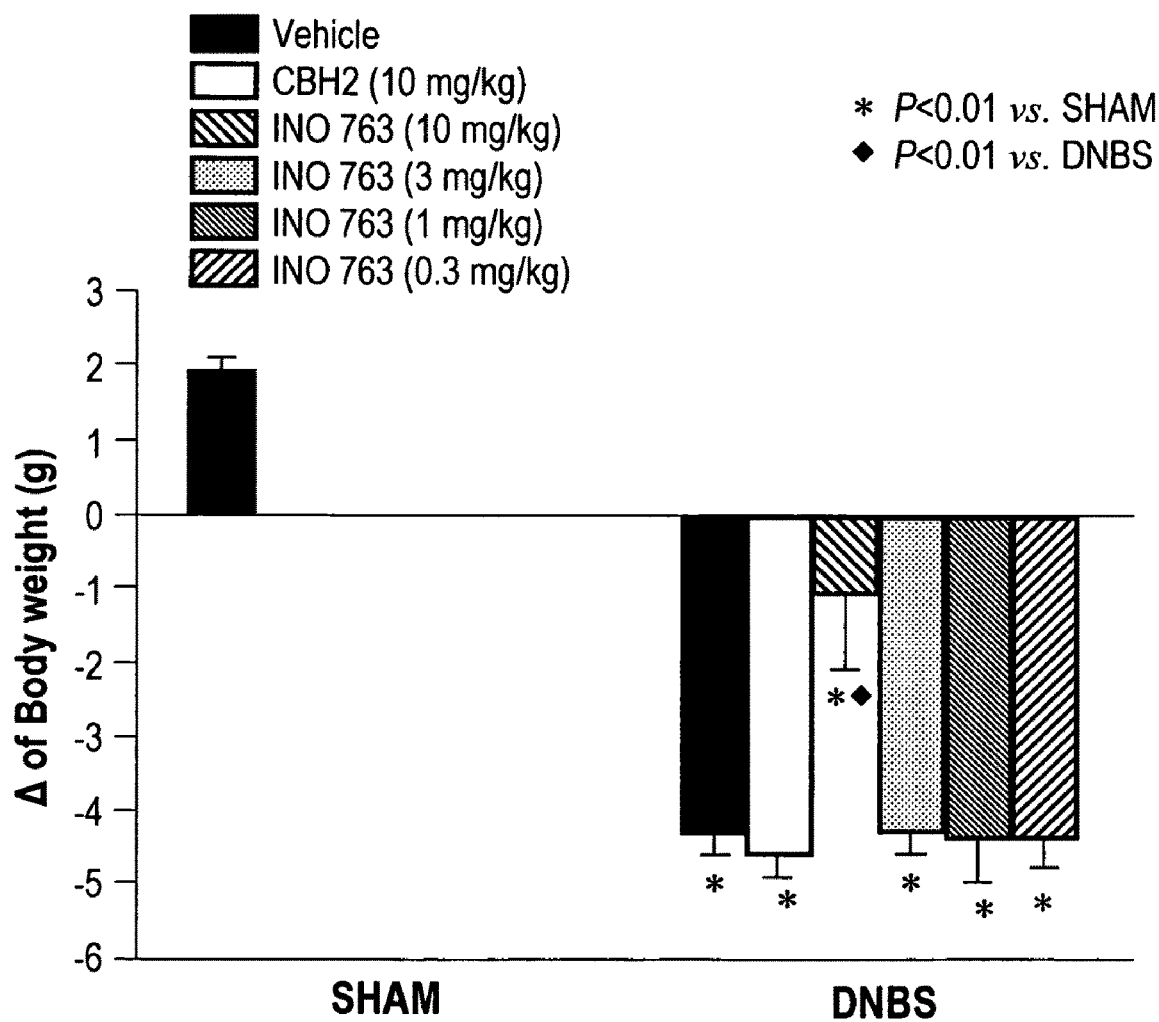
FIG. 17 is a graph illustrating the change in body weight in grams of mice treated with either a sham-vehicle, a control-vehicle, DNBS and 10 mg/kg of mAb 763, DNBS and 3 mg/kg of mAb 763, DNBS and 1 mg/kg of mAb 763, DNBS and 0.3 mg/kg of mAb 763, and DNBS and 10 mg/kg of an isotype human control mAb, CBH2.
Figure 18:
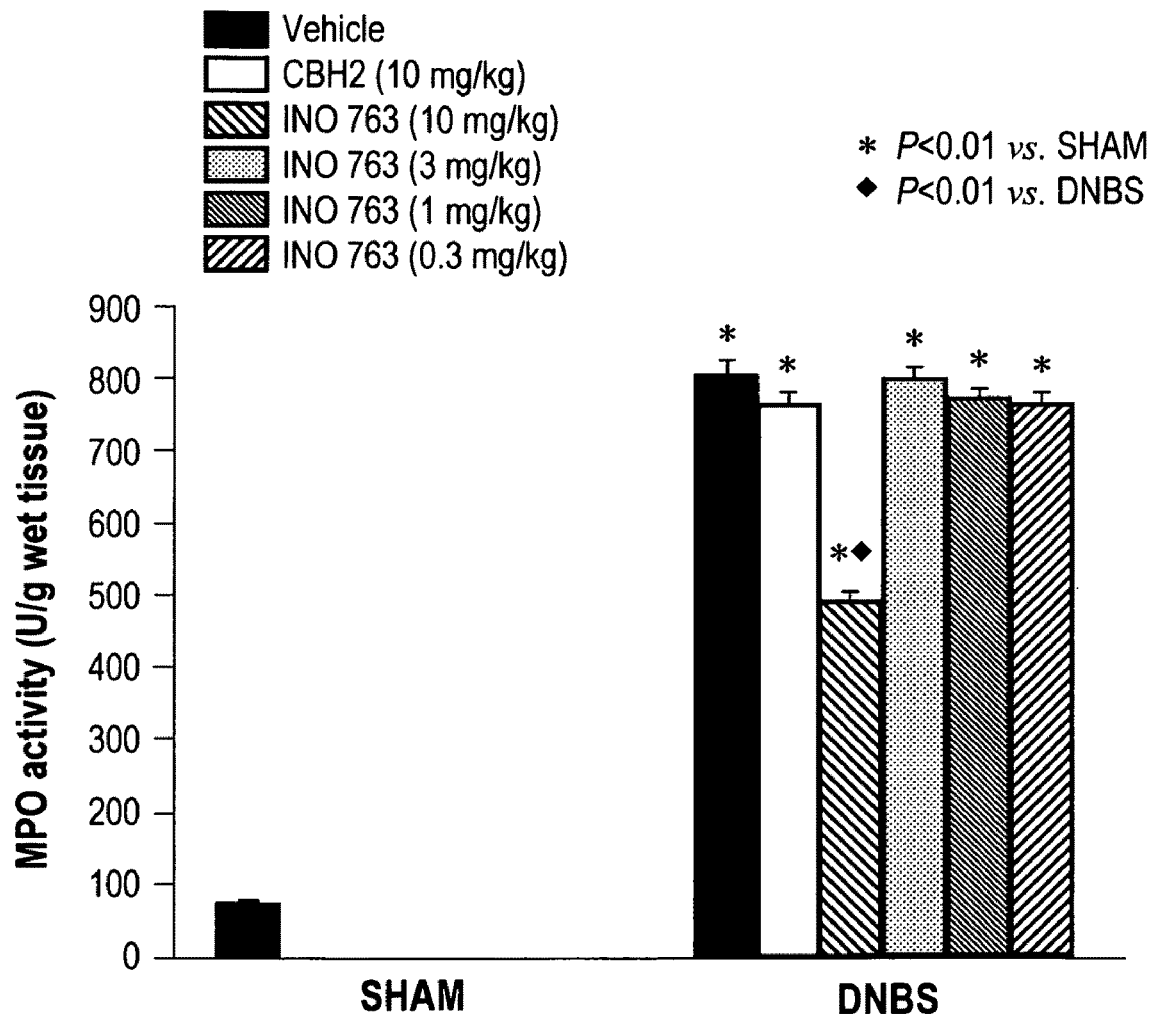
FIG. 18 is a graph illustrating myeloperoxidase (MPO) activity in mice treated with either a sham-vehicle, a control-vehicle, DNBS and 10 mg/kg of mAb 763, DNBS and 3 mg/kg of mAb 763, DNBS and 1 mg/kg of mAb 763, DNBS and 0.3 mg/kg of mAb 763, and DNBS and 10 mg/kg of an isotype human control mAb, CBH2.

No histological alteration was observed in the colon tissue from sham-treated—mice (see FIG. 15a; see macroscopic score 15h; FIG. 16a; see histological score 16h). Four days after intra-colonic administration of DNBS, the colon appeared flaccid and filled with liquid stool. The macroscopic inspection of cecum, colon and rectum showed presence of mucosal congestion, erosion and hemorrhagic ulcerations (FIGS. 15b and 15b1; see macroscopic score 15h). The histopathological features included a transmural necrosis and edema and a diffuse leukocyte cellular infiltrate in the submucosa of colon section from DNBS-treated mice (FIGS. 16b and 16b1; see histological score 16h). The treatment with mAb 763 (10 mg/kg) significantly reduced the extent and severity of the macroscopic (FIGS. 15c and 15c1; see macroscopic score 15h) and histological signs of colon injury (FIGS. 16c, 16c1, 16c2; see histological score 15h). On the contrary the treatment with mAb 763 at 3, 1, 0.3 mg/kg did not reduced the extent and severity of the macroscopic (FIGS. 15d, 15d1, 15e, 15e1, 15f, and 15f1, respectively; see macroscopic score 15h) and histological signs of colon injury (FIGS. 16d, 16e and 16f, respectively; see histological score 16h). Four days after colitis induced by DNBS treatment, all mice had diarrhea and a significant reduction in body weight (compared with the sham groups of rats) (FIG. 17). mAb 763 (10 mg/kg) treatment resulted in a significant reduction of lost of body weight induced by DNBS-administration in mice (FIG. 17). On the contrary the treatment with mAb 763 at 3, 1, 0.5 mg/kg did not reduced the lost of body weight induced by DNBS-administration in mice (FIG. 17). The colitis caused by DNBS was also characterized by an increase in myeloperoxidase activity, an indicator of the neutrophils accumulation in the colon (FIG. 18). This finding is consistent with the observation made with light microscopy that the colon of vehicle-treated DBNS-mice contained a large number of neutrophils. On the contrary, mAb 763 (10 mg/kg) treatment significantly reduced the degree of PMN infiltration (determined as increase in MPO activity) in inflamed colon (FIG. 18). On the contrary the treatment with mAb 763 at 3, 1, 0.5 mg/kg did not reduced the neutrophils infiltration in the colon tissues induced by DNBS-administration in mice (FIG. 18).

Please note that the treatment with CBH2 (10 mg/kg) did not reduce the macroscopic (FIGS. 15g and 15g1; see macroscopic score 13h) and histological signs of colon injury (FIG. 16g, see histological score 16h), the degree of PMN infiltration (FIG. 17) and the loss of body weight induced by DNBS-administration in mice (FIG. 18).

D. Effects of mAb 763 on DNBS-Induced Mediator Production from Colon Extracts

Figure 20:
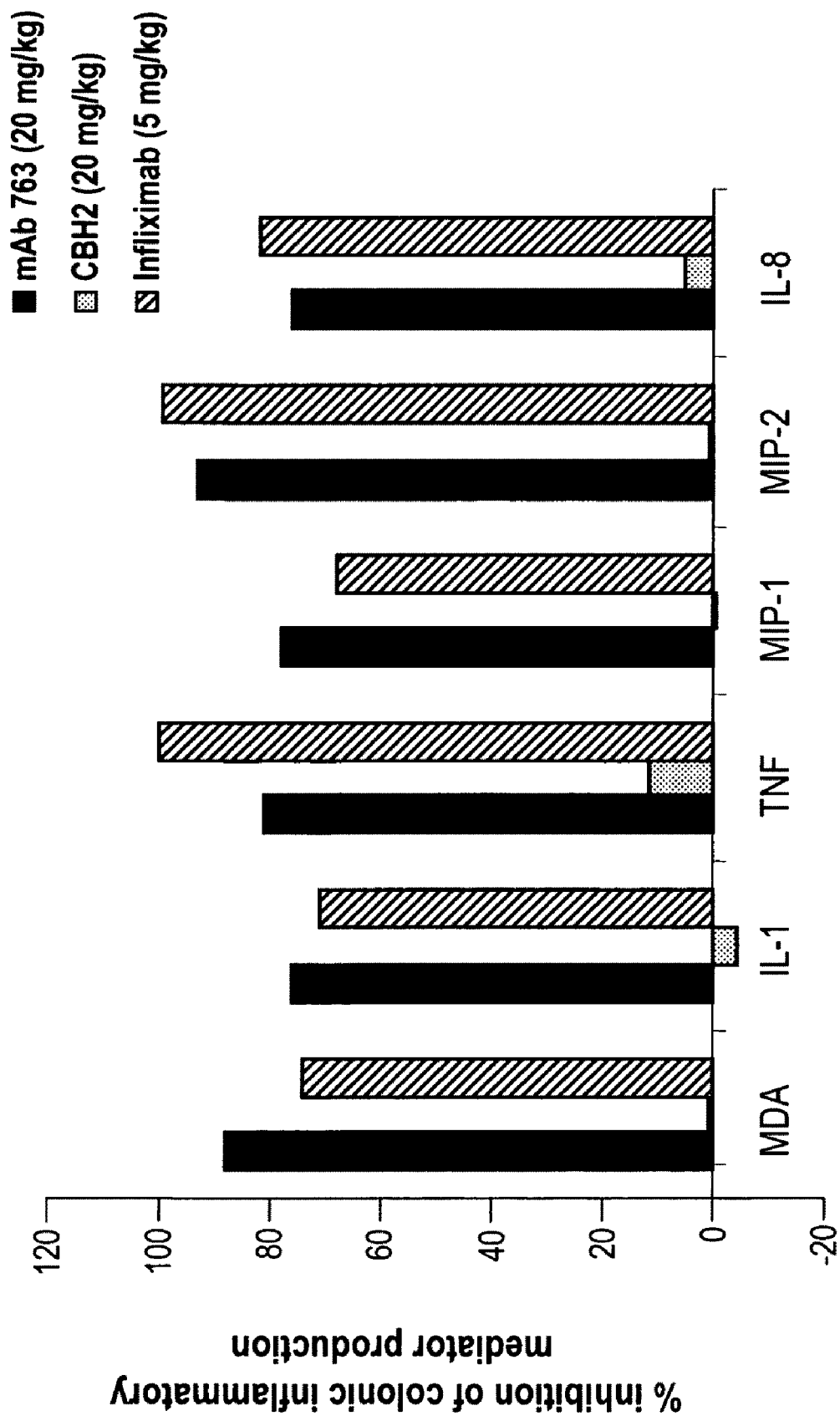
FIG. 20 is a graph depicting the inhibitory effects of mAb 763, a positive control mAb (Infliximab) and CBH2, a non-relevant human mAb control, on colonic mediator (i.e., MDA, IL-1β, TNFα, MIP-1, MIP-2 and IL-8) production in a DNBS-induced colitis model.

The effect of mAb 763 (10, 20 mg/kg), Infliximab (5 mg/kg) and non-relevant human mAb (20 mg/kg) on the production of DNBS-induced mediators was assessed (FIGS. 19 and 20).

1. Measurement of Cytokines and Chemokines

TNF-α, IL-10, IL-8, MIP-1, MIP-2 and IL-1β colonic levels were evaluated from colon tissues collected at 4 days after DNBS administration following preparation of colonic extracts. Quantitative determination of the levels of inflammatory mediators in the extracts were measured using commercially-available, ELISA kits.

2. Malondialdehyde (MDA) Measurement

Malondialdehyde levels in the colon tissue were determined as an indicator of lipid peroxidation. Colon tissue, collected at the specified time, were homogenised in 1.15% KCl solution. An aliquot (100 µl) of the homogenate was added to a reaction mixture containing 200 µl of 8.1% superoxide dismutaseium dodecyl sulphate, 1500 µl of 20% acetic acid (pH 3.5), 15001 of 0.8% thiobarbituric acid and 700 µl distilled water. Samples were then boiled for 1 h at 95° C. and centrifuged at 3,000×g for 10 min. The absorbance of the supernatant was measured by spectrophotometry at 650 nm.

3. Data Analysis

All values in the figures and text are expressed as mean±standard error (S.E.M.) of the mean of n observations. For the in vivo studies n represents the number of animals studied. In the experiments involving histology, the figures shown are representative of at least three experiments performed on different experimental days. The results were analysed by one-way analysis of variance followed by a Bonferroni post-hoc test for multiple comparisons. A P-value less than 0.05 was considered significant.

4. Effects of mAb 763 Treatment on Inflammatory Mediator Production in Colon Tissues The colitis caused by DNBS was also characterized by an increase in all inflammatory mediators examined (FIGS. 19 and 20). MDA levels were elevated ~6 fold in DNBS-treated animals, which were significantly attenuated by mAb 763 and infliximab. However, the non-relevant human mAb failed to affect DNBS-stimulated MDA production. Additionally, for all other colonic inflammatory mediators, DNBS caused a significant increase in IL-1β, TNF, MIP-1, MIP-2 and IL-8 levels, whose production were significantly attenuated with INO-763 but not by a human, non-relevant mAb (FIGS. 19 and 20).

E. Effects of Chimeric mAb at 20 (mg/kg) on DNBS-Induced Colitis

1. Experimental Groups: Animals were randomly divided into 5 groups (n=15 for each group):

| Group | DNBS | Treatment | Dosing |
|---|---|---|---|
| 1 | No | Sham-vehicle | 0.2 ml vehicle i.p. (saline solution) |
| 2 | Yes | Control-Vehicle | 0.2 ml vehicle i.p. (saline solution) |
| 3 | Yes | mAb 741 | 20 mg/kg i.p. |
| 4 | Yes | Chimeric mAb 741C | 20 mg/kg i.p. |
| 5 | Yes | Control mAb | 20 mg/kg i.p. |

2. Effects of Chimeric mAb Treatment on the Degree of Colitis

Figure 21:
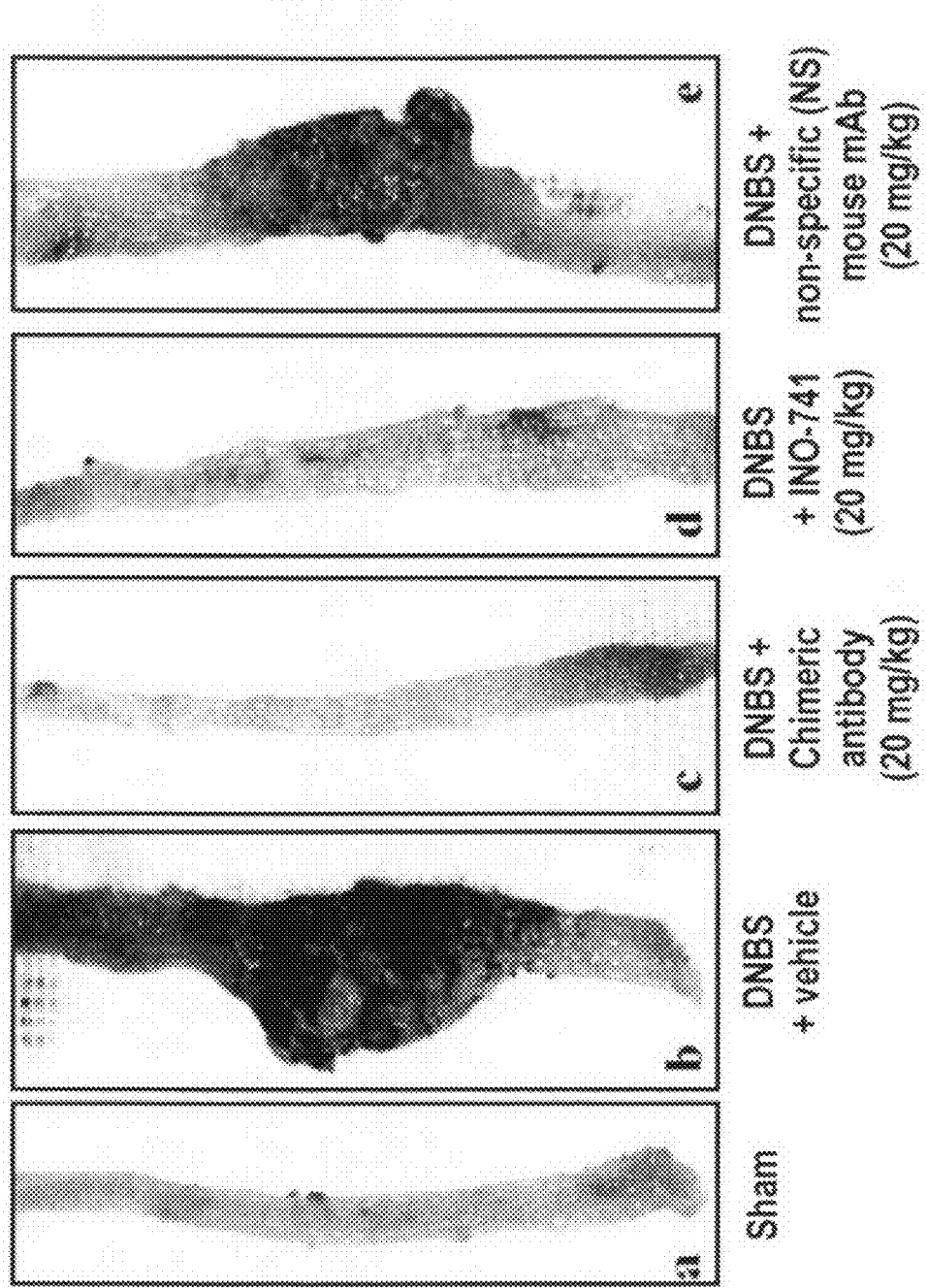
FIG. 21 depicts the macroscopic histological alterations of the colons of mice treated with either a sham-vehicle (FIG. 21a), a control-vehicle (FIG. 21b), DNBS and 20 mg/kg of chimeric mAb 741C (FIG. 21c), DNBS and 20 mg/kg of a murine mAb 741 (FIG. 21d), or DNBS and 20 mg/kg of a non-specific, murine control mAb (FIG. 21e).
Figure 22:
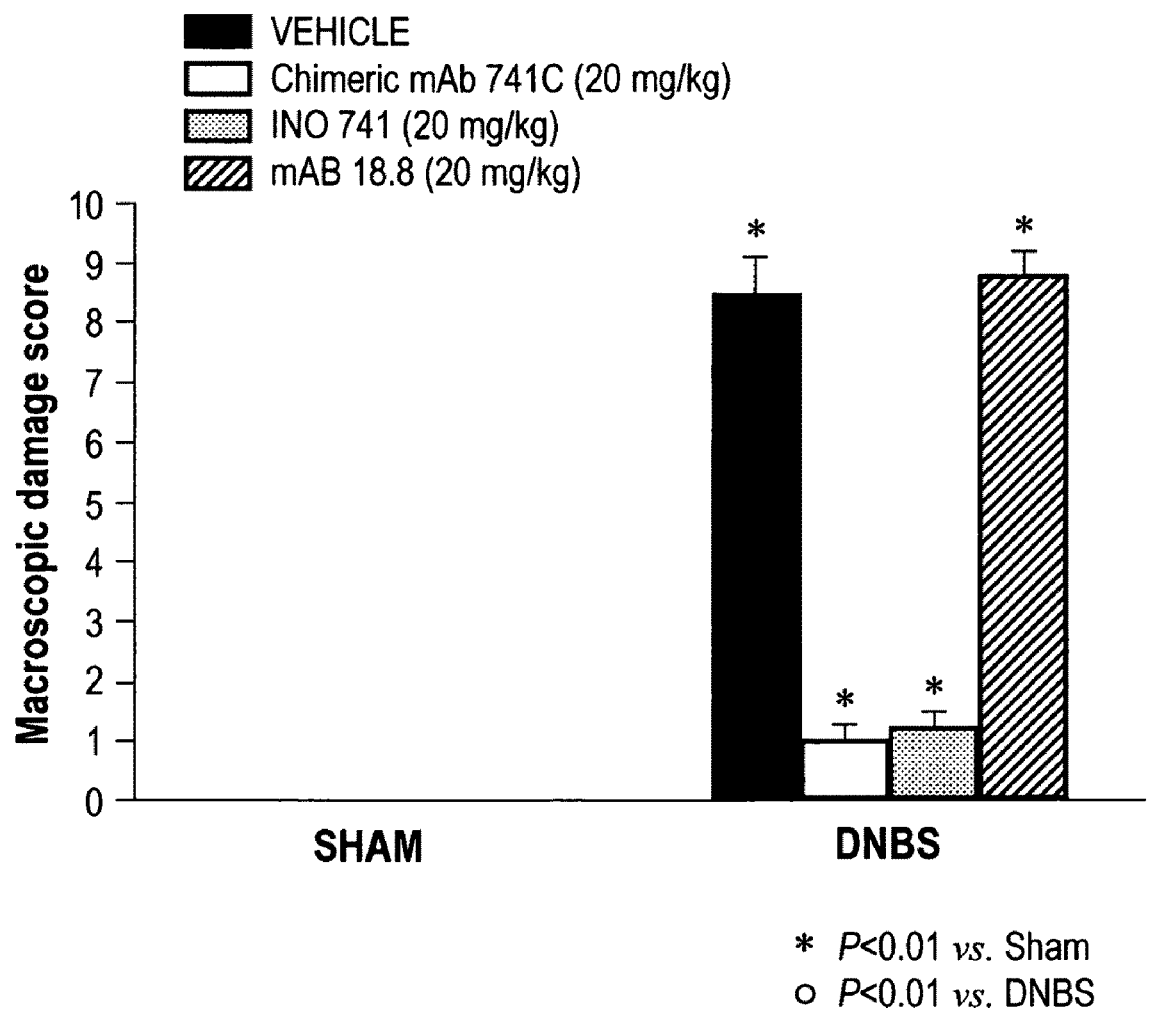
FIG. 22 depicts the macroscopic damage score of mice treated with either a sham-vehicle, a control-vehicle, DNBS and 20 mg/kg of chimeric mAb 741C, DNBS and 20 mg/kg of a murine mAb 741, or DNBS and 20 mg/kg of a non-specific, control mAb (mAb 18.8).
Figure 23:
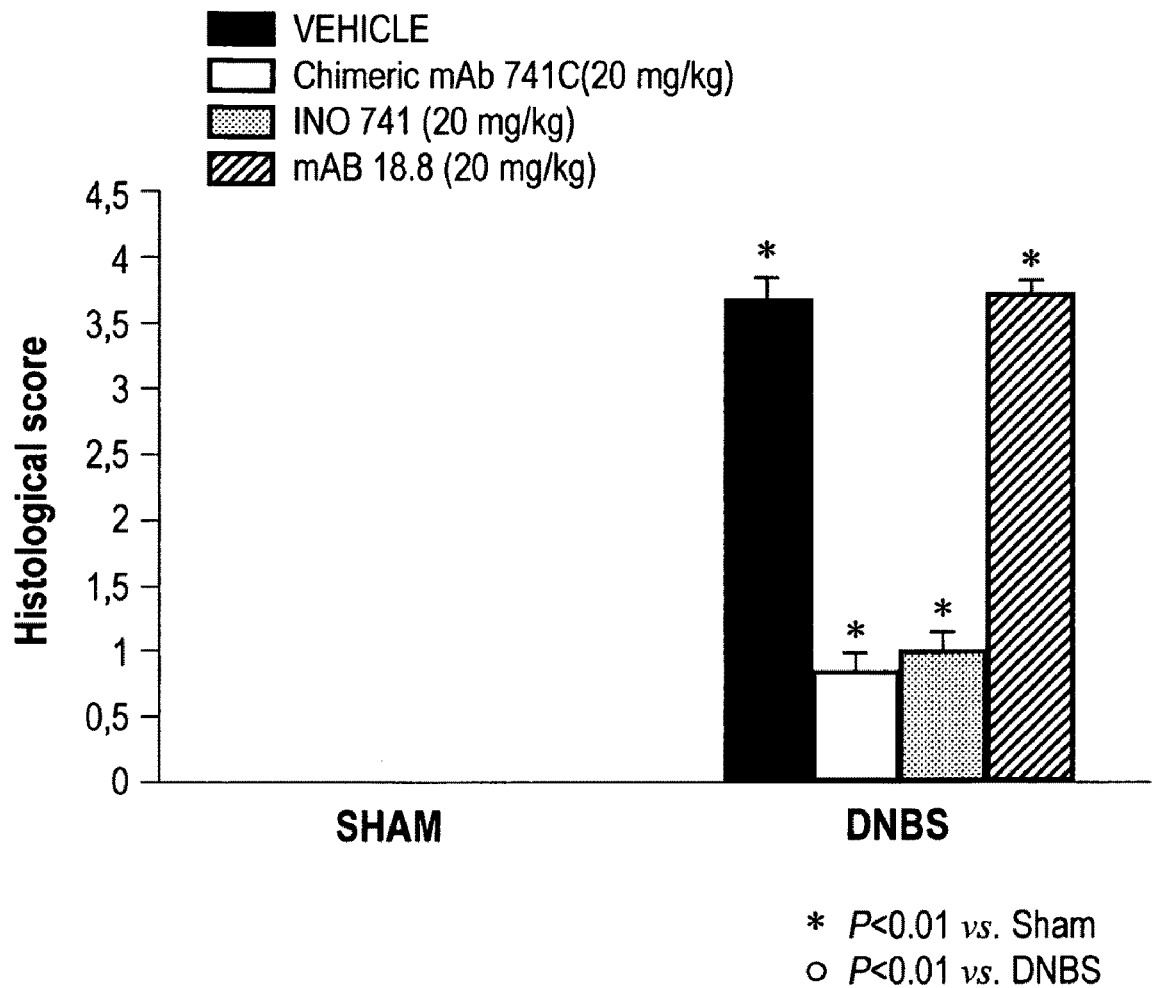
FIG. 23 depicts the histological score of mice treated with either a sham-vehicle, a control-vehicle, DNBS and 20 mg/kg of chimeric mAb 741C, DNBS and 20 mg/kg of a murine mAb 741, or DNBS and 20 mg/kg of a non-specific, control mAb (mAb 18.8).
Figure 24:
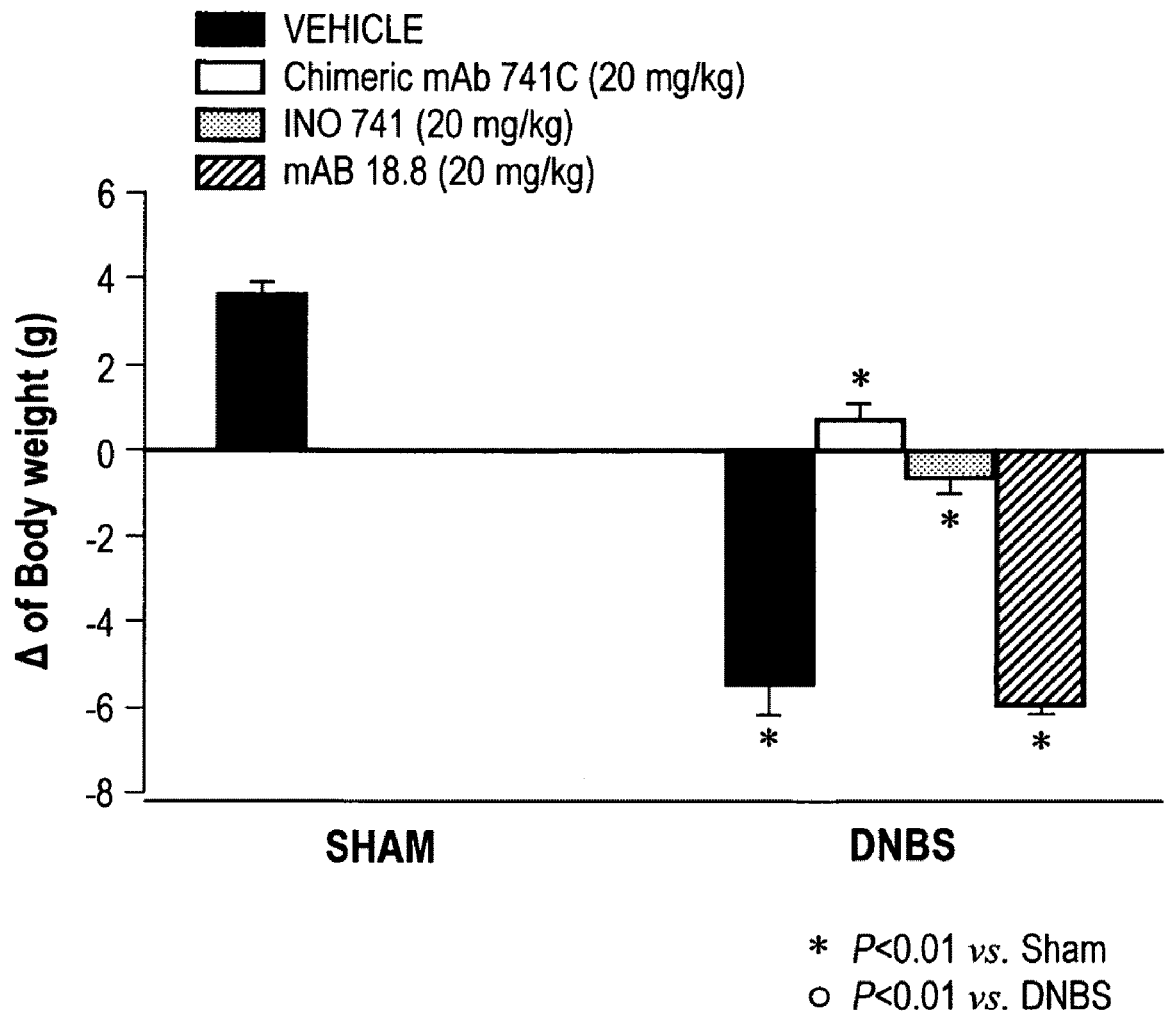
FIG. 24 is a graph illustrating the change in body weight in grams of mice treated with either a sham-vehicle, a control-vehicle, DNBS and 20 mg/kg of chimeric mAb 741C, DNBS and 20 mg/kg of murine mAb 741, or DNBS and 20 mg/kg of a non-specific, control mAb (mAb 18.8).

No histological alteration was observed in the colon tissue from sham-treated mice (see FIG. 21O; see macroscopic score FIG. 22; see histological score FIG. 23). Treatment with chimeric mAb 741C (20 mg/kg) significantly reduced the extent and severity of the macroscopic (see FIG. 22) and histological signs of colon injury (see FIG. 21c). Similarly, the treatment with murine mAb 741 significantly reduced the macroscopic and histological signs of colon injury. On the contrary, treatment with a non-specific control murine mAb (mAb 18.8) (20 mg/kg) did not reduced the extent and severity of the macroscopic (see FIG. 22) and histological signs of colon injury (see FIG. 21). Four days after colitis induced by DNBS treatment, all mice except for those treated with the chimeric mAb, had diarrhea and a reduction in body weight (compared with the sham groups of mice) (FIG. 24). Chimeric mAb 741C (20 mg/kg) treatment resulted in a significant reduction of loss of body weight induced by DNBS-administration in mice (FIG. 24).

Figure 25:
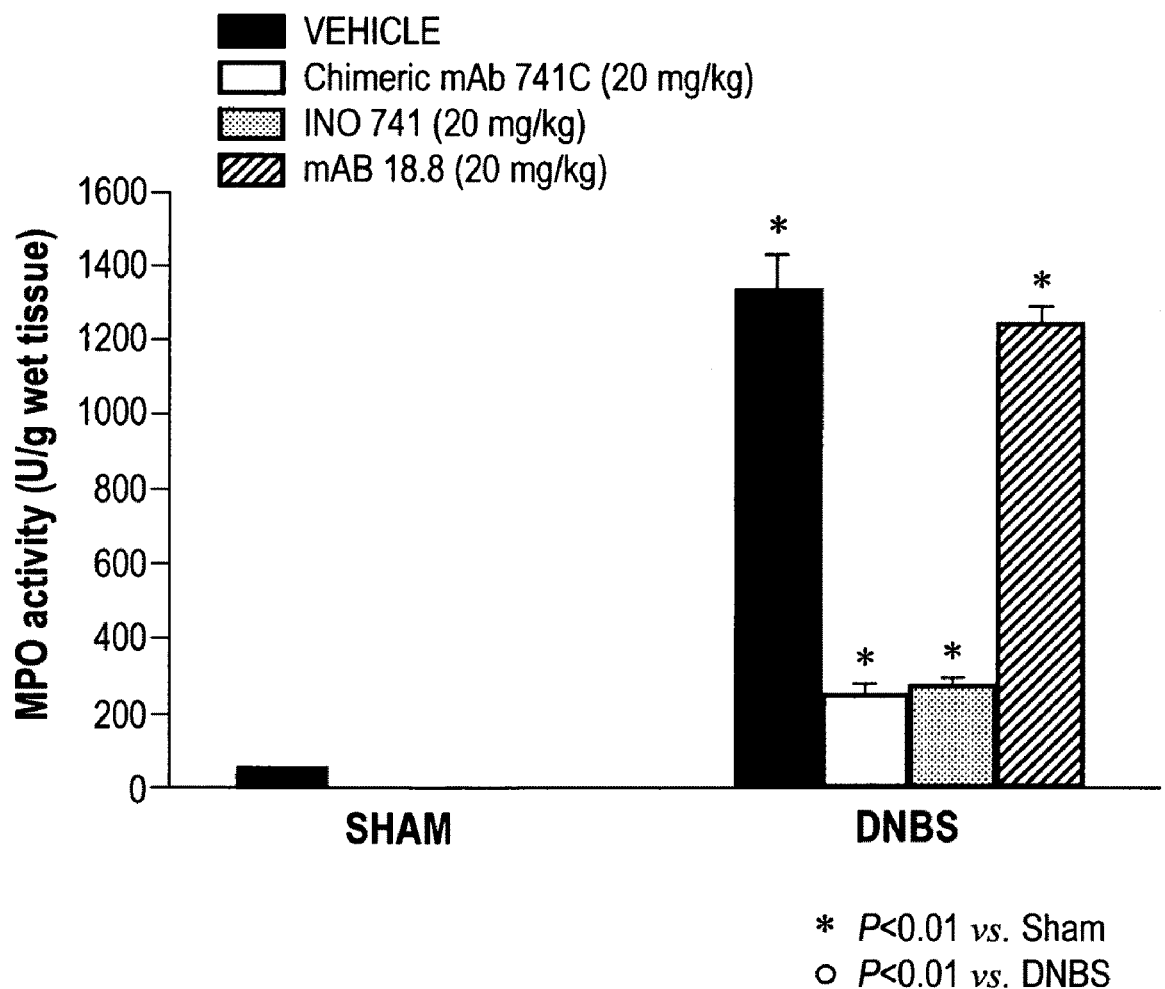
FIG. 25 is a graph illustrating myeloperoxidase (MPO) activity in mice treated with either a sham-vehicle, a control-vehicle, DNBS and 20 mg/kg of chimeric mAb 741C, DNBS and 20 mg/kg of murine mAb 741, or DNBS and 20 mg/kg of a non-specific, control mAb (mAb 18.8).

The colitis caused by DNBS was also characterized by an increase in myeloperoxidase activity, an indicator of the neutrophils accumulation in the colon (FIG. 25). On the contrary, chimeric mAb 741C (20 mg/kg) treatment significantly reduced the degree of PMN infiltration (determined as increase in MPO activity) in inflamed colon (FIG. 25). Similarly, the treatment with mAb 741 reduced the neutrophils infiltration in the colon tissues induced by DNBS-administration in mice (FIG. 25). On the contrary the treatment with a non-specific control murine mAb (mAb 18.8) (20 mg/kg) did not reduced the neutrophils infiltration in the colon tissues induced by DNBS-administration in mice (FIG. 25).

3. Effect of Chimeric mAb Treatment on Mortality

Figure 26:
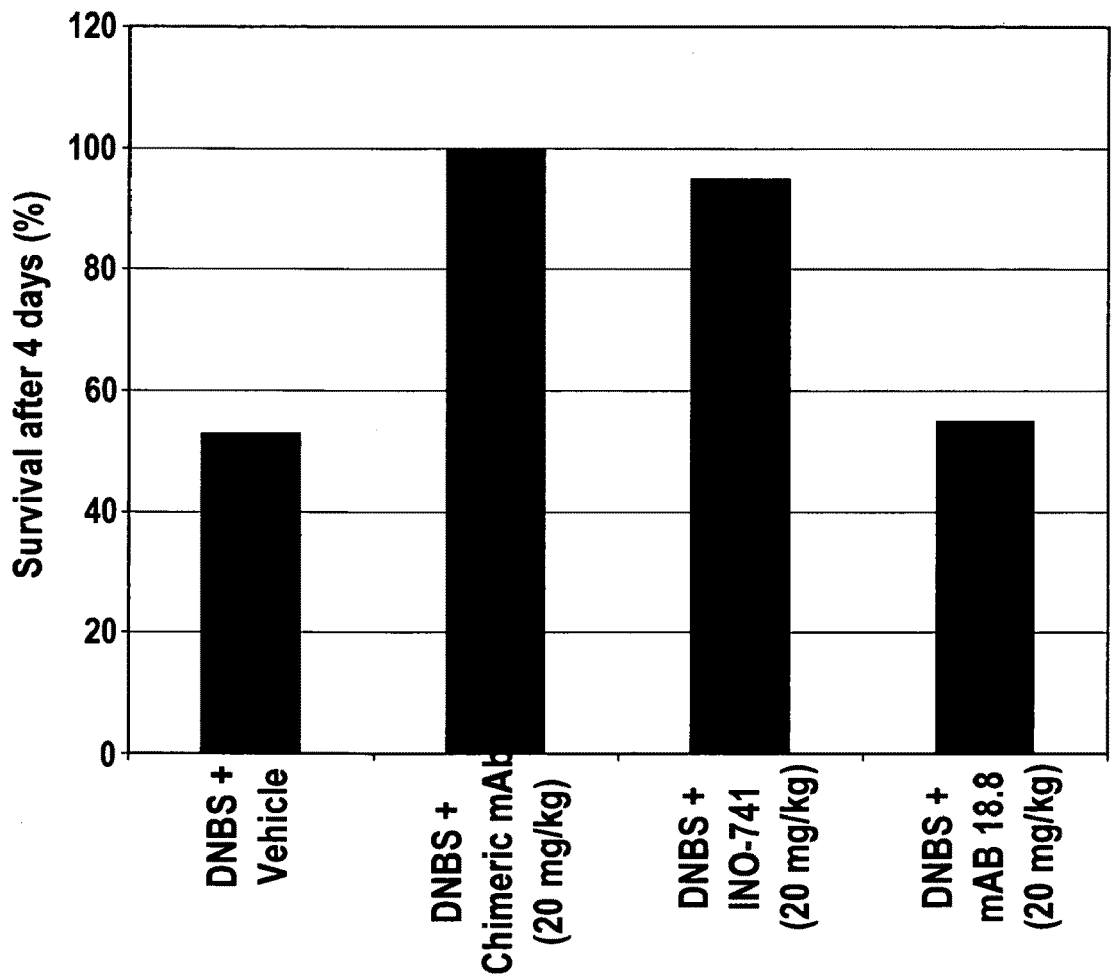
FIG. 26 is a graph showing the effects of chimeric mAb 741C on mortality in an in vivo murine model of colitis.

DNBS-mice, which had received vehicle, developed severe hemorrhagic diarrhoea, and greater than 50% of these animals died within 4 days (FIG. 26). In contrast, no DNBS-treated mice which had been treated with chimeric mAb 741C (20 mg/kg) died.

Figure 27:
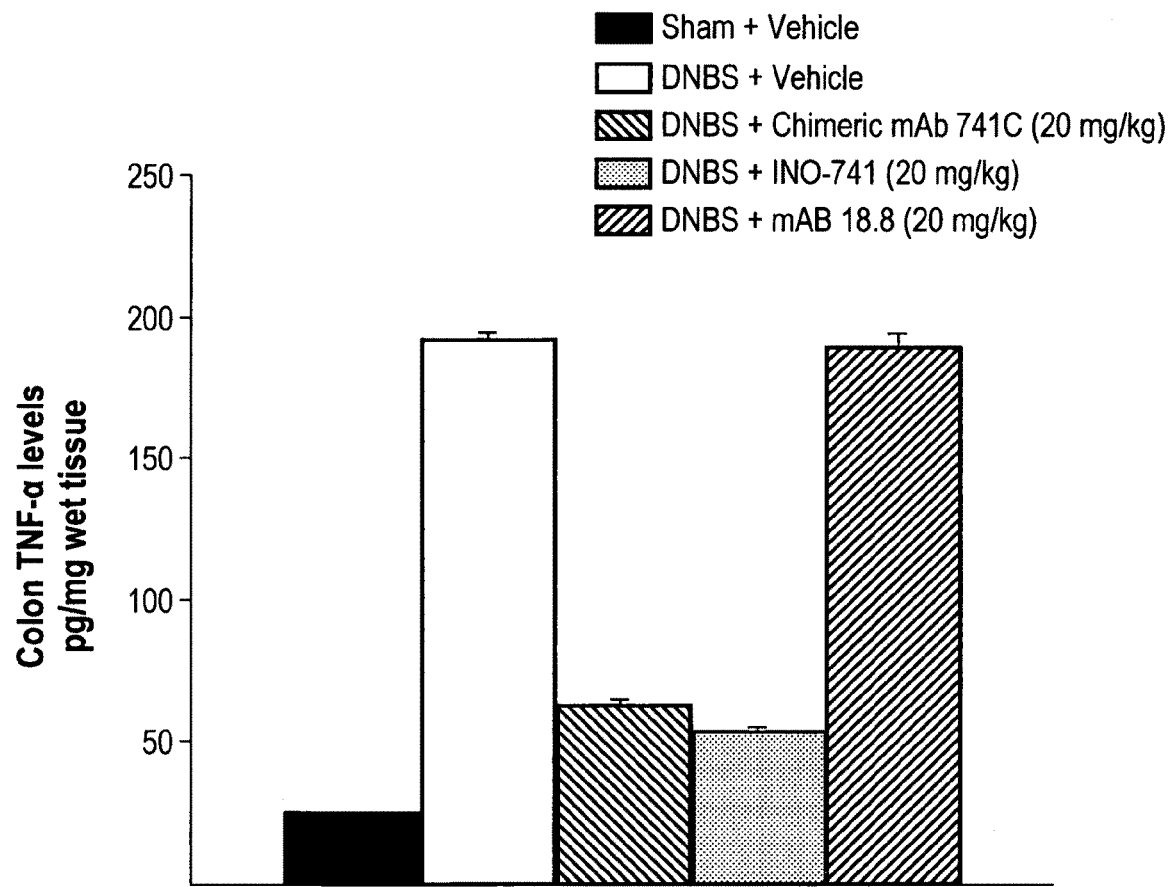
FIG. 27 is a graph depicting the inhibitory effects of mAb 741 and chimeric mAb 741C on TNFα production in a DNBS-induced colitis model.
Figure 28:
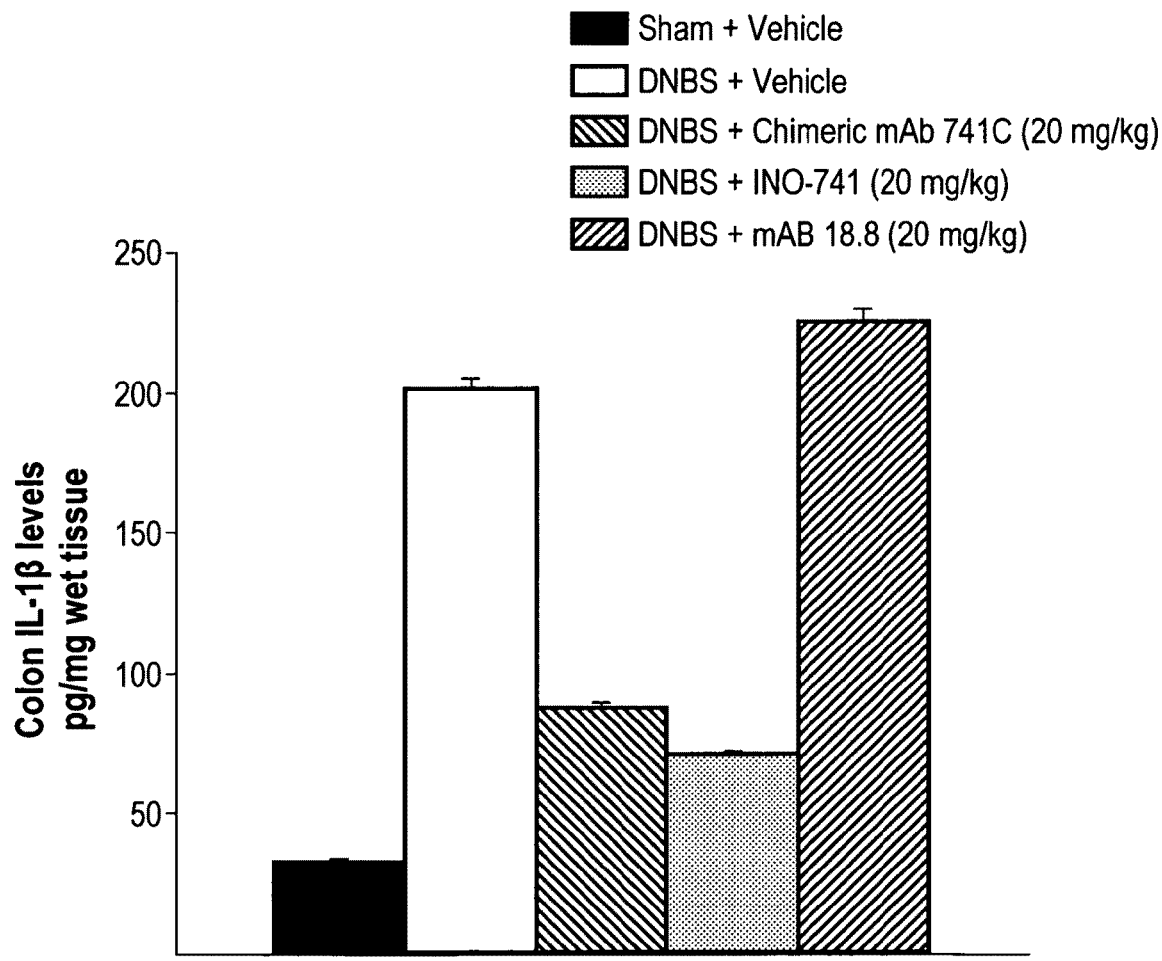
FIG. 28 is a graph depicting the inhibitory effects of mAb 741 and chimeric mAb 741C on IL-1-β production in a DNBS-induced colitis model.
Figure 29:
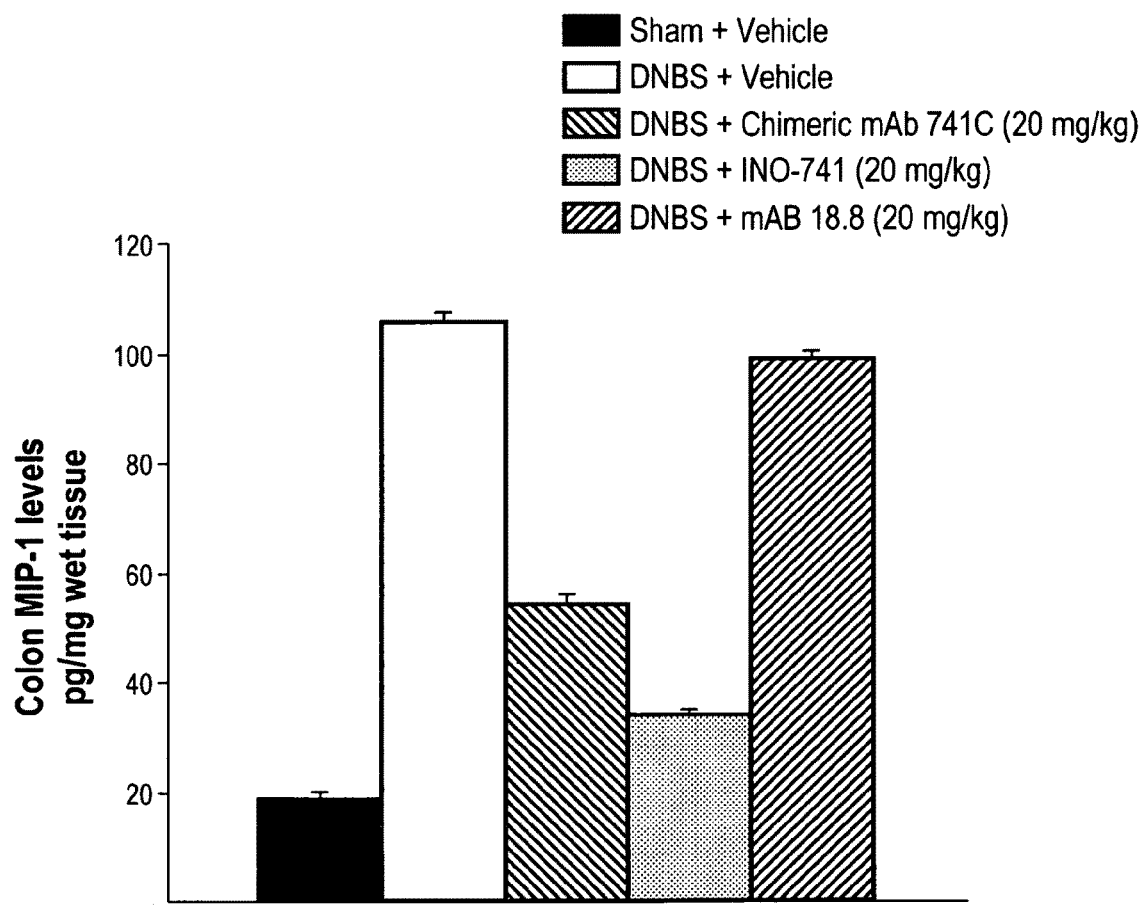
FIG. 29 is a graph depicting the inhibitory effects of mAb 741 and chimeric mAb 741C on MIP-1 production in a DNBS-induced colitis model.

F. Effects of Chimeric mAb 741C on DNBS-Induced Mediator Production from Colon Extracts The effect of chimeric mAb 741C (20 mg/kg), murine mAb 741, and an isotype mouse control mAb, 18.8 (20 mg/kg) on the production of DNBS-induced mediators was assessed (FIGS. 27-29).

1. Measurement of Cytokines and Chemokines

TNF-α, IL-1β and MIP-1 colonic levels were evaluated from colon tissues collected at 4 days after DNBS administration following preparation of colonic extracts. Quantitative determination of the levels of inflammatory mediators in the extracts were measured using commercially-available, ELISA kits.

2. Data Analysis

All values in the figures and text are expressed as mean±standard error (S.E.M.) of the mean of n observations. For the in vivo studies n represents the number of animals studied. In the experiments involving histology, the figures shown are representative of at least three experiments performed on different experimental days. The results were analysed by one-way analysis of variance followed by a Bonferroni post-hoc test for multiple comparisons. A P-value less than 0.05 was considered significant.

3. Effects of Chimeric mAb 741C Treatment on Inflammatory Mediator Production in Colon Tissues The colitis caused by DNBS was characterized by an increase in all three inflammatory mediators examined (FIGS. 27, 28 and 29). TNF-α, IL-1β and MIP-1 levels were significantly elevated in DNBS-treated animals and were significantly attenuated by both mAb 741 and chimeric mAb 741C. However, the isotype mouse control mAb, 18.8, failed to affect the production of DNBS-stimulated inflammatory mediators.

Example 7

Figure 30:
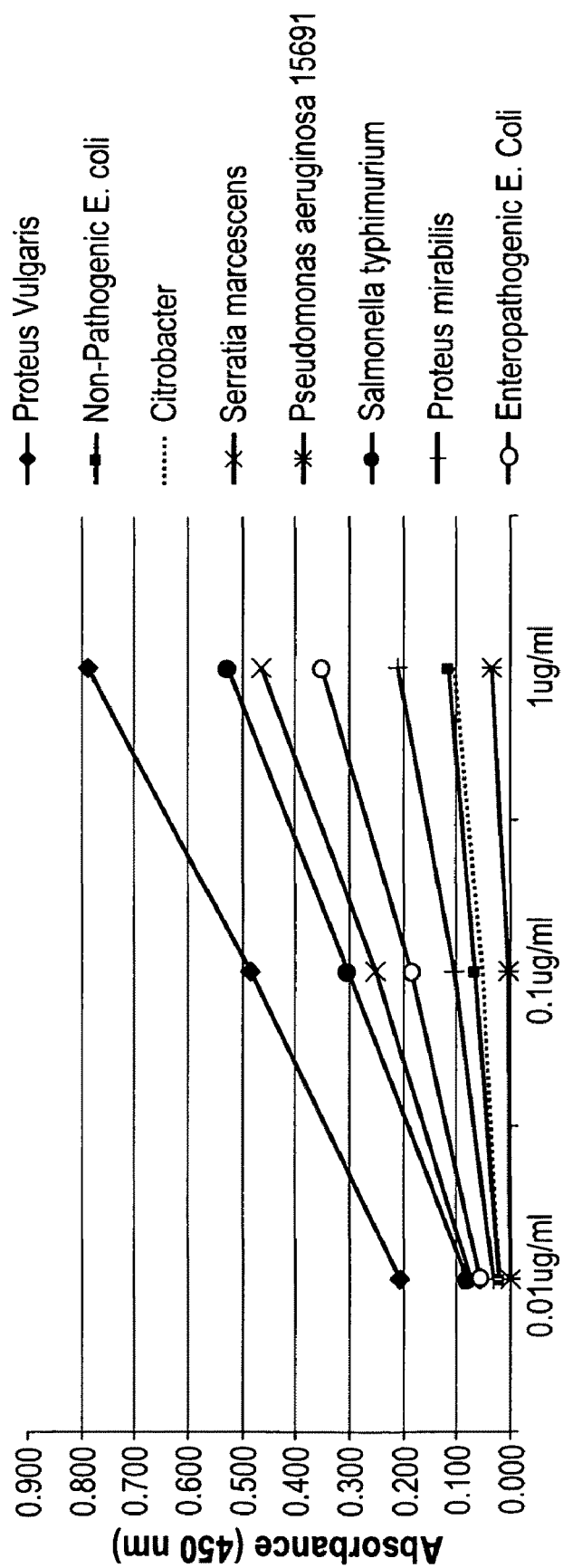
FIG. 30 is a graph showing the specific, wide-spread, reactivity of mAb 741 to a variety of gram-negative bacteria in a live bacterial ELISA assay.
Figure 31:
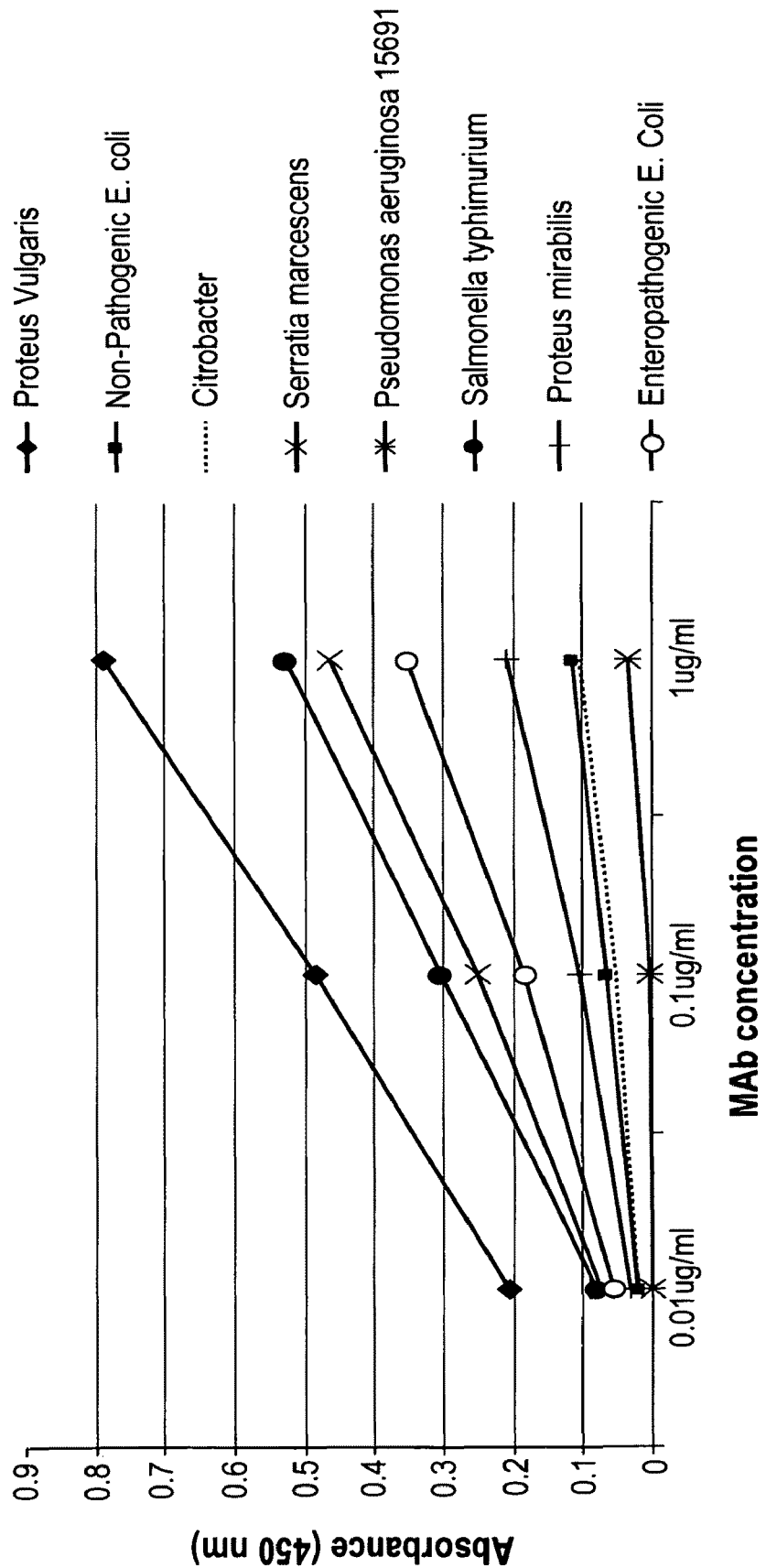
FIG. 31 is a graph showing the specific, wide-spread reactivity of mAb 763 to a variety of gram-negative bacteria in a live bacterial ELISA assay.

Anti-Flagellin Monoclonal Antibodies Cross-React with a Broad Spectrum of Gram-Negative Bacteria Dose-response binding relative to mAb 763 and mAb 741 was assessed towards a panel of different gram-negative bacteria (i.e., *Proteus Vulgaris*, non-pathogenic *E. Coli*, *Citrobacter*, *Serratia marcenscens*, *Pseudomonas aeruginosa*, *Salmonella typhimurium*, *Proteus mirabilis*, Enteropathogenic *E. Coli*) in a live bacterial ELISA assay. Both mAb 763 and mAb 741 bound cross-reactively to a variety of different bacteria with highest binding observed towards *Proteus mirabilis*, *Salmonella typhimurium*, *Serratia marcenscens*, and Enteropathogenic *E. Coli* (FIGS. 30 and 31).

Example 8

Binding Affinities

The binding affinity of mAb 763 was determined towards *Salmonella* and *Pseudomonas* flagellin using the BIACore system. The affinity of mAb 763 towards *Salmonella* flagellin was ~$10^{-10}$ M and the affinity of mAb 763 towards *Pseudomonas* flagellin was ~$10^{-6}$ M.

Example 9

In Vivo Treatment of Colitis

The effects of the anti-flagellin antibodies of the present invention (e.g., mAb 741 and mAb 763) can be tested in an IL-10 k/o mouse model of colitis. For example, a 10 week model can be employed wherein the antibodies are administered at either week 6 (i.e., a prophylactic regimen) or week 9 (i.e., a treatment paradigm wherein colitis has been established). At week 16, animals can be sacrificed and markers of colonic injury assessed.

Example 10

In Vitro Nitric Oxide Production Assay

An in vitro nitric oxide (NO) production assay was used to assess the functional characteristics of murine mAb 741 and human mAb 763. DLD-1 cells (ATCC) were grown at 37° C. in 5% $CO_2$ in Dulbecco's modified Eagle's medium (DMEM, Invitrogen) and were supplemented with 10% FBS, 4 mM glutamine, 1.5 g/liter sodium bicarbonate, 4.5 g/liter glucose, 1 mM sodium pyruvate, and antibiotics. Cells, between passages 5 and 15, were seeded at a density of 50,000 cells/cm2 in 96-well plates and allowed to grow 72-96 hours to confluence before use. Growth medium was changed the day before use. Cells were washed once with DMEM without FBS (but containing antibiotics) before the addition of flagellin proteins. Flagellin to be tested were added to 100 µl growth medium containing 0.5% FBS and 100 U/ml IFN-γ in each well. To neutralize NO production activity, the recombinant flagellin was incubated with antibodies for 1 hour at room temperature and then added to DLD-1 cells in 96 well plate. After 20 hours of incubation at 370 C, the culture medium was removed and tested for NO2-/NO3- concentration by Greiss assay (Salzman et al. *Am J Physiol.* 268, 361-73 (1995)).

Figure 32:
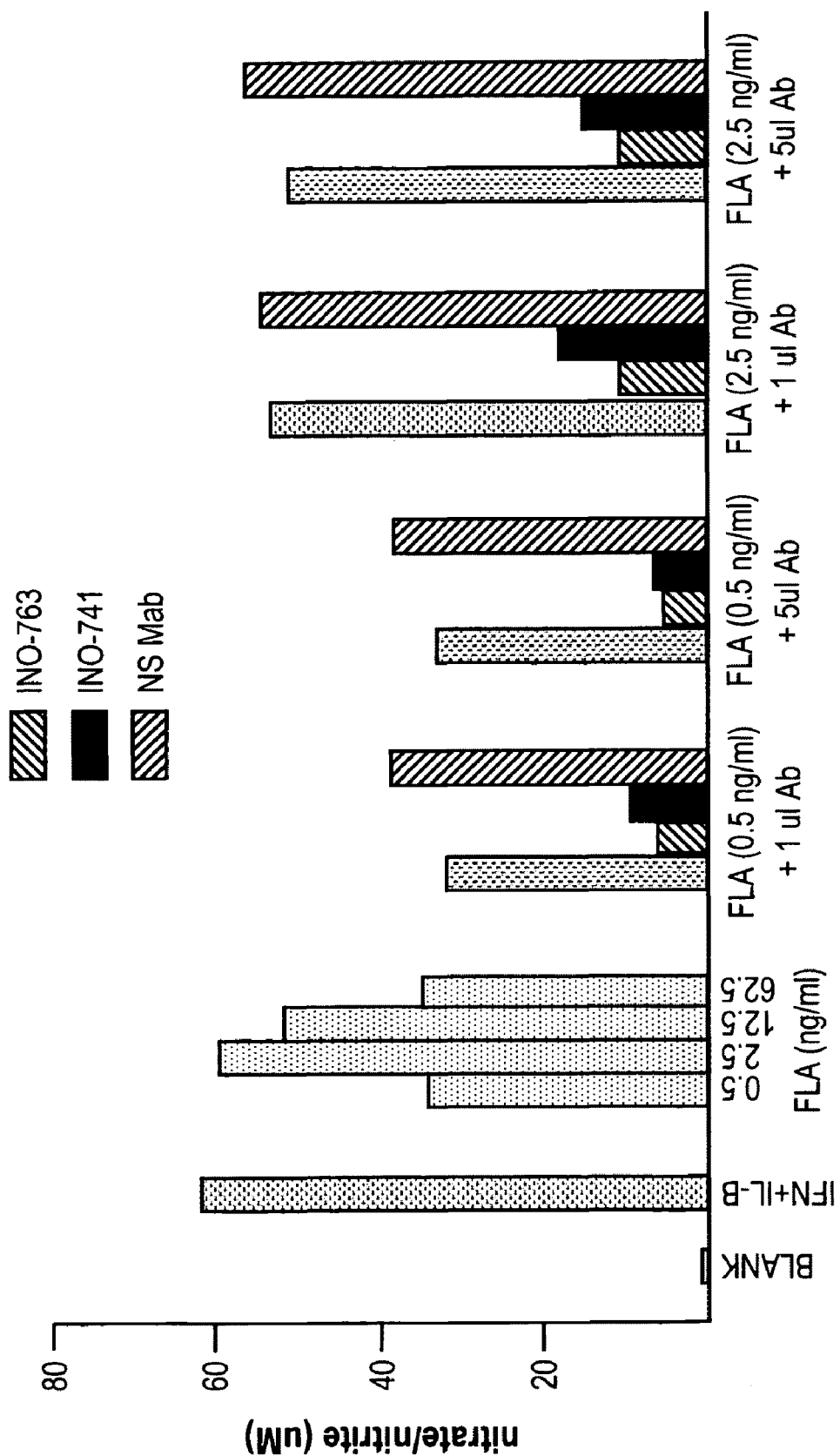
FIG. 32 is a graph showing that anti-flagellin mAbs 741 and 763 inhibit flagellin activity in an NO production assay.

As depicted in FIG. 32, both mAb 741 and mAb 763 inhibited flagellin activity in the NO production assay.

Example 11

Additional In Vitro Functional Assays

A number of in-vitro functional assays can be performed to assess the functional characteristics of the anti-flagellin antibodies of the present invention (e.g., murine mAb 741, chimeric mAb 741 and 763). Such assays can include, but are not limited to, assays designed to assess the effect of anti-flagellin antibodies on (1) bacterial invasion into susceptible epithelial cells, (2) inhibition of flagellin-stimulated NO or IL-8 production from epithelial cells, (3) bacterial opsonophagocytosis, (3) macrophage ingestion of bacteria, (4) bacterial "killing" and (5) superoxide production.

EQUIVALENTS

Those skilled in the art will recognize, or be able to ascertain using no more than routine experimentation, many equivalents of the specific embodiments of the invention described herein. Such equivalents are intended to be encompassed by the following claims. Any combination of the embodiments disclosed in the dependent claims are contemplated to be within the scope of the invention.

INCORPORATION BY REFERENCE

All publications, patents, and pending patent applications referred to herein are hereby incorporated by reference in their entirety.

SUMMARY OF SEQUENCE LISTING

| SEQ ID NO: | SEQUENCE |
|---|---|
| 1 | VH a.a. 741 |
| 2 | VH a.a. 763 |
| 3 | VK a.a. 741 |
| 4 | VK a.a. 763 |
| 5 | VH CDR1 a.a. 741 |
| 6 | VH CDR1 a.a. 763 |
| 7 | VH CDR2 a.a. 741 |
| 8 | VH CDR2 a.a. 763 |
| 9 | VH CDR3 a.a. 741 |
| 10 | VH CDR3 a.a. 763 |
| 11 | VK CDR1 a.a. 741 |
| 12 | VK CDR1 a.a. 763 |
| 13 | VK CDR2 a.a. 741 |
| 14 | VK CDR2 a.a. 763 |
| 15 | VK CDR3 a.a. 741 |
| 16 | VK CDR3 a.a. 763 |
| 17 | Sense Primer Designated 1S |
| 18 | Antisense Primer Designated 468A |
| 19 | VH n.t. 741 |
| 20 | VH n.t. 763 |
| 21 | VK n.t. 741 |
| 22 | VK n.t. 763 |
| 23 | VH CDR1 n.t. 741 |
| 24 | VH CDR1 n.t. 763 |
| 25 | VH CDR2 n.t. 741 |
| 26 | VH CDR2 n.t. 763 |
| 27 | VH CDR3 n.t. 741 |
| 28 | VH CDR3 n.t. 763 |
| 29 | VK CDR1 n.t. 741 |
| 30 | VK CDR1 n.t. 763 |
| 31 | VK CDR2 n.t. 741 |
| 32 | VK CDR2 n.t. 763 |
| 33 | VK CDR3 n.t. 741 |
| 34 | VK CDR3 n.t. 763 |
| 35 | *Proteus mirabilis* (GI: 1169696) |
| 36 | *Pseudomonas aeruginosa* (GI: 3386643) |
| 37 | *Escherichia coli* (GI: 1655807) |
| 38 | *Serratia marcescens* (GI: 514988) |
| 39 | *Salmonella muenchen* (GI: 1333832) |
| 40 | *Salmonella typhimurium* (GI: 153979) |
| 41 | Amino acids 1-156 of flagellin gene of *Salmonella muenchen* (GI: 47233) |

The invention claimed is:

1. A method of treating inflammatory bowel disease (IBD) in a subject, comprising administering to the subject a therapeutically effective amount of an isolated monoclonal antibody which binds to and neutralizes flagellin, wherein the antibody is selected from the group consisting of: (a) an antibody comprising a heavy chain variable region comprising the amino acid sequence set forth in SEQ ID NO: 1 and a light chain variable region comprising the amino acid sequence set forth in SEQ ID NO:3; and (b) an antibody comprising heavy and light chain variable region CDR1, CDR2 and CDR3, wherein the heavy chain variable region CDR1 comprises SEQ ID NO:5; the heavy chain variable region CDR2 comprises SEQ ID NO:7; the heavy chain variable region CDR3 comprises SEQ ID NO:9; the light chain variable region CDR1 comprises SEQ ID NO: 11; the light chain variable region CDR2 comprises SEQ ID NO: 13; and the light chain variable region CDR3 comprises SEQ ID NO: 15.

2. The method of claim 1, wherein the antibody comprises a heavy chain variable region comprising the amino acid sequence set forth in SEQ ID NO:1 and a light chain variable region comprising the amino acid sequence set forth in SEQ ID NO:5.

3. The method of claim 1, wherein the IBD is Crohn's Disease or colitis.

4. The method of claim 1, wherein the IBD is caused by an enterobacteria.

5. The method of claim 1, wherein the antibody specifically binds to an epitope located between amino acids 1-55 of flagellin from *Salmonella* (SEQ ID NO:39) or *Pseudomonas* (SEQ ID NO:36).

6. The method of claim 5, wherein the antibody specifically binds to an epitope located between amino acids 1-40 of flagellin from *Salmonella* (SEQ ID NO:39) or *Pseudomonas* (SEQ ID NO:36).

7. The method of claim 1, wherein the subject is human.

8. The method of claim 1, wherein the antibody is administered intravenously, intramuscularly, or subcutaneously to the subject.

9. The method of claim 1, wherein the antibody is administered in combination with a second therapeutic agent.

10. The method of claim 9, wherein the second therapeutic agent is a second antibody.

11. The method of claim 9, wherein the second therapeutic agent is an antibiotic.

12. The method of claim 1, wherein the antibody is selected from the group consisting of, a humanized antibody, and a chimeric antibody.

13. The method of claim 1, wherein the antibody is selected from the group consisting of a Fab, Fab'2, and ScFv.

14. The method of claim 1, wherein the antibody is selected from the group consisting of an IgG1, an IgG2, an IgG3, an IgG4, an IgM, an IgA1, an IgA2, an IgAsec, an IgD, and an IgE antibody.

15. The method of claim 1, wherein the antibody comprises heavy and light chain variable region CDR1, CDR2 and CDR3, wherein the heavy chain variable region CDR1 comprises SEQ ID NO:5, the heavy chain variable region CDR2 comprises SEQ ID NO:7, the heavy chain variable region CDR3 comprises SEQ ID NO:9, the light chain variable region CDR1 comprises SEQ ID NO:11, the light chain variable region CDR2 comprises SEQ ID NO: 13, and the light chain variable region CDR3 comprises SEQ ID NO: 15.

* * * * *